United States Patent
Itskovitz-Eldor et al.

(10) Patent No.: US 8,343,762 B2
(45) Date of Patent: Jan. 1, 2013

(54) HUMAN EMBRYONIC STEM CELL-DERIVED CONNECTIVE TISSUE PROGENITORS FOR TISSUE ENGINEERING

(75) Inventors: Joseph Itskovitz-Eldor, Haifa (IL); Shahar Cohen, Kiryat-Motzkin (IL)

(73) Assignee: Technion Research & Development Foundation Ltd., Haifa (IL)

( * ) Notice: Subject to any disclaimer, the term of this patent is extended or adjusted under 35 U.S.C. 154(b) by 778 days.

(21) Appl. No.: 12/087,610

(22) PCT Filed: Jan. 11, 2007

(86) PCT No.: PCT/IL2007/000046
§ 371 (c)(1), (2), (4) Date: Aug. 17, 2009

(87) PCT Pub. No.: WO2007/080590
PCT Pub. Date: Jul. 19, 2007

(65) Prior Publication Data
US 2010/0035341 A1 Feb. 11, 2010

Related U.S. Application Data

(60) Provisional application No. 60/861,081, filed on Nov. 27, 2006, provisional application No. 60/861,080, filed on Nov. 27, 2006, provisional application No. 60/757,864, filed on Nov. 1, 2006.

(51) Int. Cl.
*C12N 15/00* (2006.01)
(52) U.S. Cl. .......... 435/373; 435/377; 435/384
(58) Field of Classification Search .......... None
See application file for complete search history.

(56) References Cited

U.S. PATENT DOCUMENTS

| | | | |
|---|---|---|---|
| 2003/0021771 A1 | 1/2003 | Xu et al. | |
| 2003/0026786 A1 | 2/2003 | Pittenger et al. | |
| 2003/0036194 A1 | 2/2003 | Xu et al. | |
| 2003/0109038 A1 | 6/2003 | Thies | |
| 2003/0219423 A1 | 11/2003 | Gazit et al. | |
| 2009/0093056 A1 | 4/2009 | Itskovitz-Eldor et al. | |

FOREIGN PATENT DOCUMENTS

| | | |
|---|---|---|
| EP | 1627913 | 2/2006 |
| WO | WO 2005/001076 | 1/2005 |
| WO | WO 2005/012512 | 2/2005 |
| WO | WO 2005/108559 | 11/2005 |
| WO | WO 2005/121319 | 12/2005 |
| WO | WO 2007/080590 | 7/2007 |
| WO | WO 2007/080591 | 7/2007 |

OTHER PUBLICATIONS

Li et al. Mesenchymal stem cells derived from human placenta suppress allogeneic umbilical cord blood lymphocyte proliferation. Cell Research, 2005, vol. 15, pp. 539-547.*
Sottile et al. In Vitro Osteogenic Differentiation of Human ES Cells. Cloning and Stem Cells, 2003, vol. 5, pp. 149-155.*
Kuznetsov et al. Effect of Serum on Human Bone Marrow Stromal Cells: Ex Vivo Expansion and In Vivo Bone FormationTransplantation, 2000, vol. 70, pp. 1780-1787.*
Office Action Dated Mar. 24, 2011 From the Israel Patent Office Re. Application No. 192709 and Its Translation Into English.
Office Action Dated Mar. 24, 2011 From the Israel Patent Office Re. Application No. 192710 and Its Translation Into English.
Response Dated Mar. 24, 2011 to Communication Pursuant to Article 94(3) EPC of Nov. 26, 2010 From the European Patent Office Re.: Application No. 07700738.3.
Response Dated Aug. 23, 2010 to Official Action of Jul. 22, 2010 From the US Patent and Trademark Office Re. U.S. Appl. No. 12/087,664.
Search Report and Written Opinion Dated Aug. 2, 2010 From the Intellectual Property Office of Singapore Issued on Jan. 18, 2010 by the Austrian Patent Office Re. Application No. 200805146-8.
Coelho et al. "Human Bone Cell Cultures in Biocompatibility Testing. Part II: Effect of Ascorbic Acid, β-Glycerophosphate and Dexamethasone on Osteoblastic Differentiation", Biomaterials, 21(11): 1095-1102, Jun. 2000.
Mauney et al. "Matrix-Mediated Retention of Adipogenic Differentiation Potential by Human Adult Bone Marrow-Derived Mesenchymal Stem Cells During Ex Vivo Expansion", Biomaterials, 26(31): 6167-6175, Nov. 2005.
Walsh et al. "High Concentrations of Dexamethasone Suppress the Proliferation But Not the Differentiation or Further Maturation of Human Osteoblast Precursors In Vitro: Relevance to Glucocorticoid-Induced Osteoporosis", Rheumatology, 40(1): 74-83, 2001.
Written Opinion Dated Oct. 15, 2008 From the International Searching Authority Re.: Application No. PCT/IL07/00047.
Campagnoli et al. "Identification of Mesenchymal Stem/Progenitor Cells in Human First-Trimester Fetal Blood, Liver, and Bone Marrow", Blood, 98(8): 2396-2402, Oct. 15, 2001. Abstract, p. 2397, r-h Col., § 3, 1-h Col., § 1, 3, p. 2398, r-h Col., § 3, p. 2399, Fig.2, p. 2400, Fig.5.
Communication Pursuant to Article 94(3) EPC Dated Oct. 29, 2009 From the European Patent Office Re.: Application No. 07700739.1.
Supplementary European Search Report and the European Search Opinion Dated Sep. 22, 2009 From the European Patent Office Re.: Application No. 07700738.3.
Barberi et al. "Derivation of Multipotent Mesenchymal Precursors From Human Embryonic Stem Cells", PLoS Medicine, XP002544487, 2(6):0554-0560, 2005.
Cao et al. "Osteogenic Differentiation Within Human Embryoid Bodies Result in a Marked Increase in Osteocalcin Secretion After 12 Days of In Vitro Culture, and Formation of Morphologically Distinct Nodule-Like Structures", Tissue and Cell, XP004965194, 37(4): 325-334, Aug. 2005. Abstract.
Olivier et al. "Differentiation of Human Embryonic Stem Cells Into Bipotent Mesenchymal Stem Cells", Stem Cells, XP009078939, 24(8): 1914-1922, Aug. 2006. Abstract.
Sottile et al. "In Vitro Osteogenic Differentiation of Human ES Cells", Cloning and Stem Cells, XP009053197, 5(2): 149-155, 2003. Abstract.

(Continued)

*Primary Examiner* — Deborah Crouch

(57) ABSTRACT

Methods of generating and expanding proliferative, multipotent connective tissue progenitor cells from embryonic stem cells and embryoid bodies are provided. Also provided are methods of generating functional tendon grafts in vitro and bone, cartilage and connective tissues in vivo using the isolated cell preparation of connective tissue progenitor cells.

8 Claims, 40 Drawing Sheets
(36 of 40 Drawing Sheet(s) Filed in Color)

OTHER PUBLICATIONS

Official Action Dated Feb. 14, 2011 From the US Patent and Trademark Office Re. U.S. Appl. No. 12/087,664.
Response Dated Feb. 23, 2011 to Communication Pursuant to Article 94(3) EPC of Oct. 25, 2010 From the European Patent Office Re.: Application No. 07700739.1.
Haegel et al. "CD44 in Differentiated Embryonic Stem Cells: Surface Expression and Transcripts Encoding Multiple Variants", Developmental Immunology, 3(4): 239-246, 1994.
Massachusetts Human Stem Cell Bank "Human Embryonic Stem Cell (hESC) Assessment by Flow Cytometry Using Directly Conjugated Antibodies", Massachusetts Human Stem Cell Bank, SOP-CH-001, p. 92-96, Feb. 24, 2009.
Communication Pursuant to Article 94(3) EPC Dated Dec. 16, 2009 From the European Patent Office Re.: Application No. 07700738.3.
Search Report and Written Opinion Dated Dec. 10, 2009 From the Intellectual Property Office of Singapore Issued by the Austrian Patent Office Re.: Application No. 200805148-4.
Response Dated Apr. 27, 2010 to Communication Pursuant to Article 94(3) EPC of Oct. 29, 2009 From the European Patent Office Re.: Application No. 07700739.1.
Galotto et al. "Stromal Damage as Consequence of High-Dose Chemo/Radiotherapy in Bone Marrow Transplant Recipients", Experimental Hematology, 27: 1460-1466, 1999.
Response Dated May 16, 2011 to Official Action of Feb. 14, 2011 From the US Patent and Trademark Office Re. U.S. Appl. No. 12/087,664.
Response Dated Jun. 7, 2010 to Search Report and Written Opinion of Dec. 10, 2009 From the Intellectual Property Office of Singapore Issued by the Austrian Patent Office Re.: Application No. 200805148-4.
Response Dated Jun. 13, 2010 to Communication Pursuant to Article 94(3) EPC of Dec. 16, 2009 From the European Patent Office Re.: Application No. 07700738.3.
Jaiswal et al. "Osteogenic Differentiation of Purified, Culture-Expanded Human Mesenchymal Stem Cells In Vitro", Journal of Cellular Biochemistry, 64: 295-312, 1997.
Marley et al. "Peripheral Blood Progenitor Cell Mobilisation Alters Myeloid, But Not Erythroid, Progenitor Cell Self-Renewal Kinetics", Bone Marrow Transplantation, 27: 241-248, 2001.
Robertson "NIH Sacrifices Commercial Rights in WiCell Deal", Nature Biotechnology, 19: 1001, Nov. 2001.
Official Action Dated Jun. 16, 2011 From the US Patent and Trademark Office Re. U.S. Appl. No. 12/087,664.
Official Action Dated Jul. 22, 2010 From the US Patent and Trademark Office Re. U.S. Appl. No. 12/087,664.
Peter et al. "Osteoblastic Phenotype of Rat Marrow Stromal Cells Cultured in the Presence of Dexamethasone, β-Glycerolphosphate, and L-Ascorbic Acid", Journal of Cellular Biochemistry, 71: 55-62, 1998.
Communication Pursuant to Article 94(3) EPC Dated Aug. 2, 2011 From the European Patent Office Re. Application No. 07700739.1.
Dominici et al. "Minimal Criteria for Defining Multipotent Mesenchymal Stromal Cells. The International Society for Cellular Therapy Position Statement", Cytotherapy, 8(4): 315-317, 2006.
Office Action Dated Aug. 8, 2010 From the Israel Patent Office Re. Application No. 192709 and Its Translation Into English.
Office Action Dated Aug. 8, 2010 From the Israel Patent Office Re. Application No. 192710 and Its Translation Into English.
Response Dated Sep. 15, 2011 to Official Action of Jun. 16, 2011 From the US Patent and Trademark Office Re. U.S. Appl. No. 12/087,664.
Communication Pursuant to Article 94(3) EPC Dated Oct. 11, 2011 From the European Patent Office Re.: Application No. 07700738.3.
Written Opinion Dated Aug. 12, 2008 From the International Searching Authority Re.: Application No. PCT/IL07/00046.
Campagnoli et al. "Identification of Mesenchymal Stem/Progenitor Cells in Human First-Trimester Fetal Blood, Liver, and Bone Marrow", Blood, 98(8): 2396-2402, Oct. 15, 2001. Abstract, p. 2397, r-h Col., § 3,1-h Col., § 1, 3, p. 2398, r-h Col., § 3, p. 2399, Fig.2, p. 2400, Fig.5.
Coelho et al. "Human Bone Cell Cultures in Biocompatibility Testing. Part II: Effect of Ascorbic Acid, β-Glycerophosphate and Dexamethasone on Osteoblastic Differentiation", Biomaterials, 21(11): 1095-1102, Jun. 2000.
Heng et al. "Directing Stem Differentiation Into the Chondrogenic Lineage In Vitro", Stem Cells, XP002534527, 22(7): 1152-1167, 2004.
Pittenger et al. "Multilineage Potential of Adult Human Mesenchymal Stem Cells", Science, 284: 143-147, Apr. 2, 1999. p. 143, r-h Col., § 2.
Supplementary European Search Report and the European Search Opinion Dated Jul. 10, 2009 From the European Patent Office Re.: Application No. 07700739.1.
Banfi et al. "Proliferation Kinetics and Differentiation Potential of Ex Vivo Expanded Human Bone Marrow Stromal Cells: Implications for Their Use in Cell Therapy", Experimental Hematology, XP002441523, 28(6): 707-715, Jun. 2000. Abstract, p. 708-709.
Caplan "Mesenchymal Stem Cells: Cell-Based Reconstructive Therapy in Orthopedics", Tissue Engineering, XP002534528, 11(7-8): 1198-1211, Jul. 2005.
Cohen et al. "Tissue Engineering Using Human Embryonic Stem Cell", Methods in Enzymology—Stem Cell Tools and Other Experimental Protocols, XP009118865, 420: 303-315, 2006.
Heng et al. "Directing Stem Differentiation Into the Chondrogenic Lineage In Vitro", Stem Cells, 22(7): 1152-1167, 2004.
Heng et al. "Strategies for Directing the Differentiation of Stem Cells Into the Osteogenic Lineage In Vitro", Journal of Bone and Mineral Research, XP002534526, 19(9): 1379-1394, Sep. 2004.
Im et al. "Do Adipose Tissue-Derived Mesenchymal Stem Cells Have the Same Osteogenic and Chondrogenic Potential as Bone Marrow-Derived Cells?", OsteoArthritis and Cartilage, XP005094309, 13(10): 845-853, Oct. 2005. Abstract.
Kelm et al. "Microscale Tissue Engineering Using Gravity-Enforced Cell Assembly", Trends in Biotechnology, XP004497323, 22(4): 195-202, Apr. 2004. Abstract.
Krampera et al. "Mesenchymal Stem Cells for Bone, Cartilage, Tendon and Skeletal Muscle Repair", Bone, XP025061266, 39(4): 678-683, Oct. 2006.
Marlovits et al. "Chondrogenesis of Aged Human Articular Cartilage in a Scaffold-Free Bioreactor", Tissue Engineering, XP002534525, 9(6): 1215-1226, Sep. 2003. Abstract.
Communication Pursuant to Article 94(3) EPC Dated Oct. 25, 2010 From the European Patent Office Re.: Application No. 07700739.1.
D'Ippolito et al. "Marrow-Isolated Adult Multilineage Inducible (MIAMI) Cells, A Unique Population of Postnatal Young and Old Human Cells With Extensive Expasion and Differentiation Potential", Journal of Cell Science, XP002559663, 117: 2971-2981, Jun. 15, 2004.
Jiang et al. "Pluripotency of Mesenchymal Stem Cells Derived From Adult Marrow", Nature, XP002559664, 418: 41-49, Jul. 4, 2002.
Official Action Dated Sep. 30, 2010 From the US Patent and Trademark Office Re. U.S. Appl. No. 12/087,664.
Chan et al. "Human Fetal Mesenchymal Stem Cells as Vehicles for Gene Delivery", Stem Cells, 23: 93-102, 2005.
Kuznetsov et al. "Effect of Serum on Human Bone Marrow Stromal Cells: Ex Vivo Expansion and In Vivo Bone Formation", Transplantation, 70(12): 1780-1787, Dec. 27, 2000.
McBeath et al. "Cell Shape, Cytoskeletal Tension, and RhoA Regulate Stem Lineage Commitment", Development Cell, 6: 483-495, Apr. 2004.
Muraglia et al. "Clonal Mesenchymal Progenitors From Human Bone Marrow Differentiate In Vitro According to A Hierarchical Model", Journal of Cell Science, 113: 1161-1166, 2000.
Response Dated Dec. 27, 2010 to Search Report and Written Opinion of Aug. 2, 2010 From the Intellectual Property Office of Singapore Re. Application No. 200805146-8.
Response Dated Dec. 29, 2010 to Official Action of Sep. 30, 2010 From the US Patent and Trademark Office Re. U.S. Appl. No. 12/087,664.
Communication Pursuant to Article 94(3) EPC Dated Nov. 26, 2010 From the European Patent Office Re.: Application No. 07700738.3.
Response Dated Dec. 8, 2010 to Office Action of Aug. 8, 2010 From the Israel Patent Office Re. Application No. 192709.
Response Dated Dec. 8, 2010 to Office Action of Aug. 8, 2010 From the Israel Patent Office Re. Application No. 192710.

Tsai et al. "Isolation of Human Multipotent Mesenchymal Stem Cells From Second-Trimester Amniotic Fluid Using a Novel Two-Stage Culture Protocol", Human Reproduction, 19(6): 1450-1456, 2004.
Official Action Dated Nov. 23, 2011 From the US Patent and Trademark Office Re. U.S. Appl. No. 12/087,664.

Notice of Allowance Dated Feb. 17, 2012 From the US Patent and Trademark Office Re. U.S. Appl. No. 12/087,664.

* cited by examiner

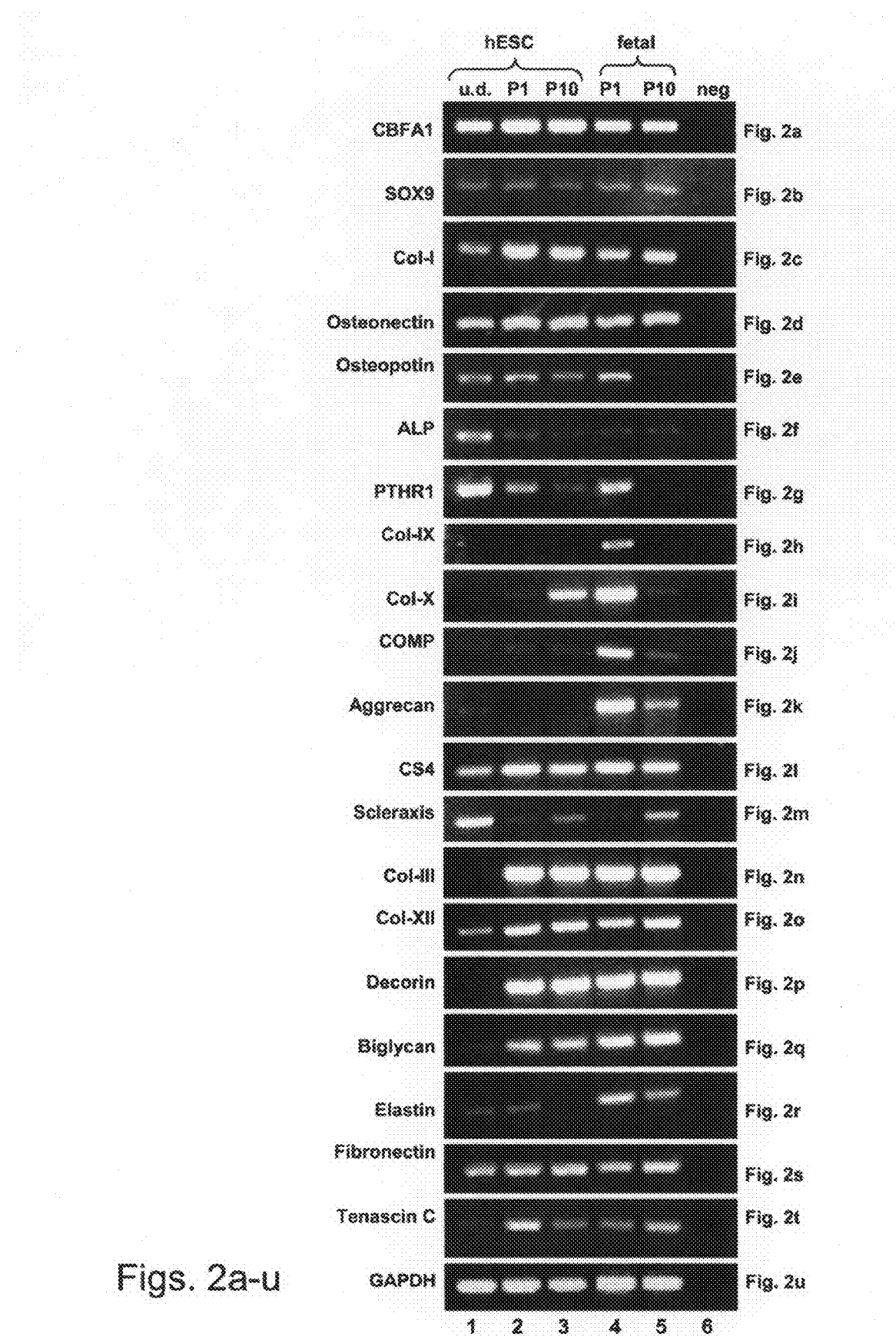
Figs. 2a-u

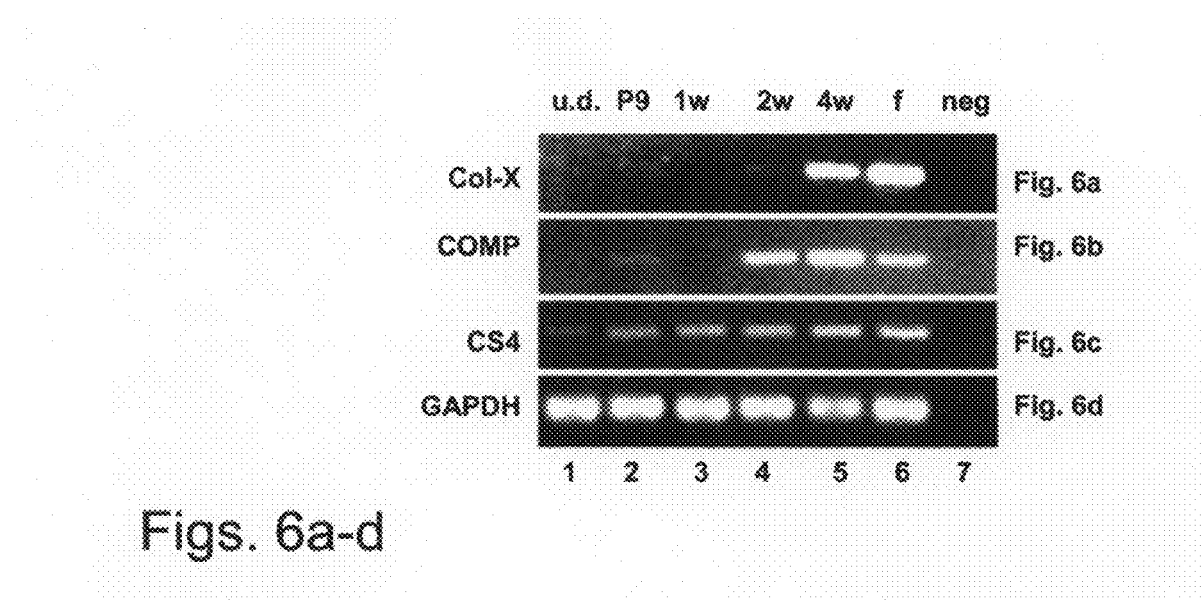
Figs. 6a-d

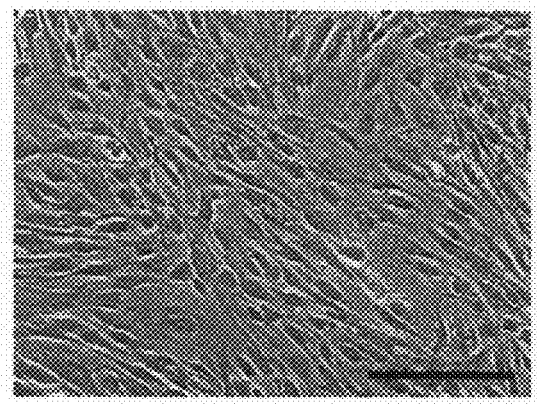 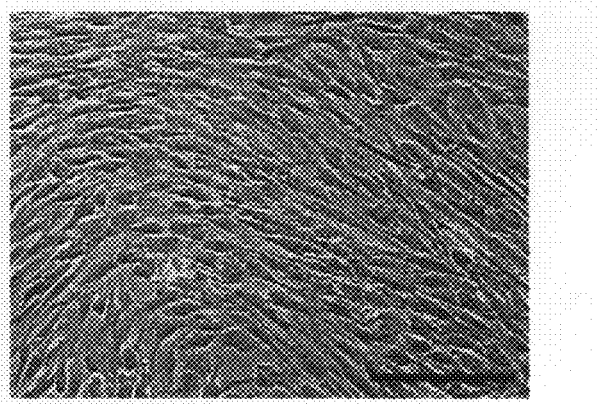
Fig. 27a                    Fig. 27b

HUMAN EMBRYONIC STEM CELL-DERIVED CONNECTIVE TISSUE PROGENITORS FOR TISSUE ENGINEERING

RELATED APPLICATIONS

This Application is a National Phase of PCT Patent Application No. PCT/IL2007/000046 having International filing date of Jan. 11, 2007, which claims the benefit of U.S. Provisional Patent Application Nos. 60/861,081 filed on Nov. 27, 2006; 60/861,080 filed on Nov. 27, 2006; and 60/757,864 filed on Jan. 11, 2006. The contents of the above Applications are all incorporated herein by reference.

FIELD AND BACKGROUND OF THE INVENTION

The present invention relates to methods of generating and isolating proliferative, non terminally differentiated connective tissue progenitor cells from embryonic stem cells and embryoid bodies and, more particularly, to methods of using such cells for cell based therapy and tissue engineering applications.

Cell-based tissue engineering is an evolving interdisciplinary area that offers new opportunities for clinical applications, creating a tool for repairing and replacing damaged or lost tissues with biological substitutes. The shortage of organ transplants and the exceeding number of patients on waiting lists greatly encourage the development of this field. The fundamentals of tissue engineering combine cells, bioactive matrices and chemically and biophysically defined in-vitro culture conditions. For tissue engineering, cells must be easily isolated, sufficient in numbers, with a great proliferation capacity and a well-defined differentiation potential. A number of cell sources have been suggested including primary cells and stem cells which are either host- or donor-derived. A wide array of matrices, either biologically or synthetically designed, are to provide the mechanical cues and three-dimensional environment, supporting cell attachment, migration, proliferation, differentiation and organization into complex tissues. Controlling stem cell proliferation and differentiation into any desired cell type requires the identification of chemicals (e.g., hormones and growth factors) and/or growth conditions (e.g., static or dynamic culturing conditions), which regulate the differentiation into the desired cell or tissue.

Connective tissue repair and regeneration are subjected to intensive research within clinical medicine. Damaged or disordered connective tissues, such as bone, cartilage and tendons need to be reconstructed or replaced due to traumatic injuries, degenerative diseases, tumor resections and congenital malformations. Current strategies in reconstructive orthopedic surgery include the use of autografts, allografts and artificial substitutes, all subjected to various limitations. While the use of cell grafts is limited by availability and morbidity, synthetic grafts are osteoconductively inferior to their biological counterparts, and could fail.

Mesenchymal stem cells (MSCs) have previously been derived from bone (Sottile, V et al 2002), bone marrow (Pittenger, M. F et al, 1999), muscle (Mastrogiacomo, M et al 2005), and fat (Zuk, P. A et al, 2001), and were capable of differentiating into adipocytic, chondrocytic, osteocytic or myogenic lineages.

Human embryonic stem cells (hESCs) hold great promise as a source of cells for tissue engineering. Their ability for practically unlimited self-renewal can potentially provide the required amount of cells needed for ex vivo tissue construction. In addition, they are characterized by a developmental potential to differentiate into any cell type of the mammalian embryo, and recently have been efficiently derived by means of somatic cell nuclear transfer, creating patient-specific immune-matched cell lines. hESCs have been shown to be able to form vascularized tissue-like structures when grown on either PLGA/PLLA or alginate porous scaffolds.

Several approaches have been recently described for isolating MSC-like cells from hESCs.

For example, Olivier E N., et al., 2006 [Olivier, E. N., et al., 2006, Stem Cells 24, 1914-1922] cultured spontaneously differentiating cells of hESCs colonies which were scraped from the edges of the colonies ("raclures") until a thick multi-layer epithelium was formed (at least 4 weeks). The cells of the thick epithelium were further dissociated and routinely passaged. The resulting cells exhibited surface phenotype of MSCs such as CD105+/CD166+/HLA-ABC+/CD73+/CD45−/HLA-DR− and were capable of in-vitro differentiation into osteoblasts and adipocytes. However, the use of such a method (the "raclure method") is limited because specific ESCs are mechanically scraped from ESC colonies cultured on mouse feeder cells, which may result in a crude, non-defined, population of cells.

In another study Barberi, T., et al. (2005) co-cultured hESCs on mouse OP-9 stromal feeder layers and following 40 days of co-culture isolated CD73-positive cells (MSC-like cells) and replated them in the absence of the stromal cells. However, this method is limited by the extremely low yield of the MSC-like cells (only 5% of the cells were CD73-positive cells) and by the co-culturing of the hESCs on mouse feeder-layers, which complicates culturing procedures and limits the use for cell-based therapy.

Other approaches utilized ESCs which have undergone spontaneous differentiation to embryoid bodies (EBs) in order to generate in-vitro committed cells of the osteogenic lineage.

For example, EBs were dissociated into single cells and were further induced to terminally differentiate into the osteogenic lineage by culturing them in an osteogenic medium without passaging for 21 (Sottile V, et al., 2003) or 28 (Bielby et al., 2004) days. The resulting cells expressed osteogenic markers and formed mineralized nodules.

Other studies obtained committed cells of the osteogenic lineage by plating intact EBs on adherent culture plates and culturing the EBs for at least 22 days without passaging (Cao T., et al. 2005). Thus, Cao et al. (2005), Bielby et al. (2004) and Sottile et al. (2003) concluded that culturing cells of EBs in an osteogenic medium results in terminally differentiated cells of the osteoblast cell lineage.

There is thus a widely recognized need for, and it would be highly advantageous to have, hESC-derived multipotent cells for tissue engineering devoid of the above limitations.

SUMMARY OF THE INVENTION

According to one aspect of the present invention there is provided a method of generating connective tissue progenitor cells, the method comprising culturing embryoid bodies (EBs) in a culture medium under culturing conditions allowing differentiation of cells of the embryoid bodies into connective tissue progenitor cells, wherein the culturing conditions comprise passaging the connective tissue progenitor cells, whereas a first passage of the passaging is effected no more than 10 days following initial culturing of the cells of the embryoid bodies in the culture medium, thereby generating the connective tissue progenitor cells.

According to another aspect of the present invention there is provided a method of generating connective tissue progenitor cells, the method comprising culturing single embryonic stem cells (ESCs) in a culture medium under culturing conditions allowing differentiation of the single embryonic stem cells into connective tissue progenitor cells, wherein the culturing conditions comprise passaging of the connective tissue progenitor cells, whereas a first passage of the passaging is effected no more than 10 days following initial culturing of the single embryonic stem cells in the culture medium, thereby generating the connective tissue progenitor cells.

According to yet another aspect of the present invention there is provided a method of generating connective tissue progenitor cells, the method comprising culturing embryoid bodies (EBs) in a culture medium which comprises dexamethasone and/or ascorbic acid so as to obtain connective tissue progenitor cells; thereby generating the connective tissue progenitor cells.

According to still another aspect of the present invention there is provided a method of generating connective tissue progenitor cells, the method comprising culturing single embryonic stem cells (ESCs) in a culture medium which comprises dexamethasone and/or ascorbic acid so as to obtain connective tissue progenitor cells; thereby generating the connective tissue progenitor cells.

According to an additional aspect of the present invention there is provided an isolated cell preparation of connective tissue progenitor cells resultant of the method of the present invention.

According to yet an additional aspect of the present invention there is provided an isolated cell preparation comprising a first population of cells expressing CD105 and a second population of cells not expressing CD105, wherein a ratio between the first population of cells and the second population of cells is between about 0.6 to about 1.5.

According to still an additional aspect of the present invention there is provided a method of generating a tendon tissue, the method comprising culturing the connective tissue progenitor cells of the isolated cell preparation of cells of claims 20 and/or 21 in a culture medium which comprises ascorbic acid and/or dexamethasone under culture conditions devoid of a carrier, thereby generating the tendon tissue.

According to a further aspect of the present invention there is provided a method of forming an extracellular matrix (ECM), the method comprising culturing the connective tissue progenitor cells of the isolated cell preparation of cells of claims 20 and/or 21 in a culture medium which comprises ascorbic acid, thereby forming the ECM.

According to further features in preferred embodiments of the invention described below, the method further comprising passaging the connective tissue progenitor cells in a presence of the culture medium which comprises dexamethasone and/or ascorbic acid to thereby expand the connective tissue progenitor cells.

According to still further features in the described preferred embodiments the single ESCs are obtained by enzymatically and/or mechanically dissociating the embryonic stem cells.

According to still further features in the described preferred embodiments culturing is effected under feeder-free culturing conditions.

According to still further features in the described preferred embodiments the culture medium comprises dexamethasone and/or ascorbic acid.

According to still further features in the described preferred embodiments the culture medium further comprises inorganic phosphate.

According to still further features in the described preferred embodiments the culture medium further comprises serum or serum replacement.

According to still further features in the described preferred embodiments the EBs are of a human origin.

According to still further features in the described preferred embodiments the EBs are 5-22 days old.

According to still further features in the described preferred embodiments the ESCs are of a human origin.

According to still further features in the described preferred embodiments passaging is effected every 2-5 days.

According to still further features in the described preferred embodiments passaging is effected for at least 20 times.

According to still further features in the described preferred embodiments a first passage of the passaging is effected no more than 10 days following initial culturing of cells of the embryoid bodies or the single embryonic stem cells in the culture medium which comprises dexamethasone and/or ascorbic acid.

According to still further features in the described preferred embodiments culturing is effected under xeno-free conditions.

According to still further features in the described preferred embodiments passaging is effected under xeno-free conditions.

According to still further features in the described preferred embodiments passaging is effected under feeder-free culturing conditions.

According to still further features in the described preferred embodiments the connective tissue progenitor cells comprise a first population of cells expressing CD105 and a second population of cells not expressing CD105, wherein a ratio between the first population of cells and the second population of cells is between about 0.6 to about 1.5.

According to still further features in the described preferred embodiments the isolated cell preparation is devoid of feeder cells.

According to still further features in the described preferred embodiments the isolated cell preparation is xeno-free.

According to still further features in the described preferred embodiments the first population of cells express CD166.

According to still further features in the described preferred embodiments the isolated cell preparation express CD44, CD29, and HLA-ABC.

According to still further features in the described preferred embodiments the isolated cell preparation not express CD45 and HLA-DR.

According to still further features in the described preferred embodiments the cells are capable of being maintained in a proliferative, non terminally differentiated state for at least 20 passages in culture.

According to still further features in the described preferred embodiments the connective tissue progenitor cells are capable of differentiating into cells of a chondrogenic lineage, an osteogenic lineage, an adipocytic lineage and a tendon and ligament lineage.

According to still further features in the described preferred embodiments the connective tissue progenitor cells are capable of forming mineralized matrix.

According to still further features in the described preferred embodiments the connective tissue progenitor cells are capable of forming a bone tissue.

According to still further features in the described preferred embodiments the connective tissue progenitor cells are capable of forming an extracellular matrix (ECM).

According to still further features in the described preferred embodiments the connective tissue progenitor cells are capable of forming a tendon tissue.

According to still further features in the described preferred embodiments the connective tissue progenitor cells are capable of forming a ligament tissue.

According to still further features in the described preferred embodiments the connective tissue progenitor cells are capable of forming a cartilage tissue.

According to still further features in the described preferred embodiments the culture medium further comprises dexamethasone.

The present invention successfully addresses the shortcomings of the presently known configurations by providing methods of generating and using connective tissue progenitor cells from embryonic stem cells and embryoid bodies.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
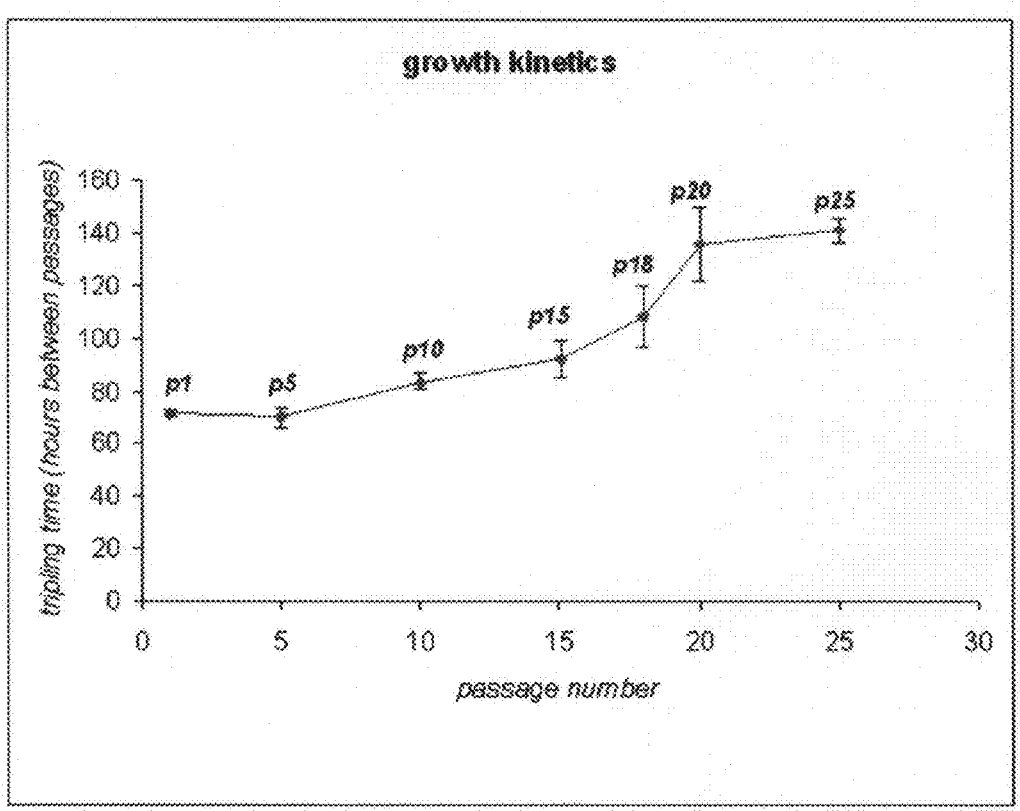
Figure 1B:
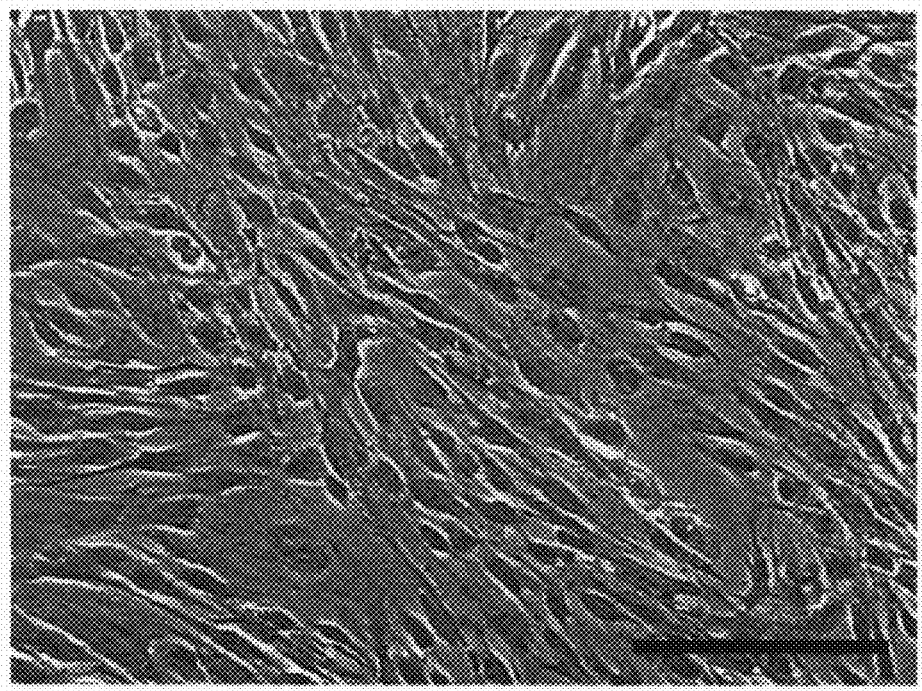
Figure 1C:
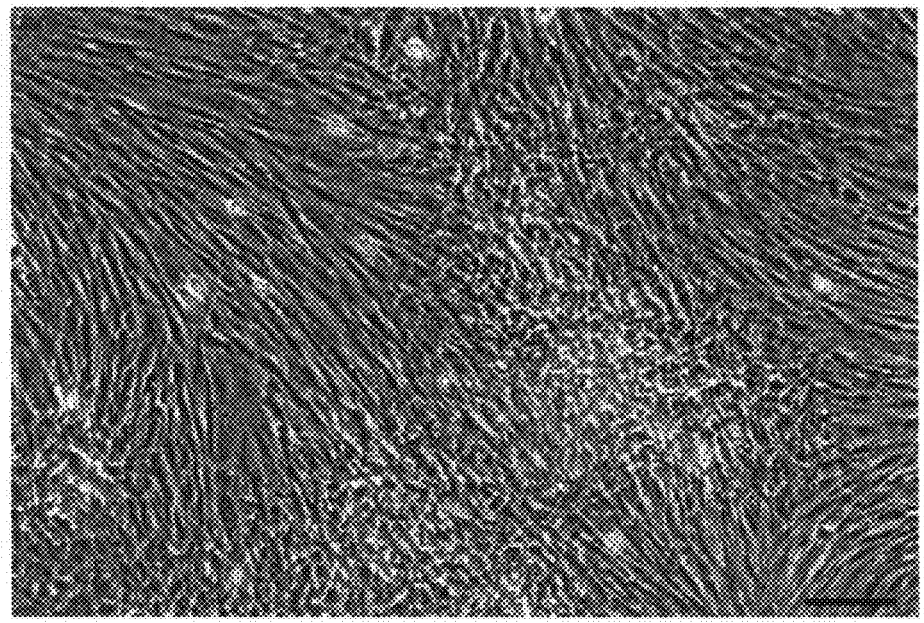

FIGS. 1a-c depict the characterization of the connective tissue progenitor cells (CTPs) of the present invention. FIG. 1a—Growth kinetics of CTPs. hESCs derived CTPs were continuously expanded in the presence of the CTP medium and splitted 1:3 in each cell passage every 3-5 days. Shown is the tripling time (i.e., the hours between passages in which the cell number was triplicated) as a function of the passage number. Note the decrease in proliferation rate towards passage 20-25 (i.e., the increase in the tripling time from about 80-100 hours between each cell passage to about 130 hours between each cell passage). The results shown are mean values (±SD) of three independent cultures. FIGS. 1b and c—Photomicrographs of hESC derived CTPs at passage 1 (FIG. 1b) show mesenchymal-cell morphology, with conversion to fibroblast-like morphology at passage 12 (FIG. 1c).

FIGS. 2a-u are RT-PCR analyses depicting the expression of markers characteristic of bone, cartilage, tendons and ligaments at passage 1 (p1) and passage 10 (p10) of both hESC-derived CTPs (lanes 2 and 3, respectively) and fetal-derived CTPs (lanes 4 and 5, respectively), compared to undifferentiated hESCs (u.d., lane 1) and negative (neg., lane 6) control. hESCs derived CTPs were cultured in CTP medium for 1 or 10 passages, following which RNA was prepared and RT-PCR reactions were performed using the PCR primers listed in Table 1 of the Examples section which follows. The tested markers were: CBFA1 (FIG. 2a), SOX9 (FIG. 2b), Col-I (Collagen type I, FIG. 2c), Osteonectin (FIG. 2d), Osteopontin (FIG. 2e), ALP (alkaline phosphatase, FIG. 2f), PTHR1 (FIG. 2g), Col-IX (Collagen type I, FIG. 2h), Col-X (Collagen type X; FIG. 2i), COMP (FIG. 2j), Aggrecan (FIG. 2k), CS4 (FIG. 2l), Scleraxis (FIG. 2m), Col-III (Collagen type III, FIG. 2n), Col-XII (Collagen type XII, FIG. 2o), Decorin (FIG. 2p), Biglycan (FIG. 2q), Elastin (FIG. 2r), Fibronectin (FIG. 2s), Tenascin C (FIG. 2t) and GAPDH (FIG. 2u). Note that both hESC-derived CTPs and human fetal-derived CTPs express high levels of core binding factor alpha 1 (CBFA1; FIG. 2a) and SOX9 (FIG. 2b), both are early transcription factors known to play a major role in osteoblast and chondrocyte differentiation. Also note that type I collagen (Col-I, FIG. 2c), the most abundant extracellular protein which is synthesized by osteoblasts, osteonectin (FIG. 2d) and osteopontin (FIG. 2e), two major non-collagenous bone matrix proteins, parathyroid hormone receptor 1 (PTHR1; FIG. 2g, mainly at passage 1), which regulates mineral homeostasis and bone formation, and bone-specific alkaline phosphatase (ALP; FIG. 2f), which binds phosphor to calcium and forms bone hydroxyapatite, are all detected at low and high passages, indicating osteogenic potential. CTPs were also positive for cartilage matrix markers: chondroitin sulfate proteoglycan 4 (CS4; FIG. 2k), a cartilage matrix proteoglycan, type X collagen (FIG. 2i, mainly hESCs-derived CTP at passage 10 and fetal derived CTPs are passage 1), which is a non-fibril-forming collagen restricted to the hypertrophic, calcifying zone of growth plate cartilage, and cartilage oligomeric matrix protein (COMP; FIG. 2h, mainly fetal derived CTPs at passage 1), a key non-collagenous cartilage matrix protein. In addition, note the expression of tendon and ligament specific markers, such as scleraxis (FIG. 2l, mainly at passage 10), a transcription factor expressed both in their mature and early progenitor populations, and other ECM-related proteins, including type III (Col-III; FIG. 2m) and type XII (Col-XII; FIG. 2n) collagens, decorin (FIG. 2o), biglycan (FIG. 2p), elastin (FIG. 2q), fibronectin (FIG. 2r), and tenascin-C (FIG. 2s), were detected. While elastin and tenascin-C were down-regulated at higher passages, scleraxis was clearly up-regulated.

Figure 3A:
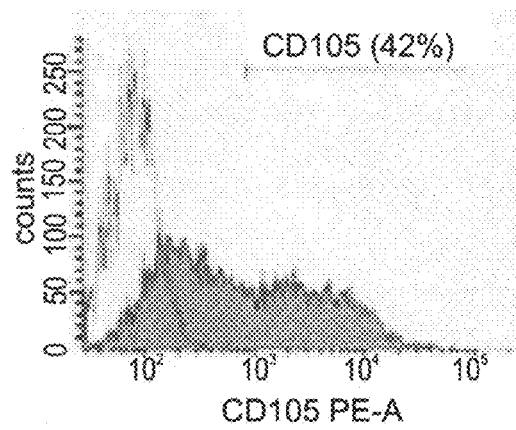
Figure 3B:
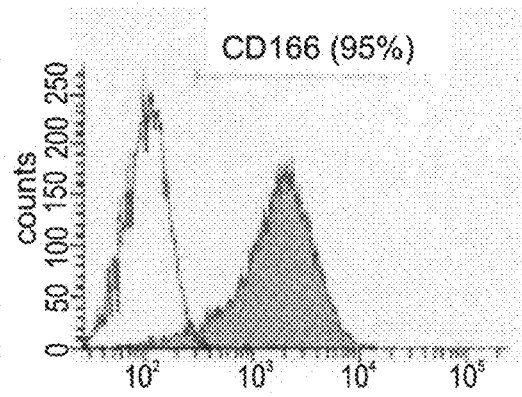
Figure 3C:
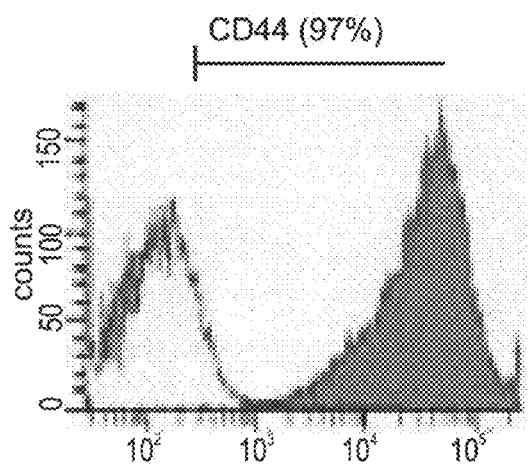
Figure 3D:
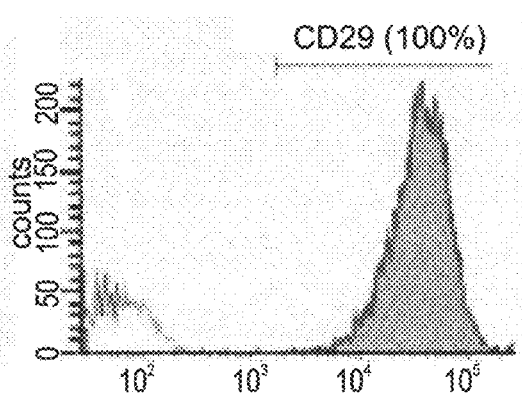
Figure 3E:
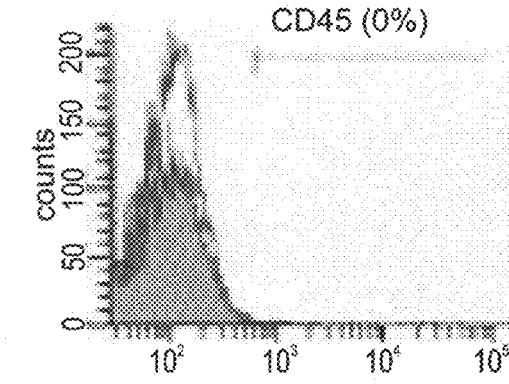
Figure 3F:
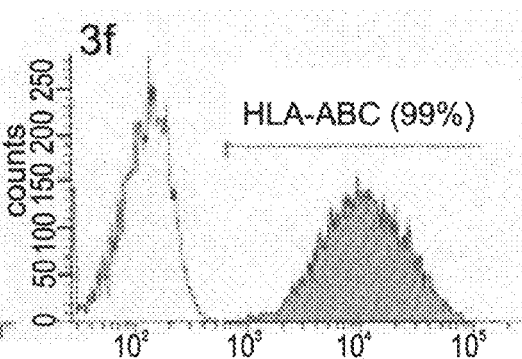
Figure 3G:
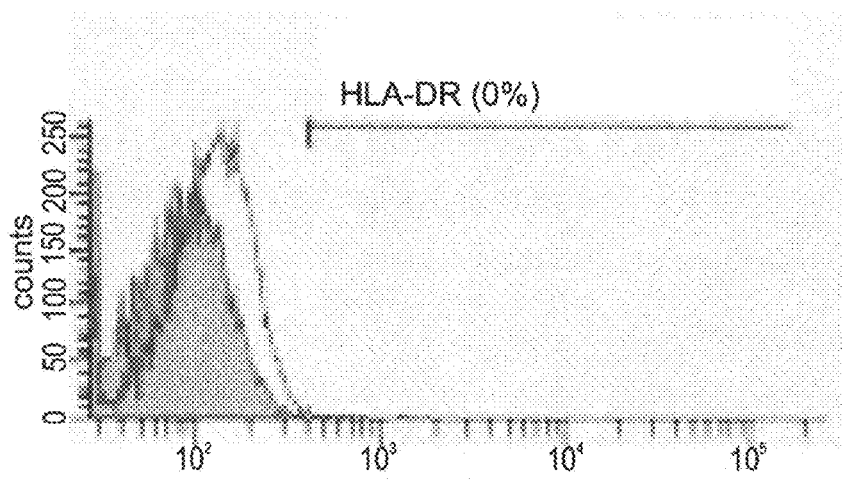
Figure 3H:
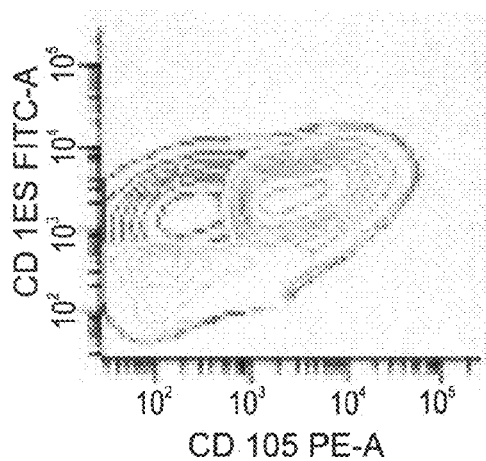
Figure 3I:
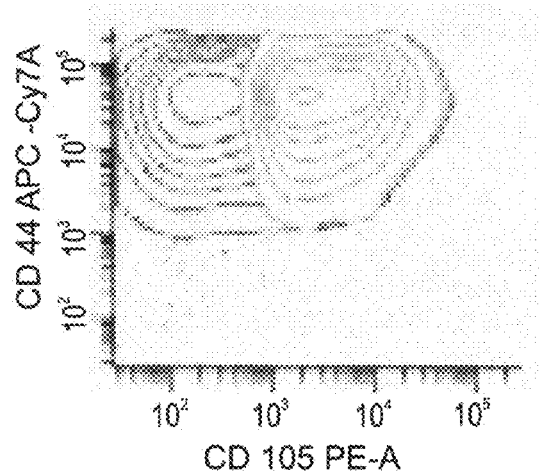
Figure 3J:
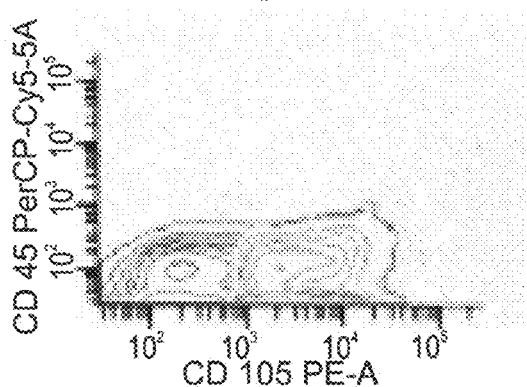
Figure 3K:
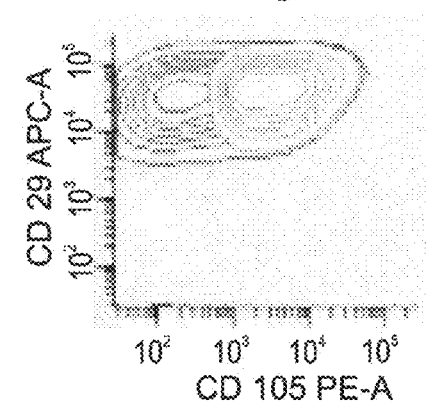

FIGS. 3a-k are FACS analyses of hESC-derived CTPs showing relatively high level of population purity with surface markers characteristic of MSCs. hESCs derived CTPs were cultured in CTP medium for 6-12 passages and were subjected to FACS analysis using antibodies specific to CD105 (eBioscience, San Diego, Calif., Cat. No. 12-1057-73) (FIG. 3a), CD166 (Serotec, Raleigh, N.C., USA, Cat. No. MCA1926F) (FIG. 3b), CD44 (eBioscience, Cat. No. 10-0441-81) (FIG. 3c), CD29 (Serotec, Cat. No. MCA1926F) (FIG. 3d), CD45 (Pharmingen, Cat. No. 345809) (FIG. 3e), HLA-ABC (eBioscience, Cat. No. 12-9983-71) (FIG. 3f), HLA-DR (eBioscience, Cat. No. 12-9956-71) (FIG. 3g). Note the positive expression of typical MSC surface markers, including CD105 (FIG. 3a), CD166 (FIG. 3b), CD44 (FIG. 3g) and CD29 (FIG. 3d), and the negative expression (absence) of CD45 (FIG. 3e), a hematopoietic marker. Level of cell purity was confirmed to be high, with two main sub-populations: CD105-positive (CD105-expressing, 42%) and CD105-negative (CD105-not expressing, 58%) (FIG. 3a) cells. Note that the CD105 positive cells are indeed positive for CD166 (FIG. 3h, green labeling), CD29 (FIG. 3k, green labeling), CD44 (FIG. 3i, green-labeling) and negative for CD45 (FIG. 3j, green labeling), while the CD105 negative portion is positive for CD29 (FIG. 3k, red labeling) and CD44 (FIG. 3i, red labeling), and includes the CD166 negative fraction (FIG. 3h, yellow labeling). Additionally, all cells were positive for HLA-ABC (FIG. 3f) and negative for HLA-DR (FIG. 3h, the major histocompatibility complex antigens).

Figure 4A:
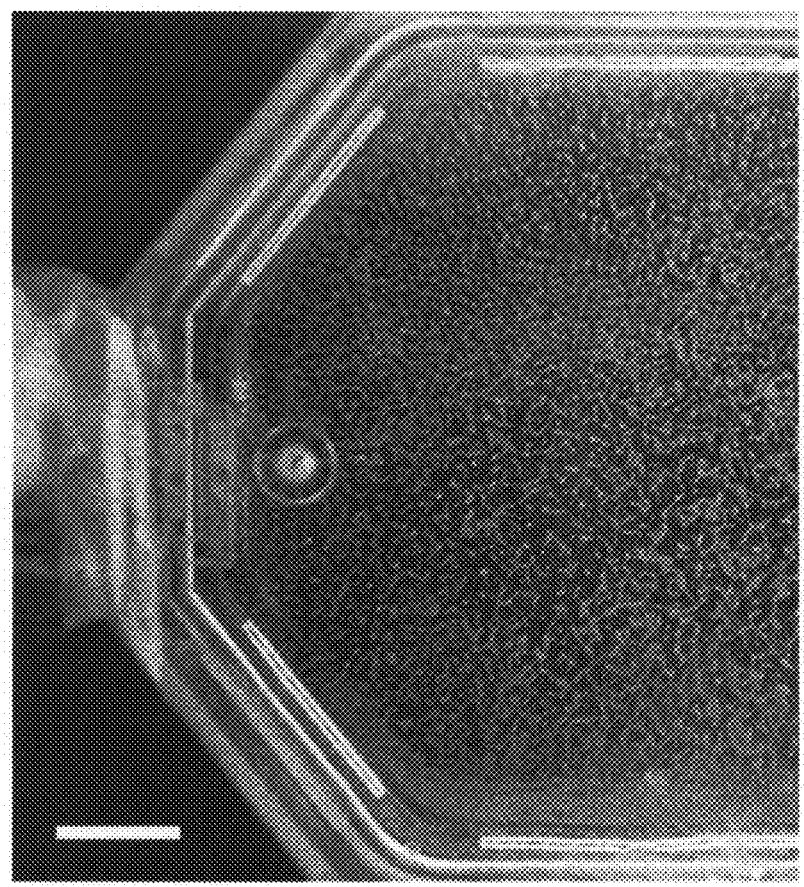
Figure 4B:
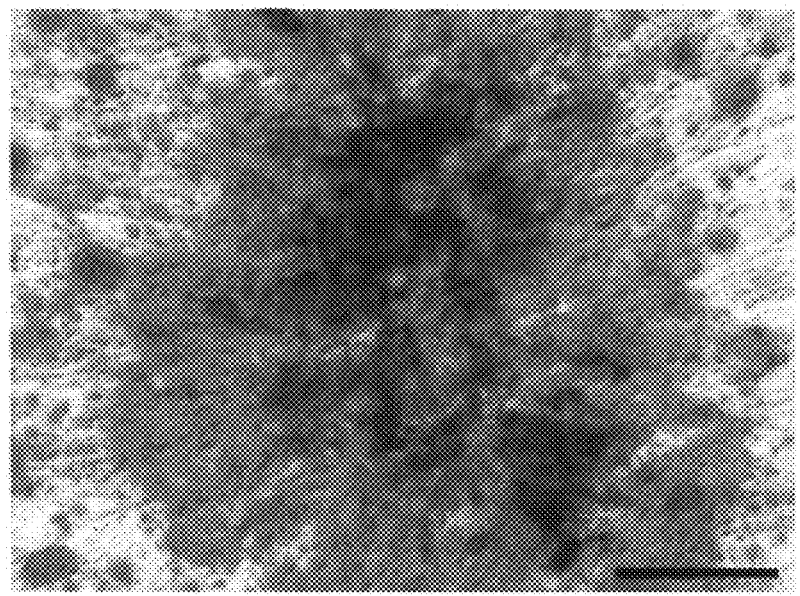
Figure 4C:
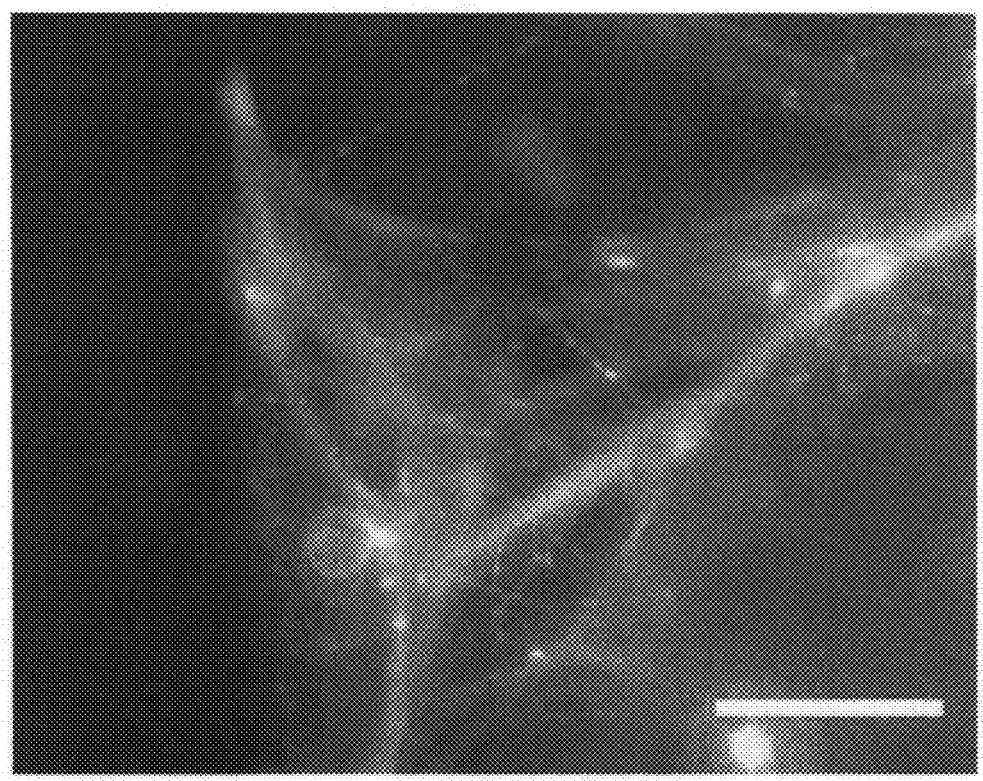
Figure 4D:
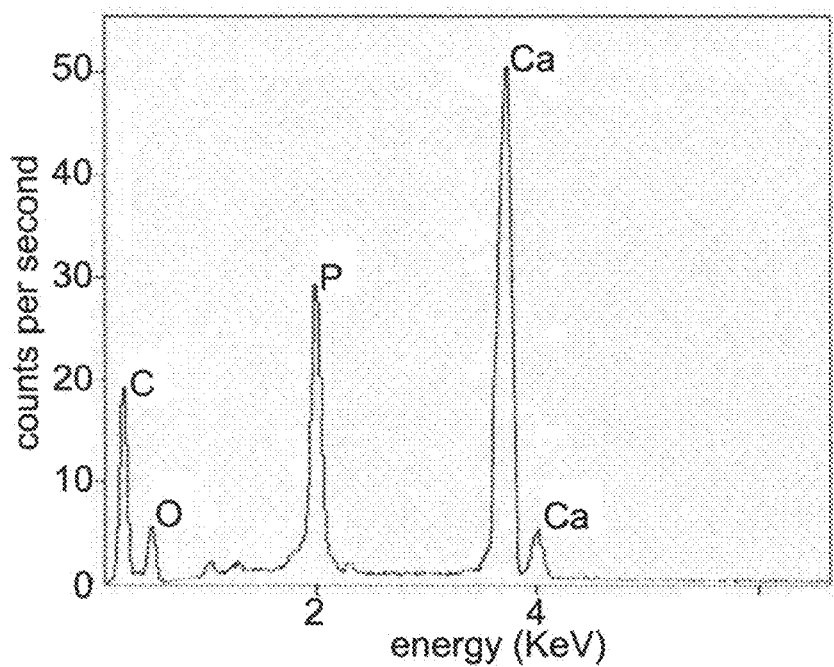
Figure 4E:
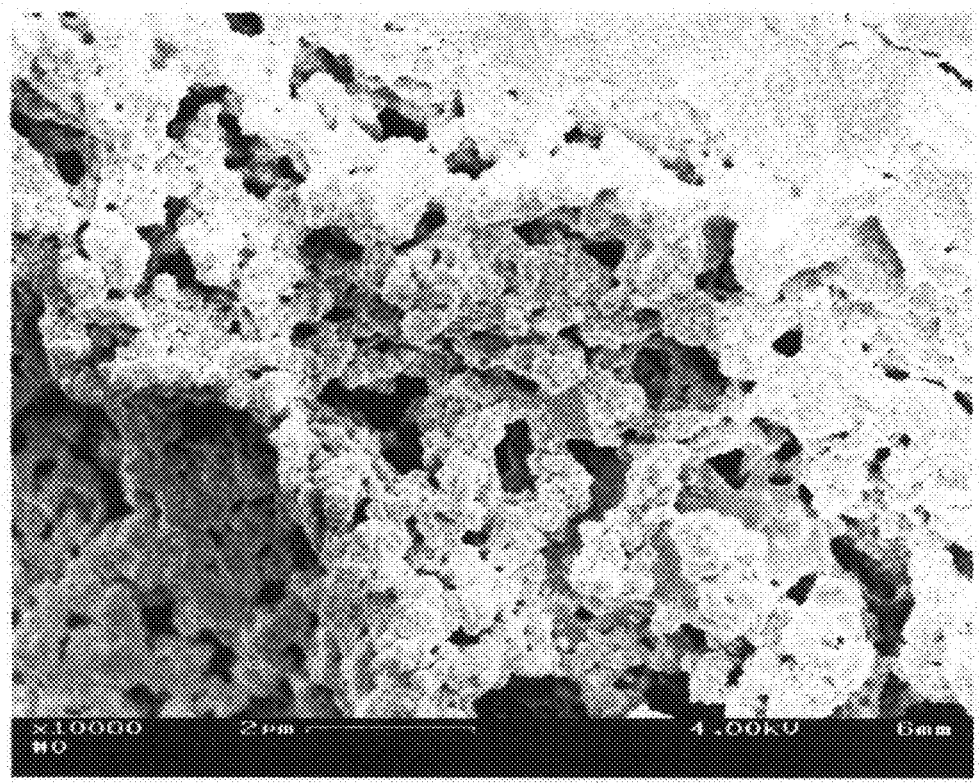

FIGS. 4a-e depict the differentiation potential of hESCs derived CTPs to the osteogenic lineage. hESCs—derived CTPs (taken from any passage of passages 1-25) were cultured in CTP medium supplemented with 10 mM beta-glycerophosphate (inorganic phosphate) for 1-4 weeks without culture splitting and were subjected to differentiation assays of the osteogenic lineage. FIG. 4a —A view of the macroscopic pattern of differentiated CTPs on a T75 (75 cm$^2$) tissue culture flask demonstrating bone mineralization. Scale bar—1 cm; FIG. 4b —Alizarin Red staining showing calcium deposits and bone nodule formation. Scale bar—100 µm; FIG. 4c —CTPs embedded in self-produced matrix expressing type I collagen (green). Nuclei were counterstained with DAPI (blue). Scale bar—100 µm; FIG. 4d —EDS analysis of bone mineralization, detecting calcium and phosphate as the most prominent signals, in addition to carbon and oxygen which could correspond to the presence of proteins. Note that the ratio between the calcium and phosphate corresponds to the expected ratio of the hydroxyapatite mineral; FIG. 4e —SEM image depicting mineralized matrix formed from the CTP culture. Magnification X 10,000, Scale bar—2 µm; Altogether, these experiments demonstrate the in-vitro osteogenic differentiation of hESCs derived CTPs to osteoblasts and the production of mineralized bone matrix.

Figure 5A:
Figure 5B:
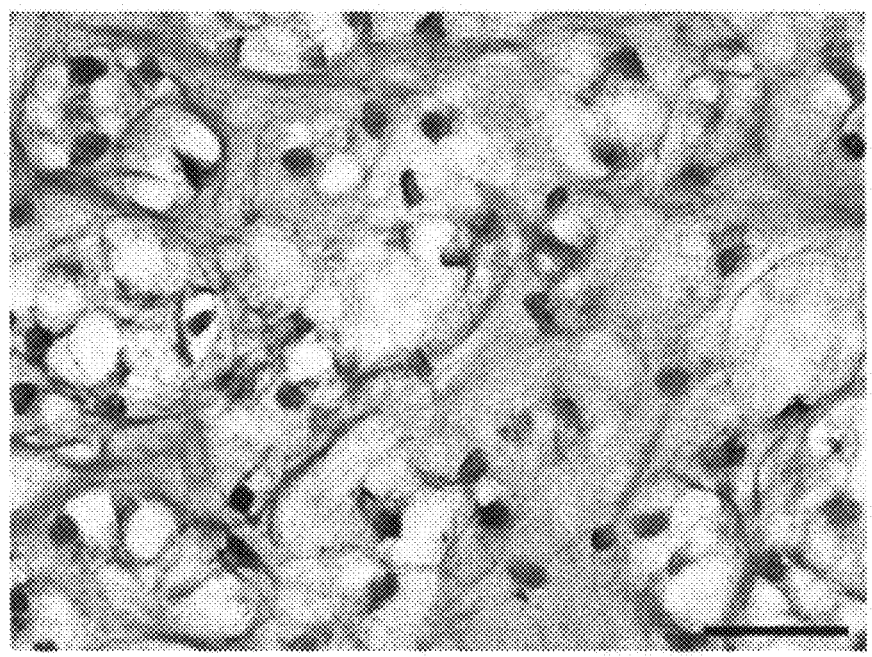
Figure 5C:
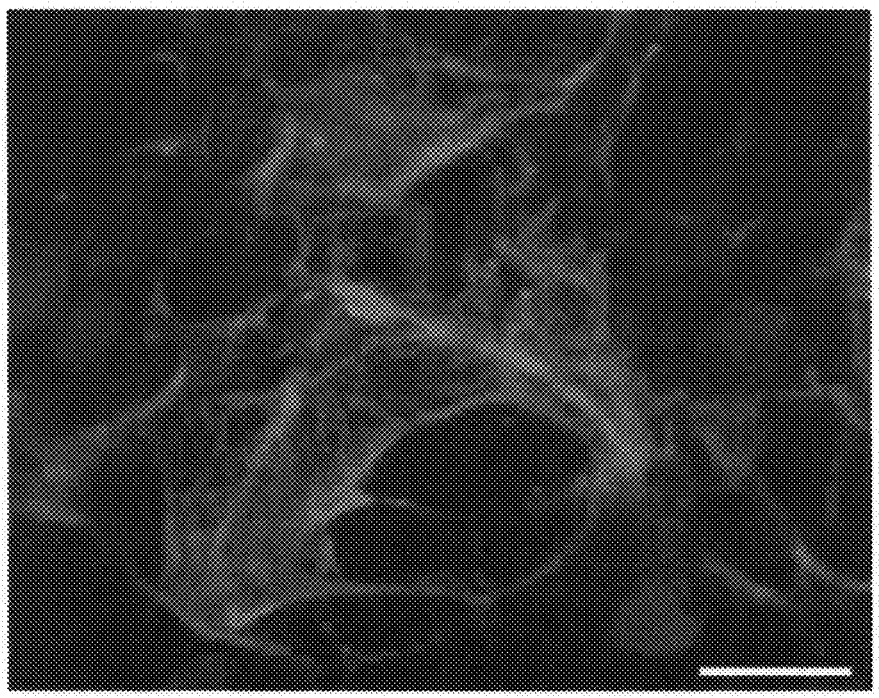
Figure 5D:
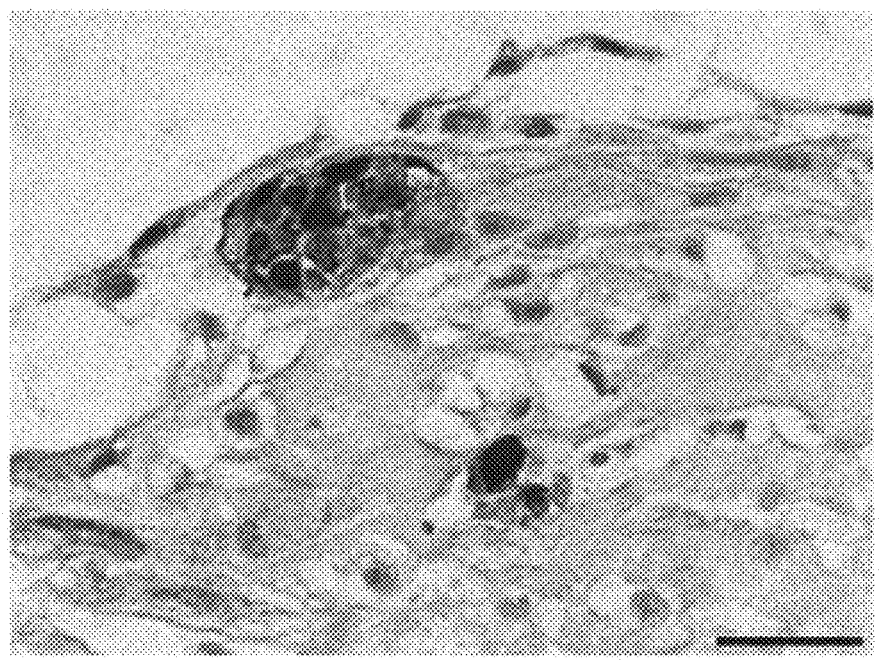

FIGS. 5a-d depict the in-vitro chondrogenic differentiation of the CTPs. hESCs derived CTPs (taken from any passage of 1-25 passages) were cultured in CTP medium for 10-14 days without culture splitting and were subjected to histological and immunostaining analyses. FIG. 5a—Histological examination of intact CTP cultures which were grown in suspension. The H&E staining showing round chondrocyte-like cells embedded in lacunae, at the viable periphery of the sample and morphological changes suggesting apoptosis occurring in the center of the tissue sample (asterisk), probably due to lack of nutrients and oxygen delivery in static culture conditions. Scale bar—100 µm; FIG. 5b—Picrosirius red staining detected collagenous matrix surrounding the cells. Scale bar—20 µm; FIG. 5c—ES-derived CTPs were cultured for 1-20 passages and were subjected to immunostaining analysis using anti type II collagen antibody (red; Chemicon, Cat. No. MAB8887) demonstrating fibrous ECM formation. Nuclei were counterstained with DAPI (blue). Scale bar—10 µm; FIG. 5d—Immunostaining with anti S-100 protein antibody (brown; DAKO Corp, Carpenteria, Calif., USA, Cat. No. Z0311) detecting small clusters of cells within the viable chondrocyte-like area. Scale bar—20 µm.

FIGS. 6a-d are RT-PCR analyses of hESC-derived CTP pellet cultures grown in the presence of low serum TGF-β3 supplemented medium. RT-PCR was performed using the PCR primers listed in Table 1 of the Examples section which follows, for the type X collagen (Col-X; FIG. 6a), COMP (FIG. 6d), CS4 (FIG. 6c) and GAPDH (FIG. 6d). Note the gradual up-regulation of selected cartilage markers (Col-X and COMP) by 1 week (1w, lane 3), 2 weeks (2w, lane 4) and 4 weeks (4w, lane 5) in pellet culture prepared from passage 9 CTPs, compared to undifferentiated hESCs (u.d., lane 1) or passage 9 (p9, lane 2) CTPs taken just before the pellet formation and differentiation induction to the chondrocyte lineage, early passage fetal-derived CTPs (f, lane 6) and negative control (neg., lane 7). Altogether, these experiments demonstrate the differentiation of hESCs derived CTPs to cells of the chondrogenic lineage (cartilage markers).

Figure 7A:
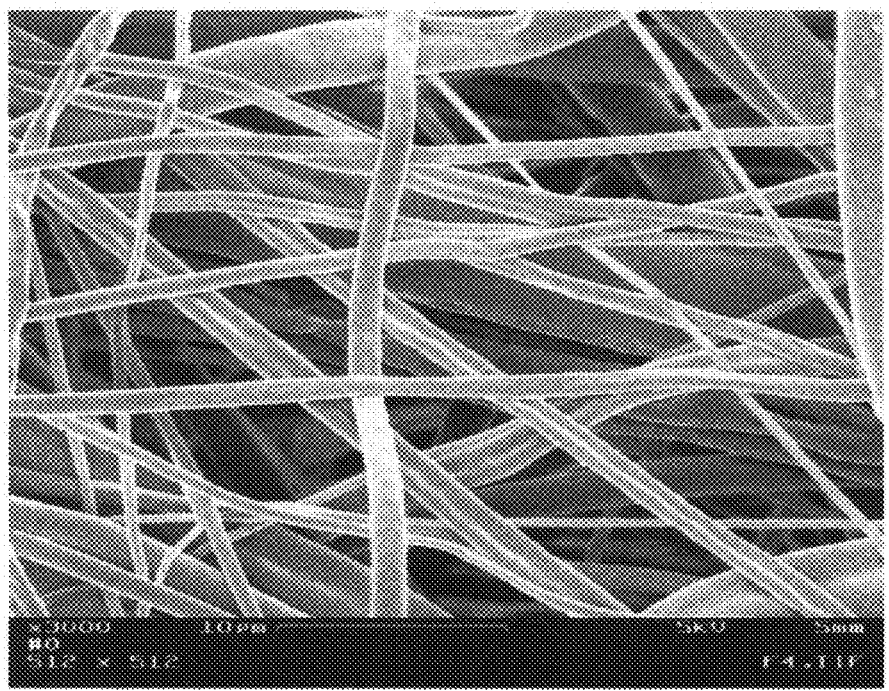
Figure 7B:
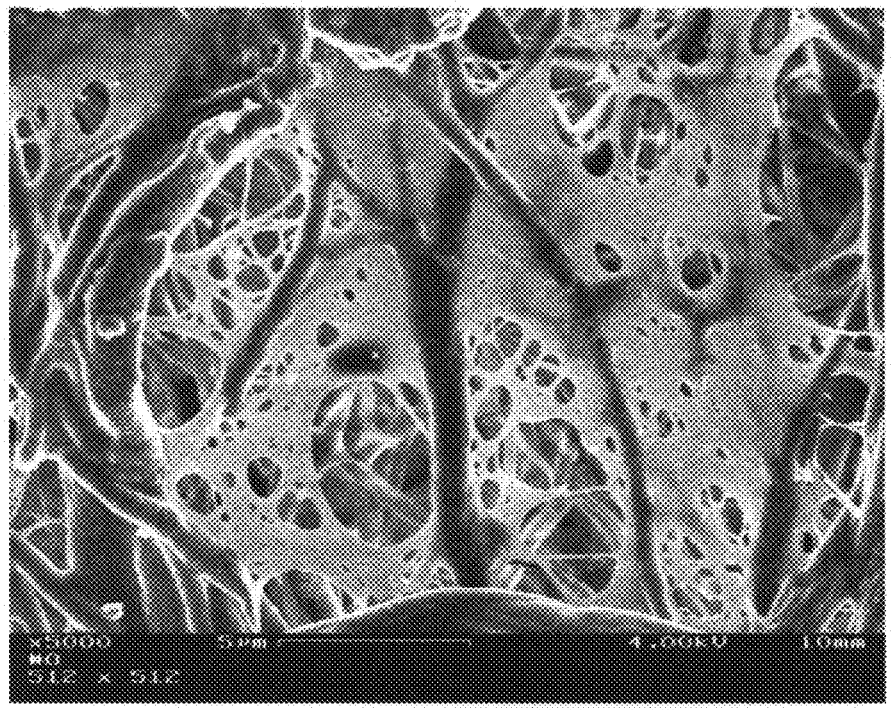
Figure 7C:
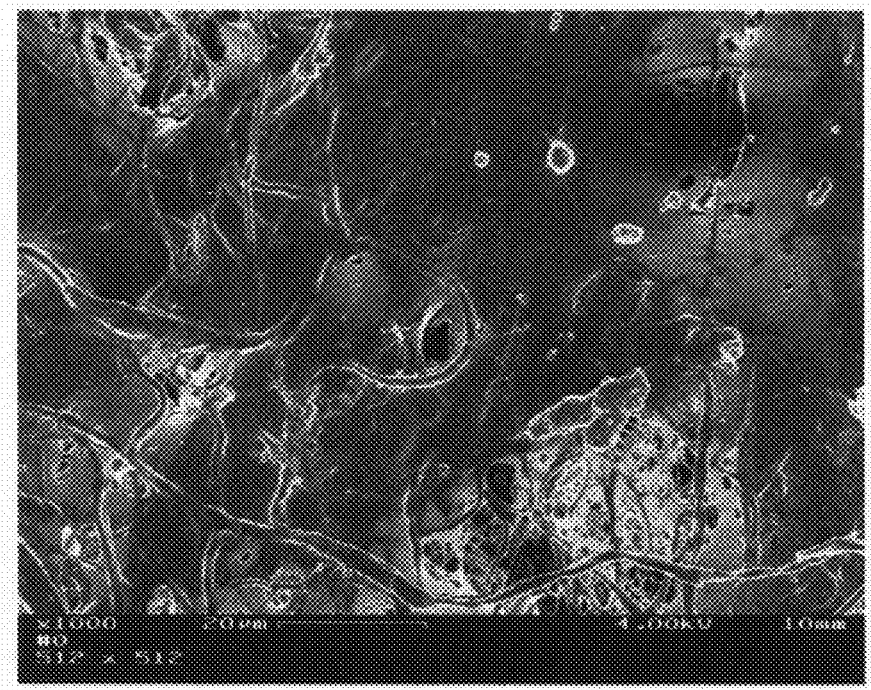
Figure 7D:
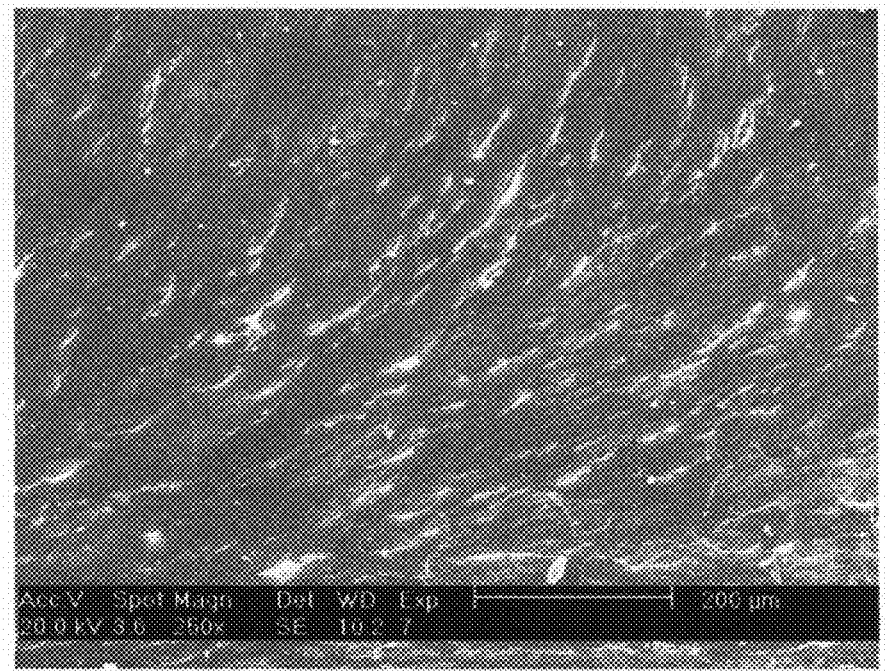
Figure 7E:
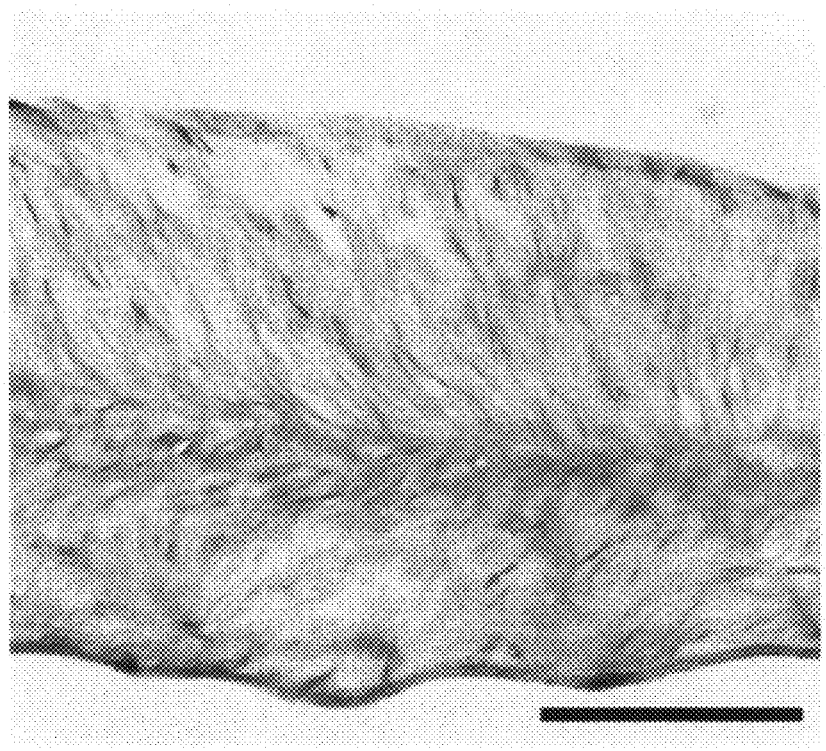
Figure 7F:
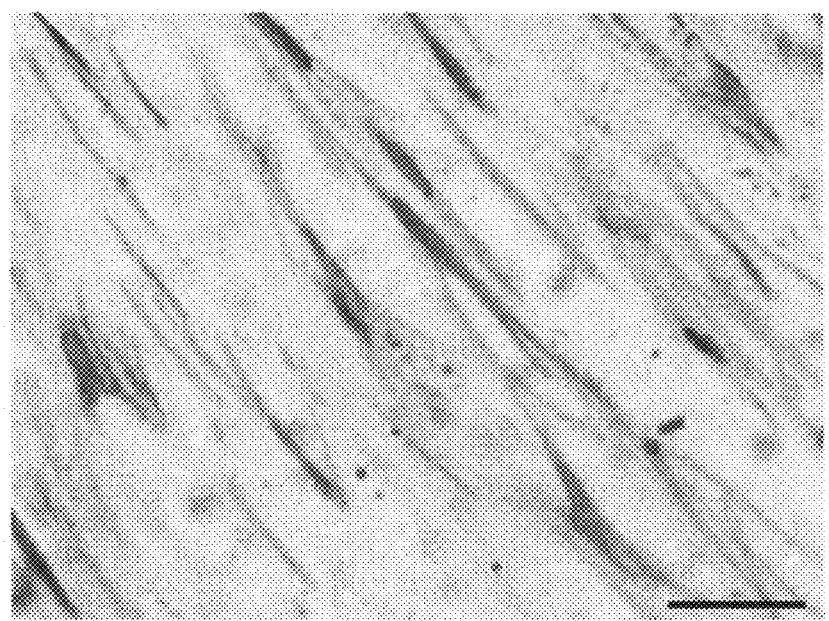

FIGS. 7a-f depict the differentiation of hESCs derived CTPs into a connective tissue. FIG. 7a—SEM image of the PCL/PLA electrospun nanofiber scaffold used for plating the CTPs (without the cells), demonstrating nano-scale, randomly orientated fibers. FIGS. 7b-d—SEM images of the electrospun nanofiber scaffolds seeded with CTPs at passage 10-12 demonstrating different stages in connective tissue formation. Note the beginning of extracellular matrix (ECM) formation following about 7 days (FIG. 7b; magnification X5000, scale bar—5 µm), the formation of intermediate tissue like patches following about 14 days (FIG. 7c; magnification X1000, scale bar—20 µm) and the firm 3D sheet-like tissue which completely covers the scaffold following about 4 weeks (FIG. 7d; magnification X250, scale bar—200 µm). FIGS. 7e-f—Cross sectional histological examination of sheet-like tissue with picro-sirius red (FIG. 7e, scale bar—100 µm) and H&E (FIG. 7f, scale bar—20 µm) staining showing extracellular collagen formation and mesenchymal-like cells aligned in parallel, embedded in extensive ECM.

Figure 8A:
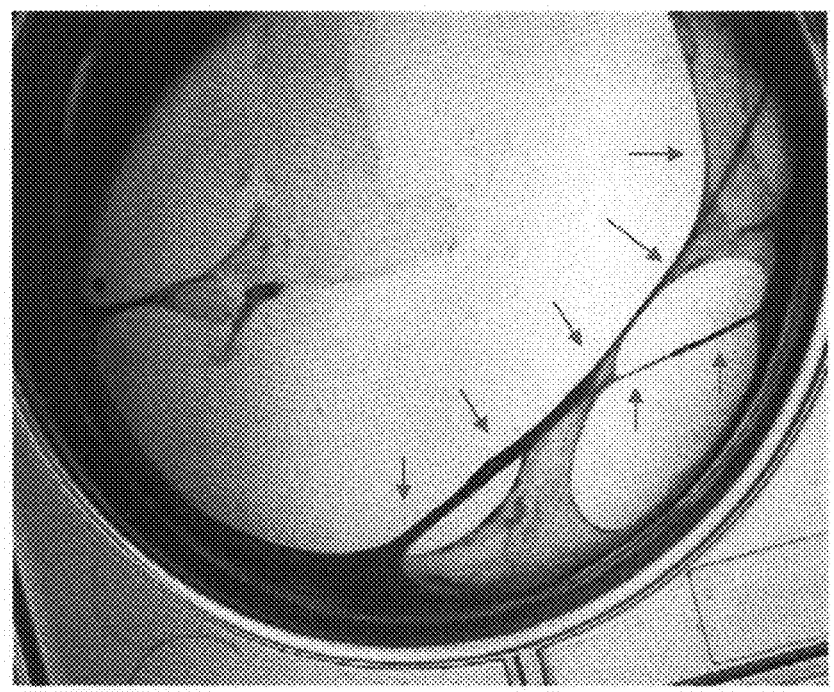
Figure 8B:
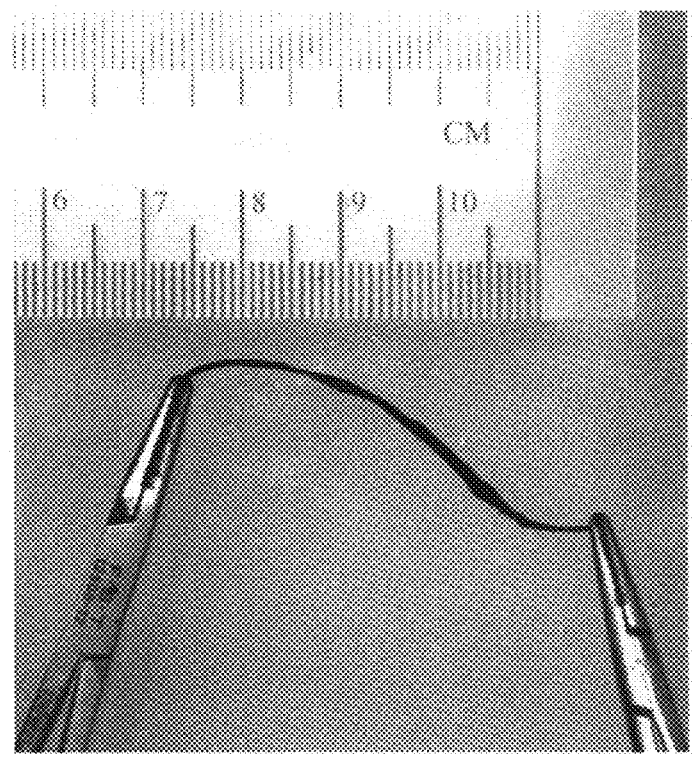

FIGS. 8a-b depict in vitro tendon formation from hESCs derived CTPs. CTPs were cultured in CTP medium for 8 weeks (FIG. 8a) and 4 months (FIG. 8b) without cell splitting. FIG. 8a—Macroscopic view of 8-week old hESC-derived construct (arrows) growing in a culture well of 6-well plate; FIG. 8b—a macroscopic view of a tendon which grew up to 5 centimeters following 4 months in culture.

Figure 9A:
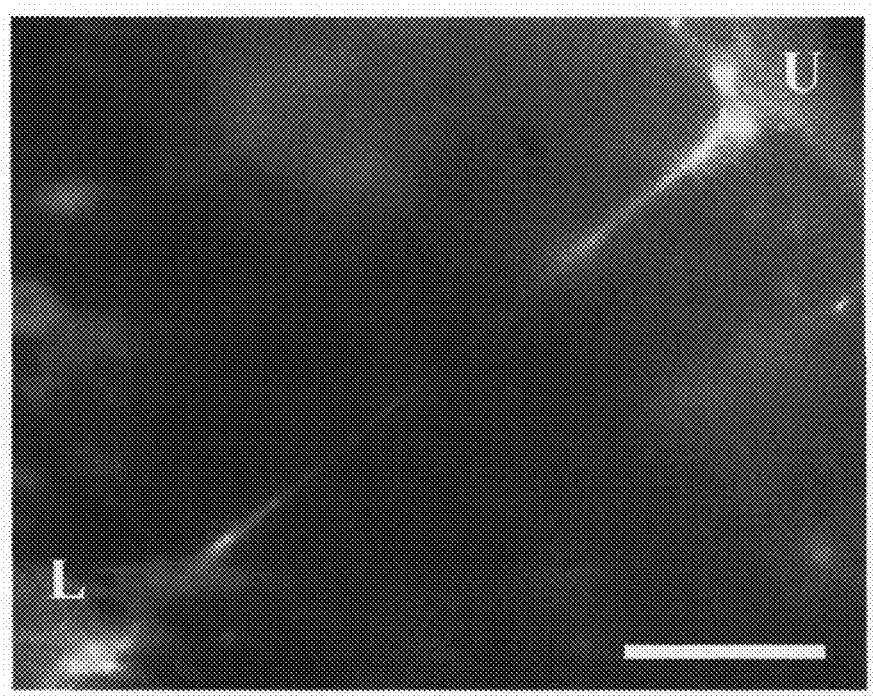
Figure 9B:
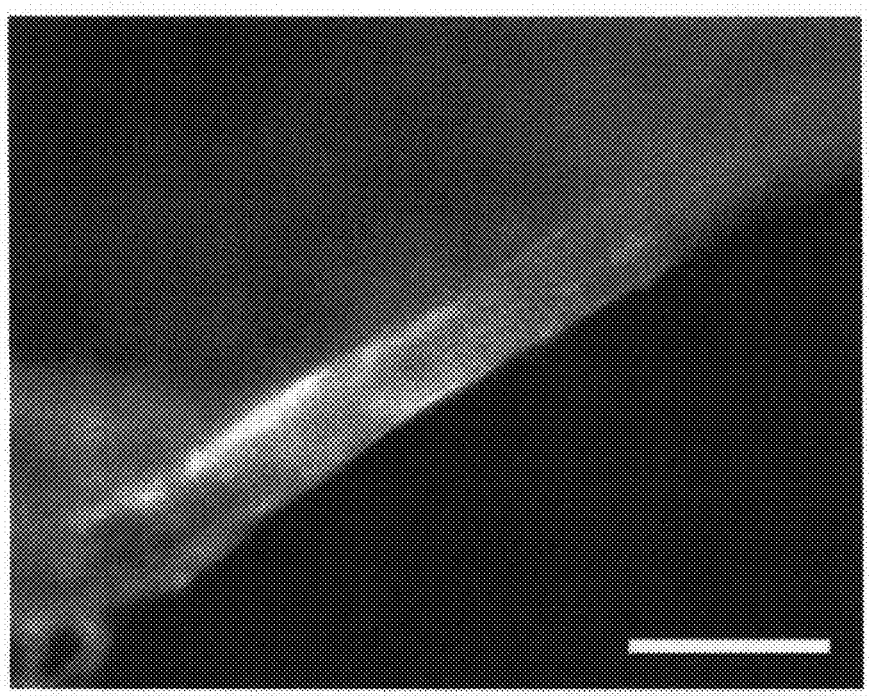
Figure 9C:
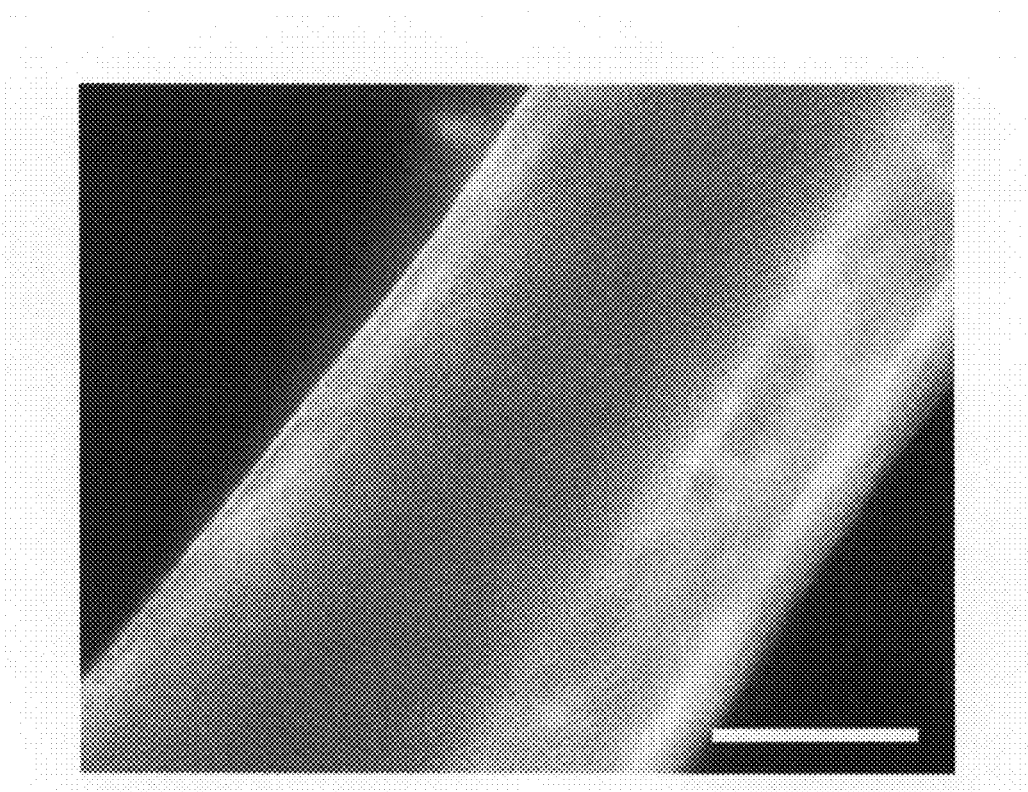
Figure 9D:
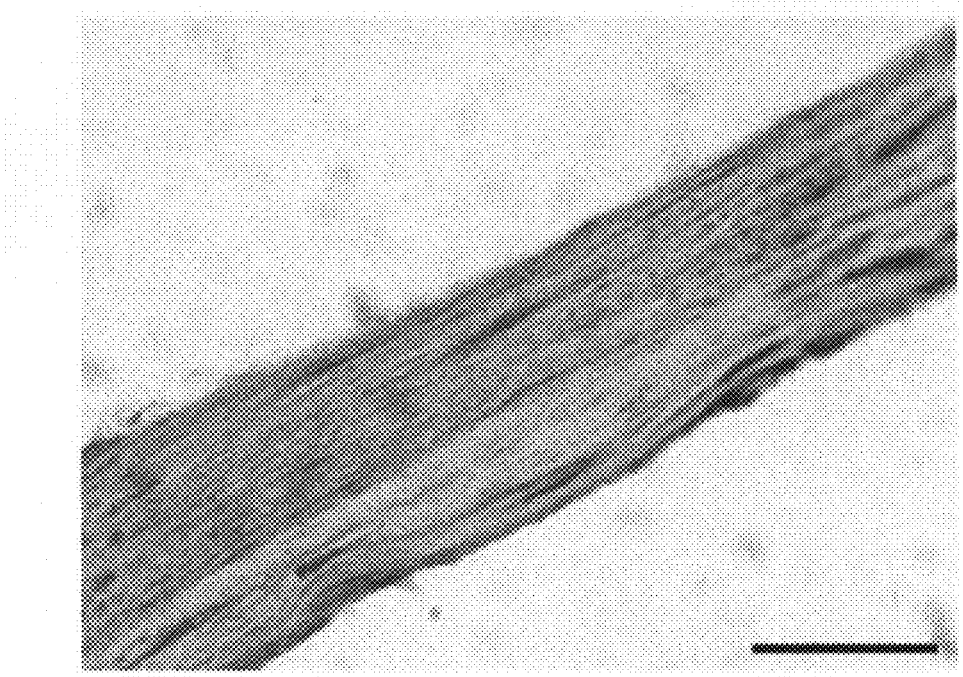

FIGS. 9a-d are collagen type I immunostaining (FIGS. 9a-c) and histological (FIG. 9d) analyses of the tendons generated from the hESCs derived CTPs of the present invention. Immunostaining with anti type I collagen (green) demonstrates the progressive assembly of long, cylinder-shaped constructs. Note a couple of cell-wide structure (FIG. 9a) arising from the bottom of the culture plate (L, FIG. 9a) attaching to the plate side wall (U, FIG. 9a) in tendons formed following about 10-14 days in culture. At a later developmental stage (following 2-3 weeks in culture), wider structures were observed (FIG. 9b), until the formation of well defined, tendon-like constructs (FIG. 9c) which was observed following 4-6 weeks in culture. Nuclei were counterstained with DAPI (blue). Histological examination shows organized, parallel-aligned cells, with high matrix-to-cell ratio (FIG. 9d); Size bars in FIGS. 9a-d—100 µm.

Figure 10A:
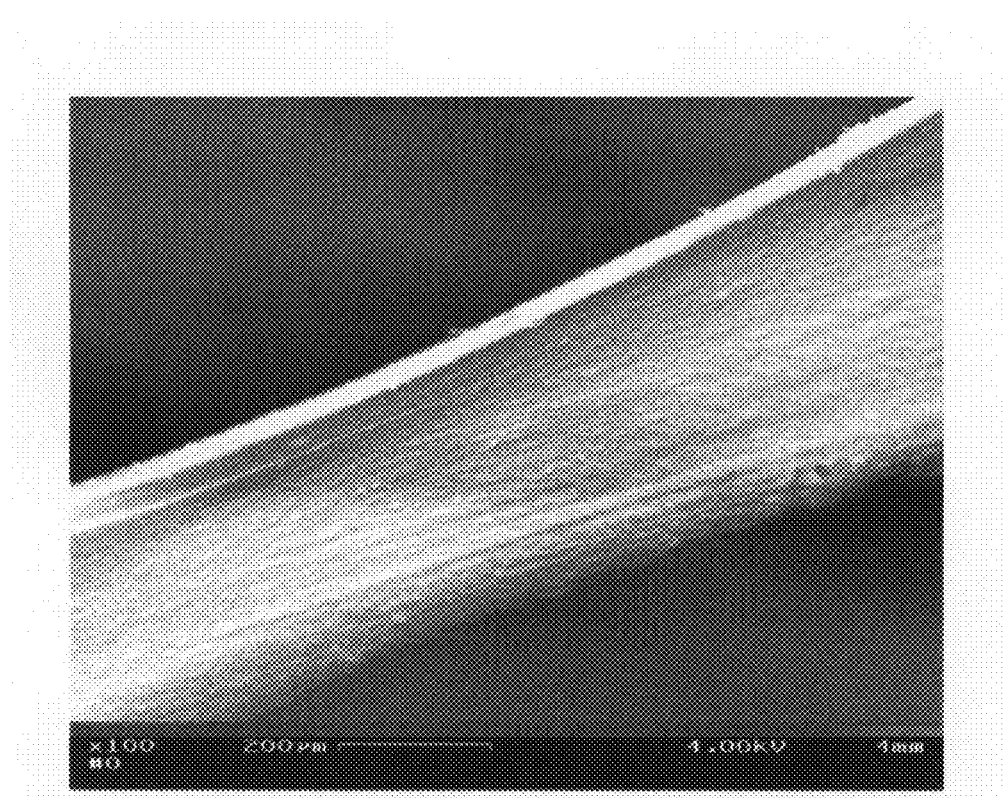
Figure 10B:
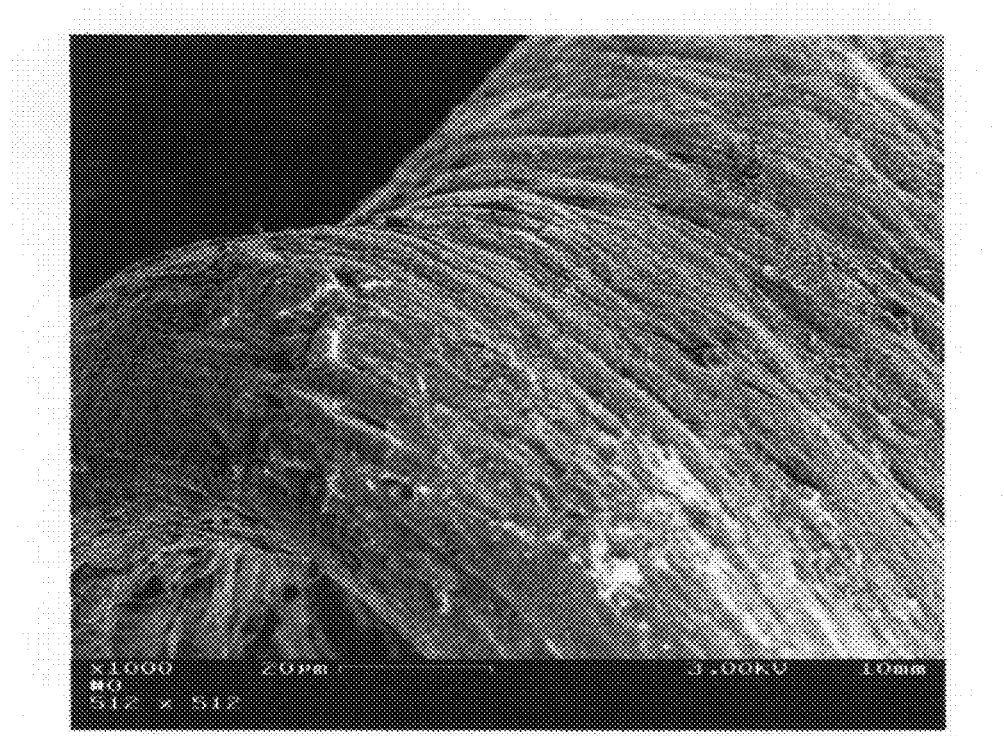
Figure 10C:
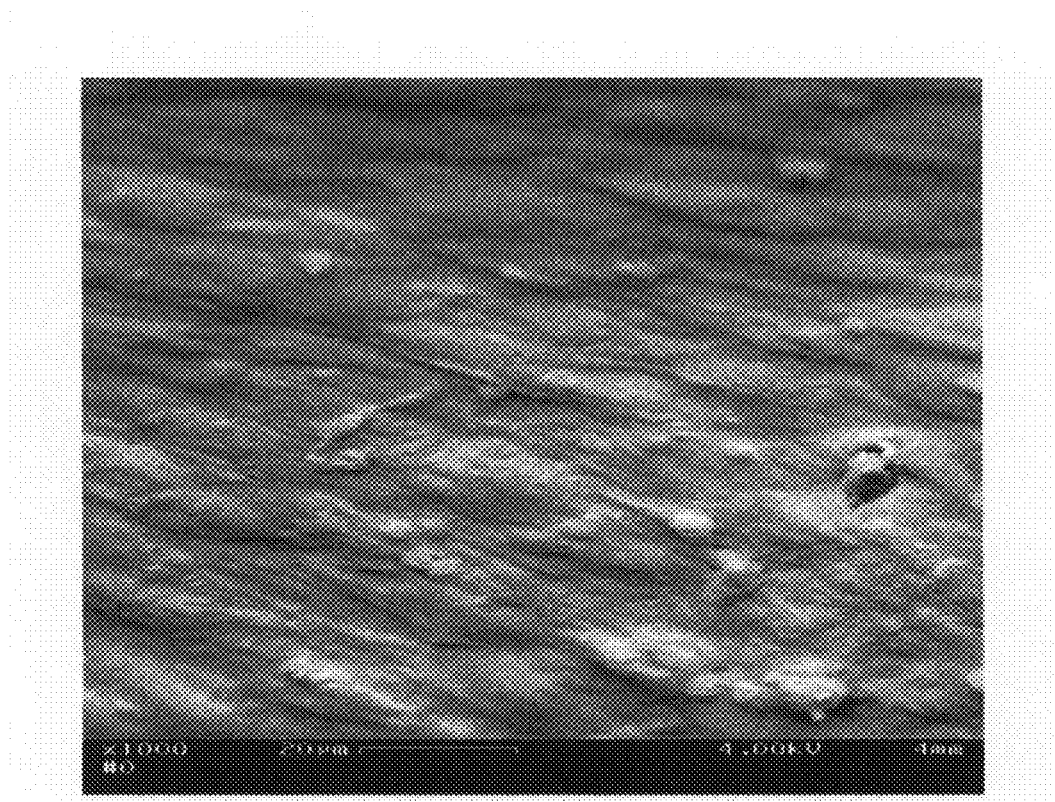

FIGS. 10a-c are SEM analyses of the tendon formed in vitro from the hESCs derived CTPs of the present invention. Note the surface topography of the constructs, showing well-defined fibrous structure (FIGS. 10a and b) and parallel orientation of cells (FIG. 10c).

Figure 11A:
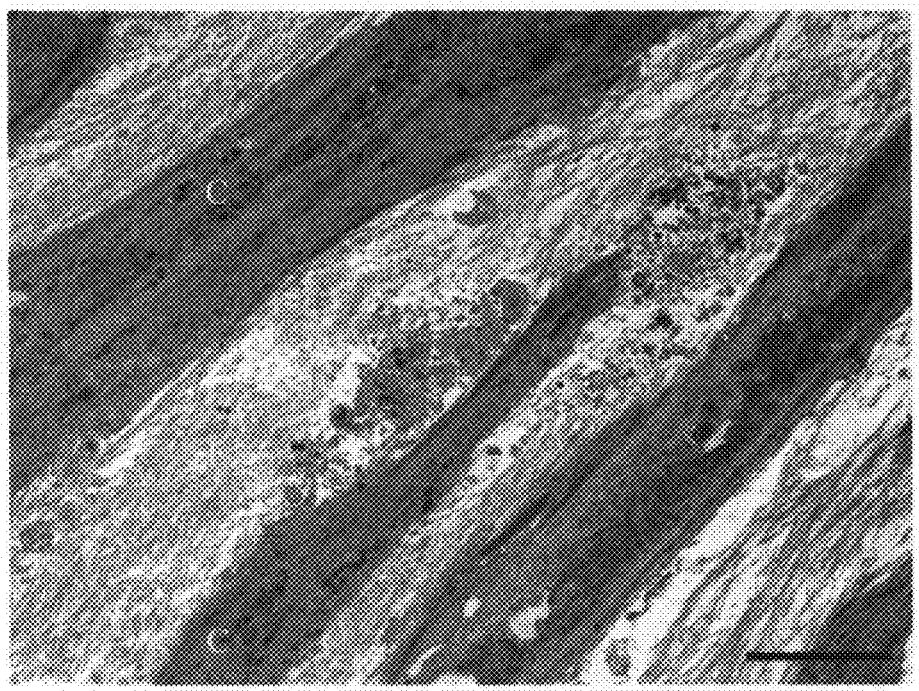
Figure 11B:
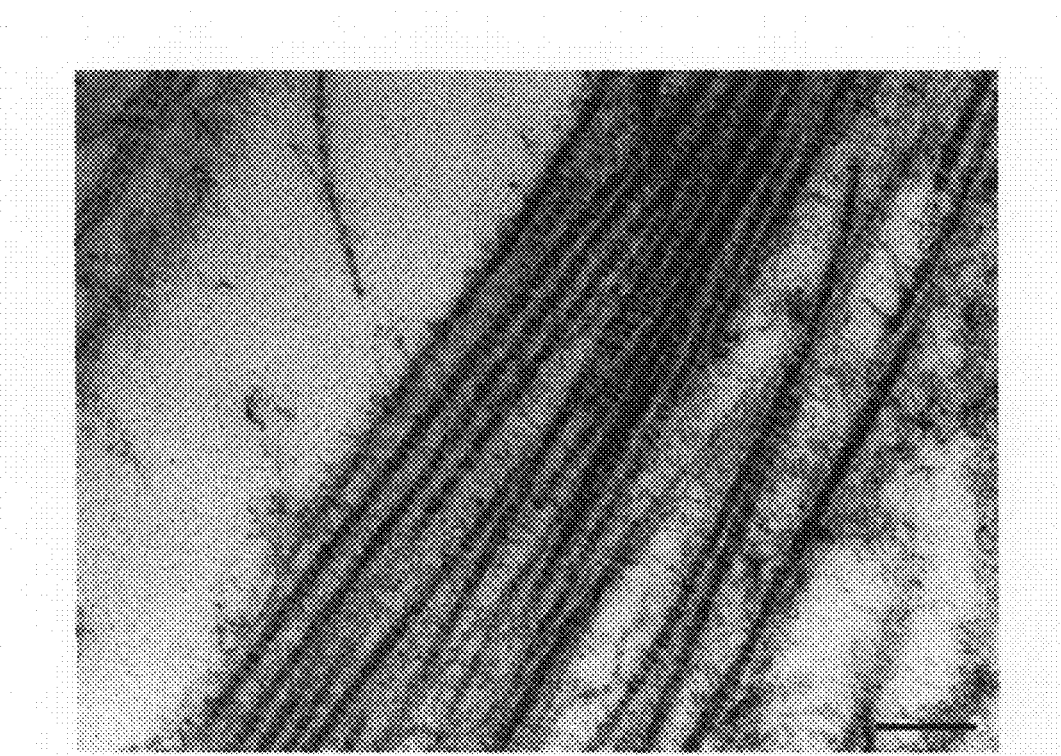
Figure 11C:
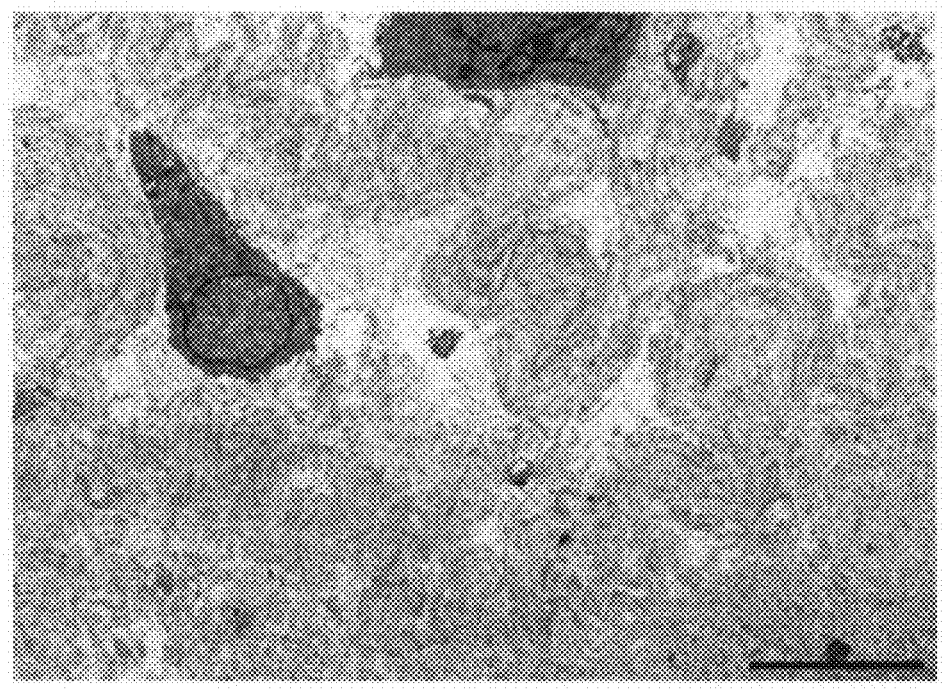
Figure 11D:
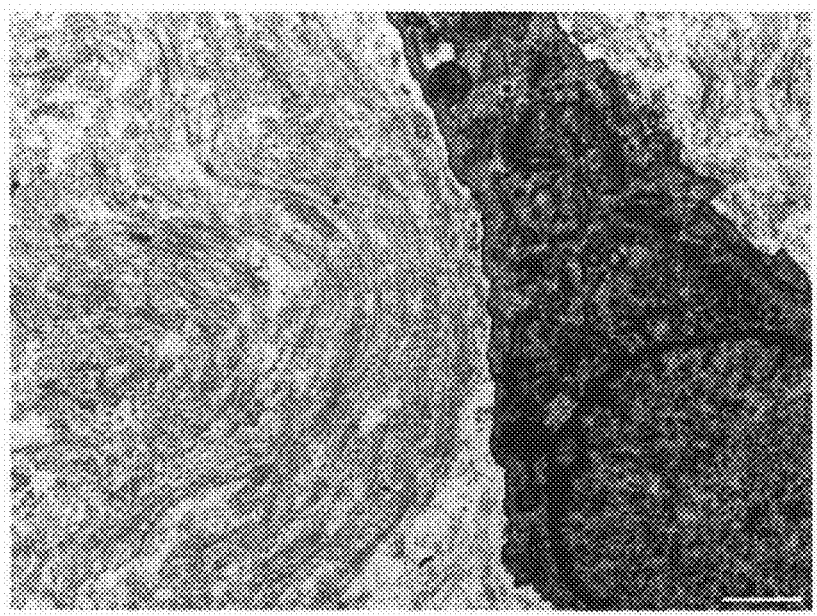

FIGS. 11a-d are TEM analyses of longitudinal sections demonstrating the ultrastructure of the developing tendon, with elongated cells (marked with "C", FIG. 11a) aligned in parallel (FIG. 11a), surrounded with interwoven bundles of collagen fibrils (marked with "E", FIG. 11a) seen also at higher magnification (FIG. 11b), and on cross sections (FIGS. 11c and d). Scale bars: FIG. 11a—5 µm, FIG. 11b—200 nm FIG. 11c—5 µm, FIG. 11d—700 nm.

Figure 12:
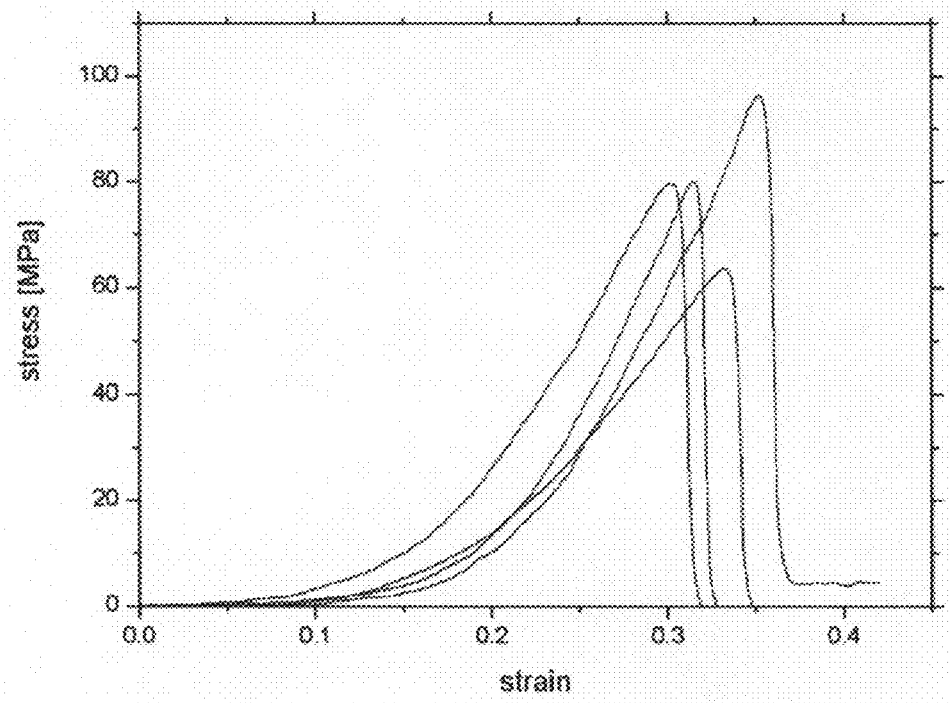

FIG. 12 is a strain-stress test depicting strain-stress curves of 4 independent tensile tests of engineered tendons, with an average tangent modulus of 586.6±118.7 MPa, and ultimate tensile strength (UTS) of 79.7±13.3 MPa (see also Table 3 of the Examples section which follows). The initial length and diameter of the tendons were 2.4 mm and 0.2 mm respectively. The tendon constructs were stressed until failure at a strain rate of 0.02 sec$^{-1}$.

Figure 13A:
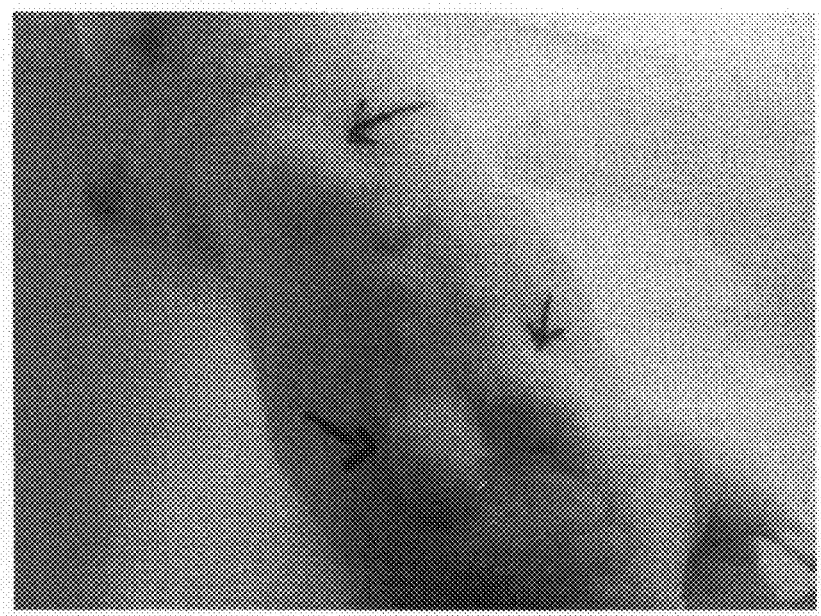
Figure 13B:
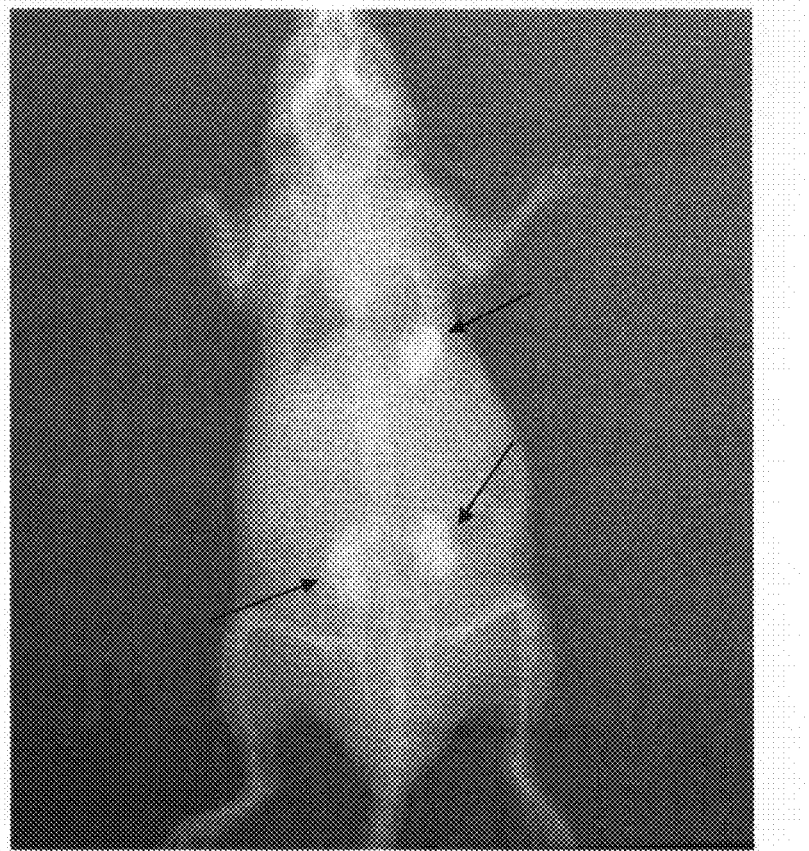
Figure 13C:
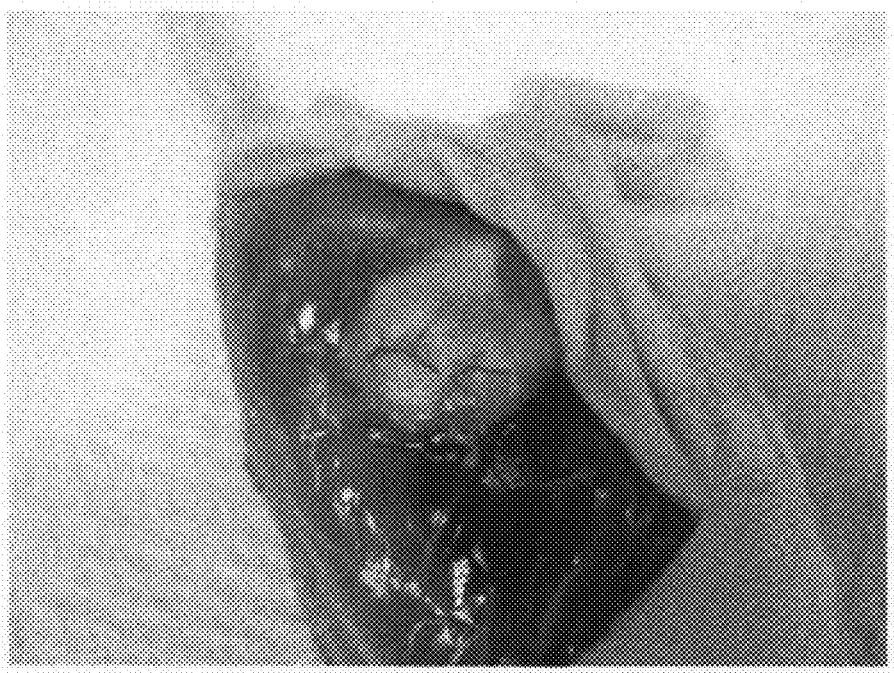

FIGS. 13a-c depict ectopic new bone and cartilage formation following transplantation of the hESCs derived CTPs of the present invention. FIG. 13a—a macroscopic view of a mouse bearing ectopic subcutaneous transplants of hESCs derived CTPs obtained from any passage of 4-20 passages. Note the visible ectopic transplants (marked with arrows, FIG. 13a) shown 8 weeks following transplantation; FIG. 13b—an x-ray image of a mouse bearing 8-week old ectopic subcutaneous transplants of hESCs derived CTPs. Note the radio-opaque transplant (marked by arrows, FIG. 13b) demonstrating the presence of bone tissue in the ectopic transplant; FIG. 13c—a macroscopic view of an 8-week old ectopic transplant following removal of skin. Note the round shape (characteristics of a non-cancerous mass), well-vascularized ectopic transplant mass, demonstrating that the ectopic transplant is biocompatible, well integrated within the recipient mouse and not rejected by its immune system.

Figure 14A:
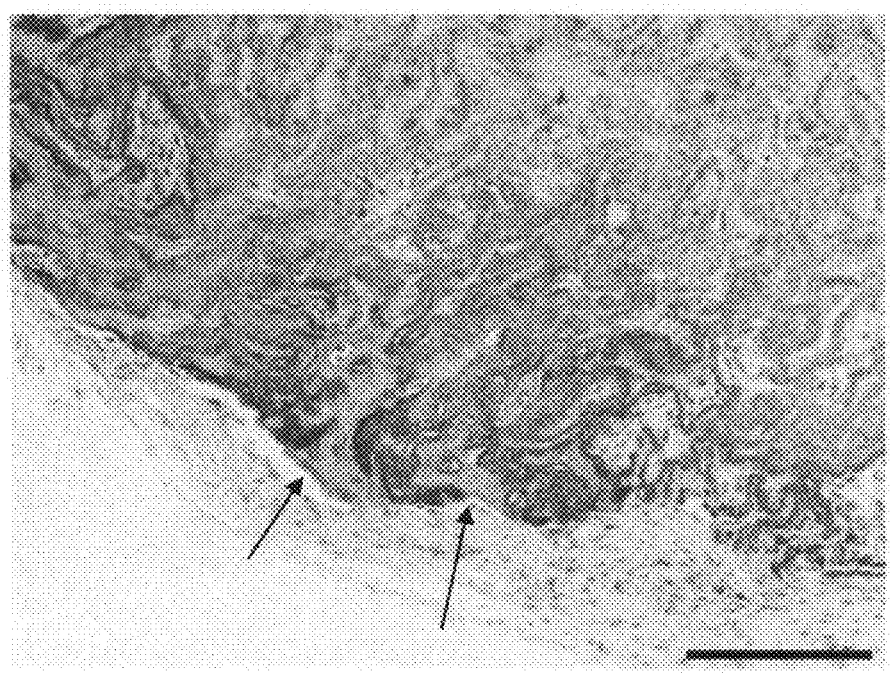
Figure 14B:
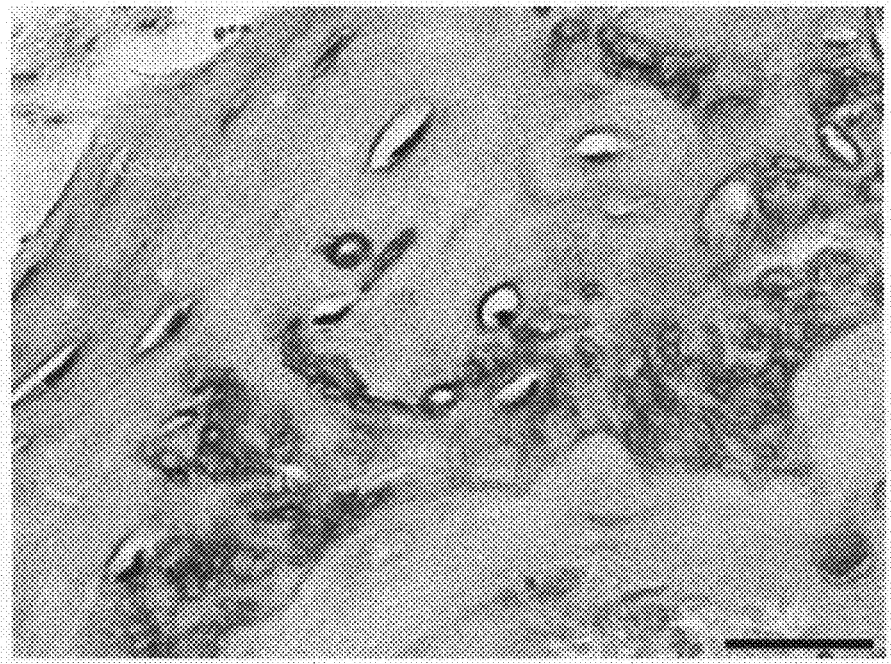
Figure 14C:
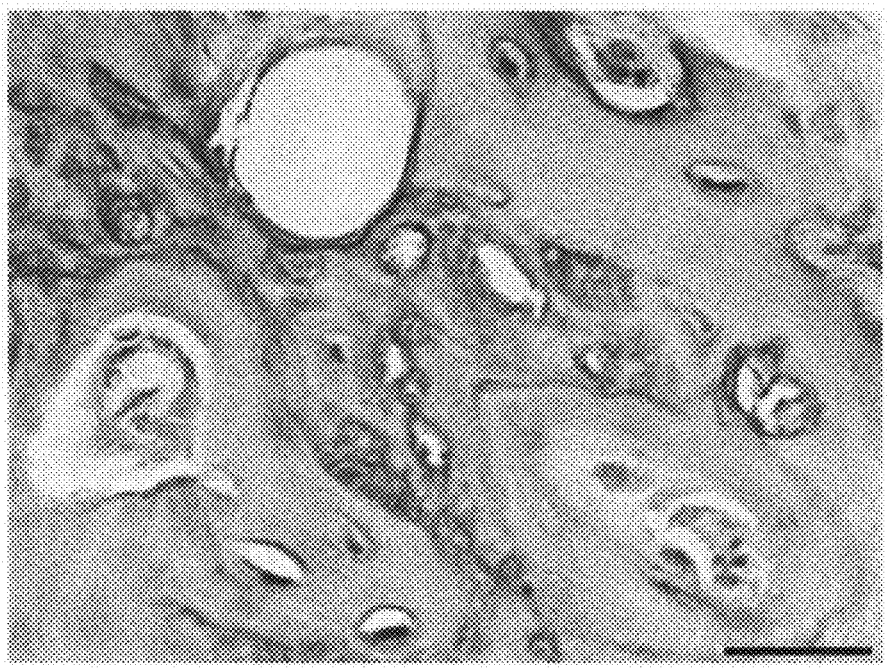
Figure 14D:
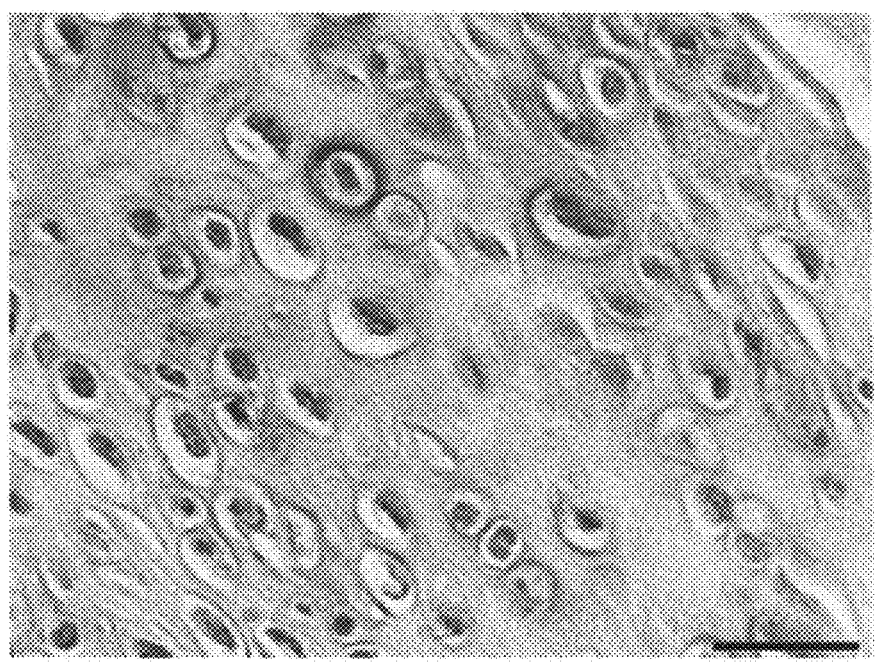
Figure 14E:
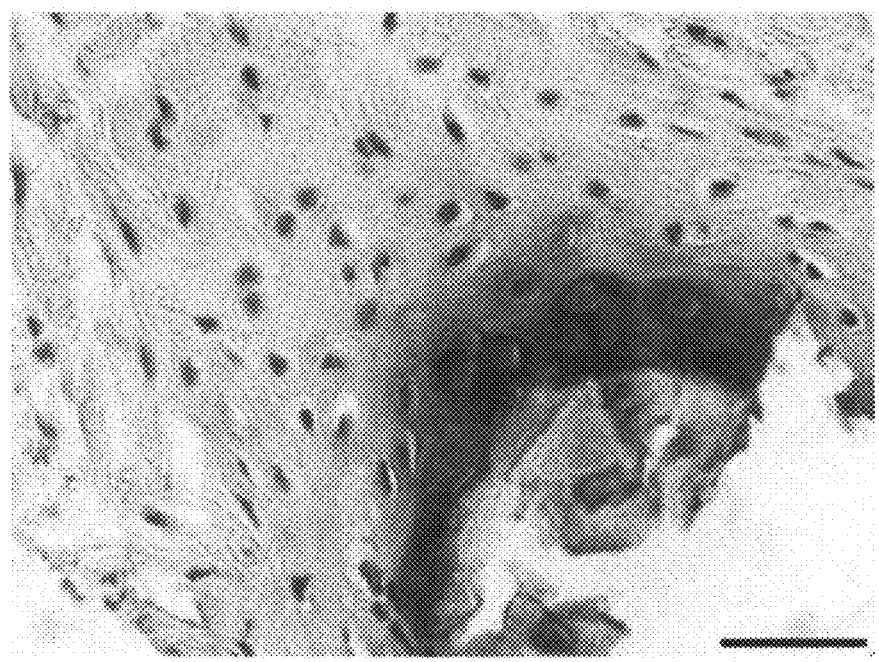

FIGS. 14a-e are histological analyses of the ectopic transplant shown in FIGS. 13a-c depicting the formation of new bone (FIGS. 14a-c) and cartilage (FIGS. 14d-e) tissues. Note the early stage of mineralized bone matrix formation (FIG. 14a, arrows), and the later stage showing osteon-like structures and new bone formation (FIGS. 14b and c), in addition to hypertrophic cartilage (FIGS. 14d-e). Scale bars: FIG. 14a—100 μm, FIGS. 14b, c and e—20 μm, FIG. 14d—15 μm.

Figure 15A:
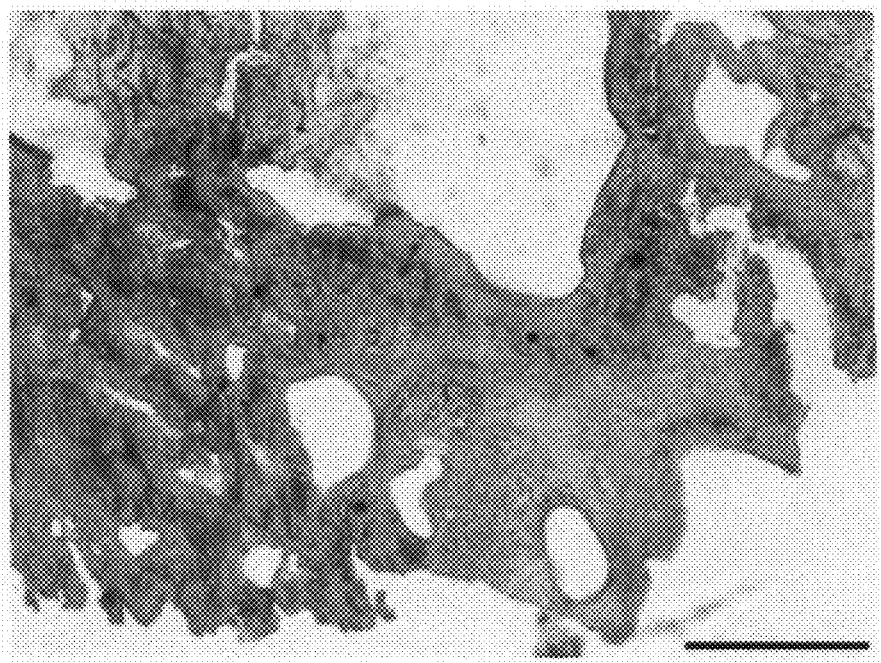
Figure 15B:
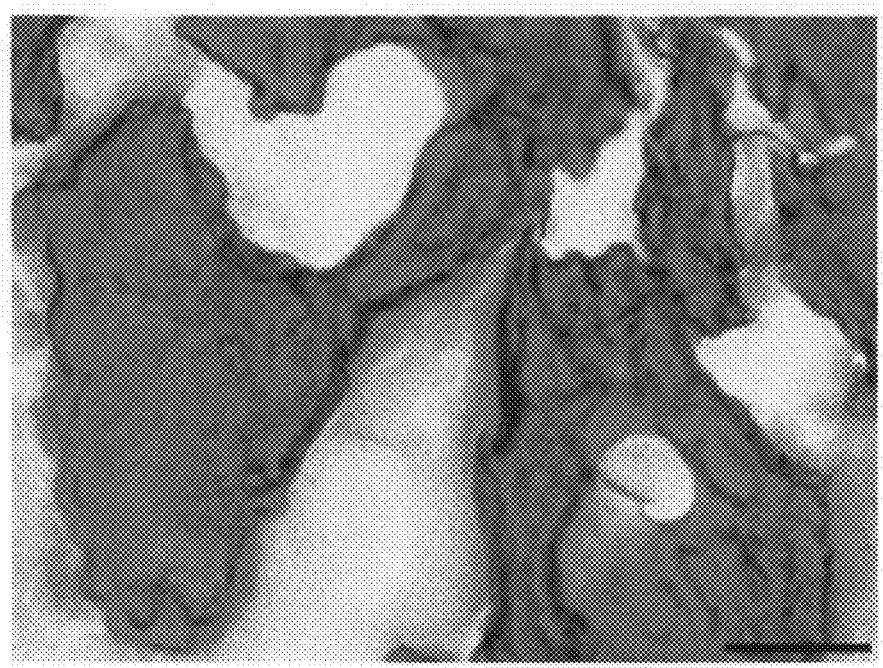

FIGS. 15a-b are images of frozen sections of non-demineralized tissue (of the ectopic transplant shown in FIGS. 13a-c) demonstrating the formation of mineral deposits (FIG. 15b), stained also with alizarin-red (FIG. 15a). Scale bars: FIG. 15a—100 μm, FIG. 15b—20 μm.

Figures 16A, 16B, 16C:
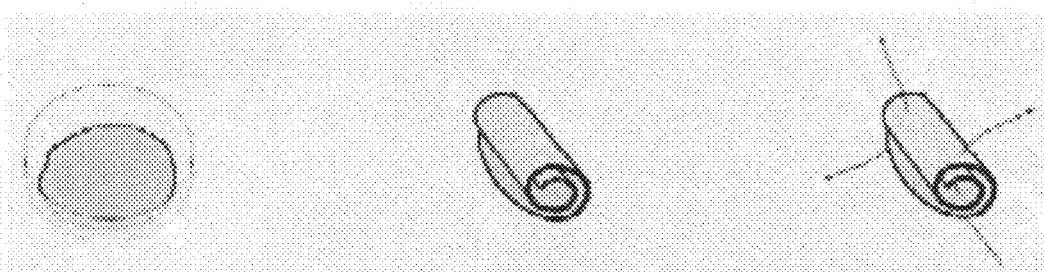
Figures 16D, 16E:
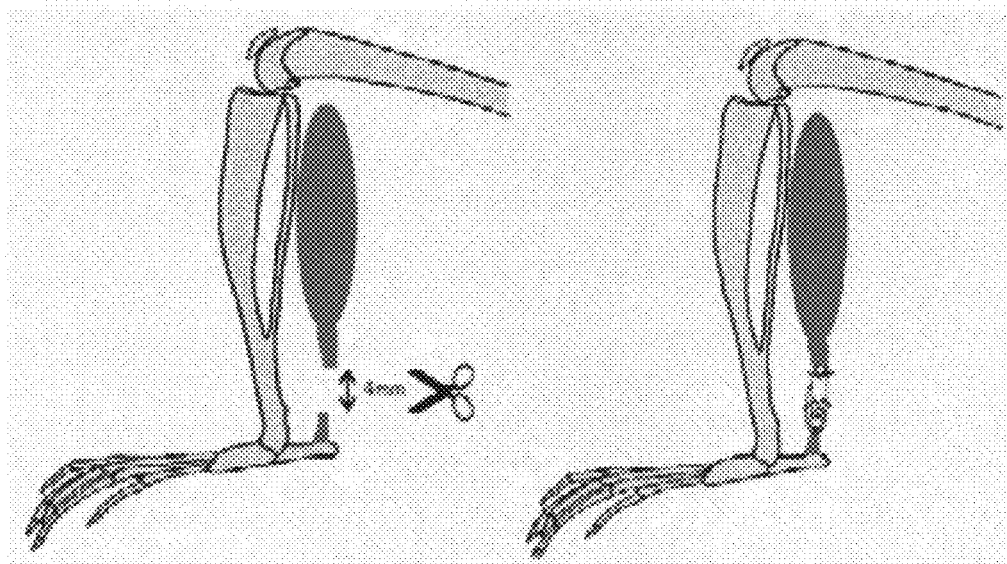

FIGS. 16a-e schematically depict the strategy of repairing critical Achilles-tendon injury by implanting a tendon graft formed from the hESCs derived CTPs of the present invention. FIG. 16a—High-density hESCs derived CTP cultures are grown with no further splitting for 4-5 weeks to form sheet-like tissues in culture plates. FIG. 16b—Once sheet-like tissues are formed, the tissues are gently removed from plates using a cell scraper and rolled to form rounded cylinders. FIG. 16c—Non-absorbable sutures are inserted at the ends of a construct through all layers. FIG. 16d—Constructs are immediately used for transplantation or kept inside custom-made templates made from flexible silicon tubes embedded in agar plates (see FIG. 17b). Full thickness, 3-4 mm long segment of the Achilles tendon in nude mice is cut to form a critical gap. FIG. 16e—The tendon graft constructs are sutured to the proximal and distal edges of the injured Achilles tendon.

Figure 17A:
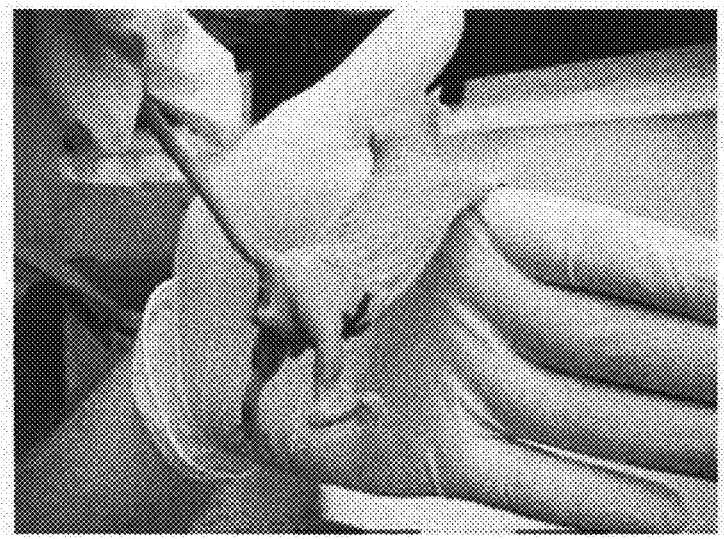
Figure 17B:
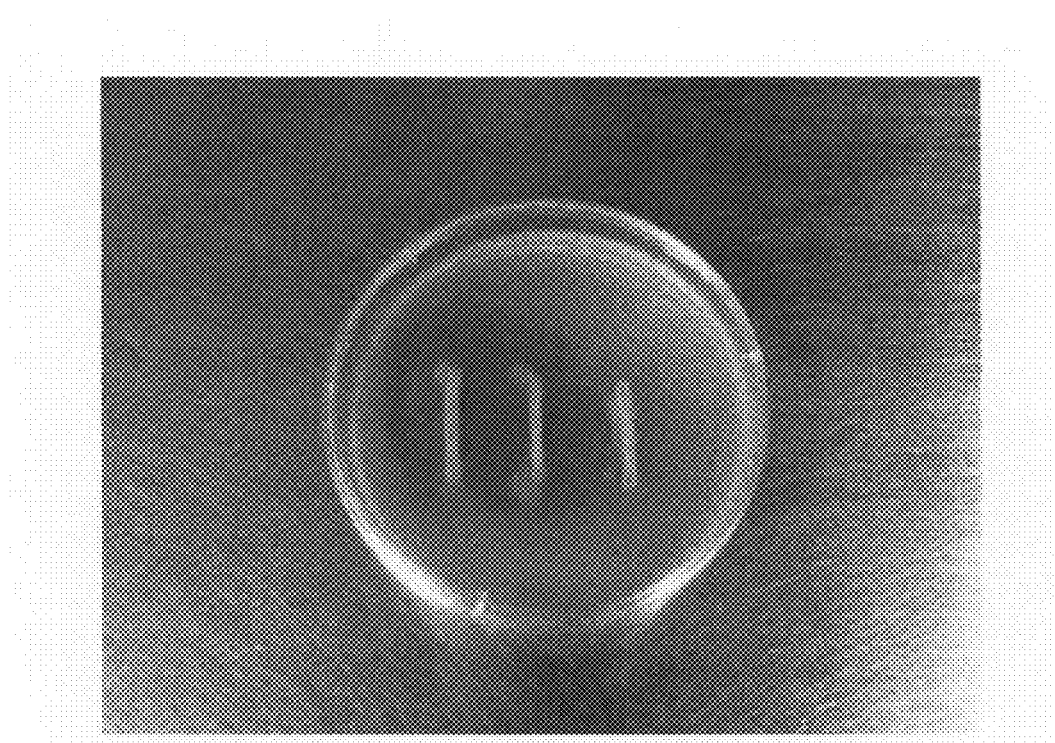
Figure 17C:
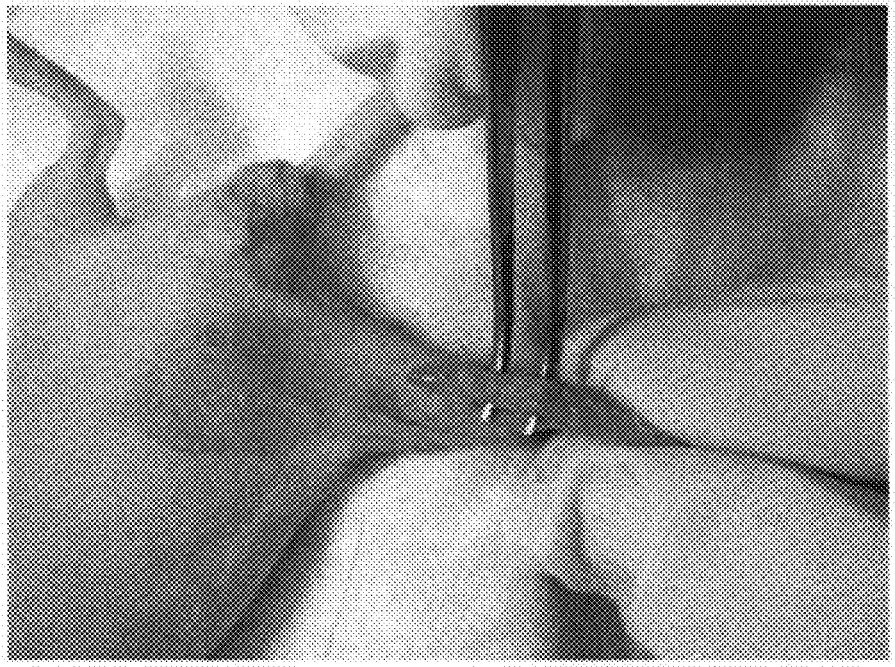
Figure 17D:
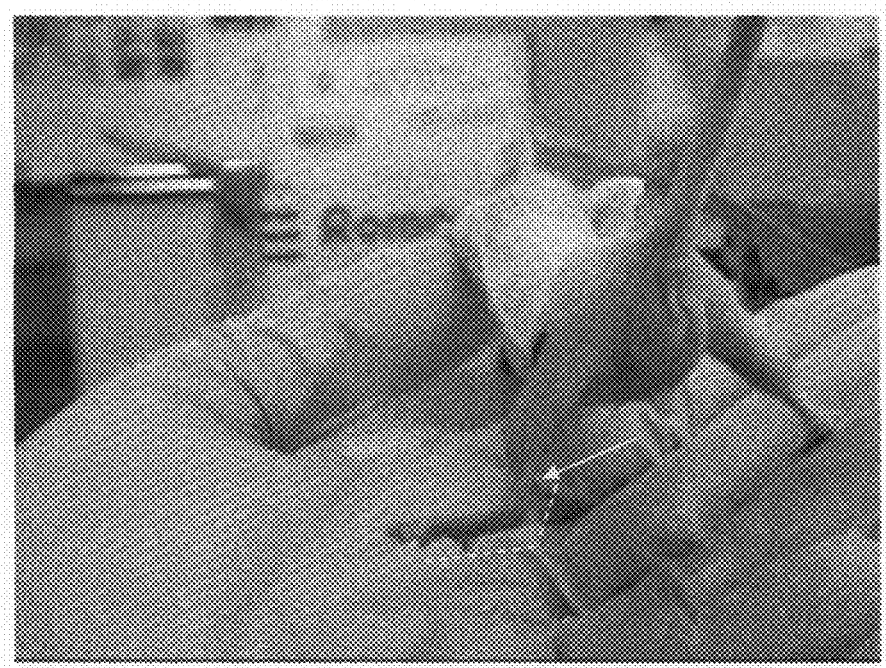

FIGS. 17a-d depict the repair of a critical Achilles-tendon injury in vivo following transplantation of a tendon which was formed in vitro from hESCs derived CTPs. FIG. 17a—A macroscopic view of a non-transplanted animal which was subjected to critical Achilles-tendon injury (excision of the Achilles-tendon). Note that the mouse is unable to extent its ankle, resulting in a maximal extension of is less than 90 degrees (yellow lines). FIG. 17b—a macroscopic view of the in vitro formed tendon grafts of the present invention (formed from hESCs derived CTPs). FIG. 17c—a macroscopic view of the in vitro formed tendon graft following its implantation into a mouse leg, replacing critically injured Achilles tendon. FIG. 17d—A view over a transplanted animal following repair of a critically injured Achilles tendon with the in vitro formed tendon graft (the tendon graft is visible, arrow). Note that one month after implantation the mouse is capable of extending its operated ankle to more than 90 degrees (yellow lines).

Figure 18A:
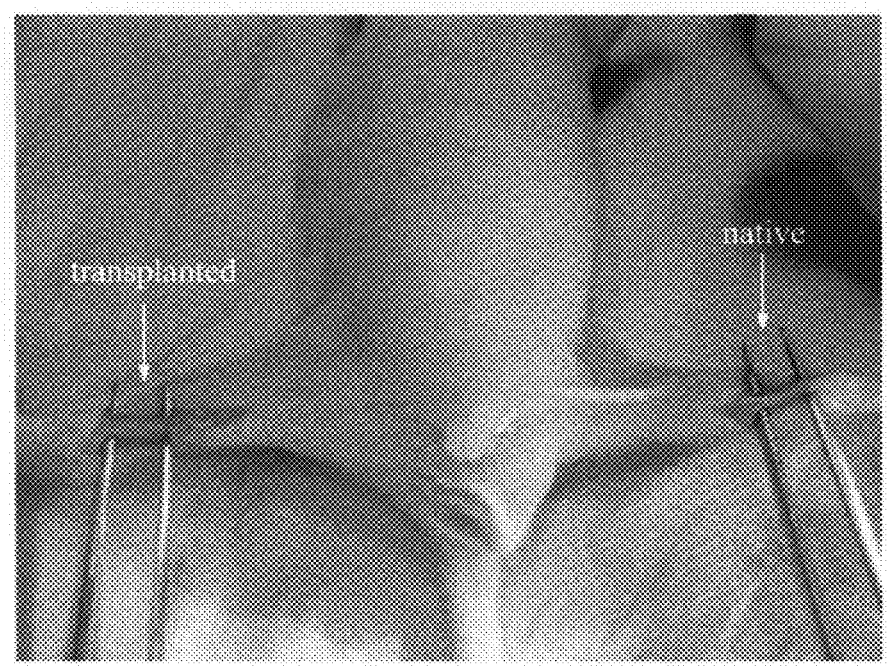
Figure 18B:
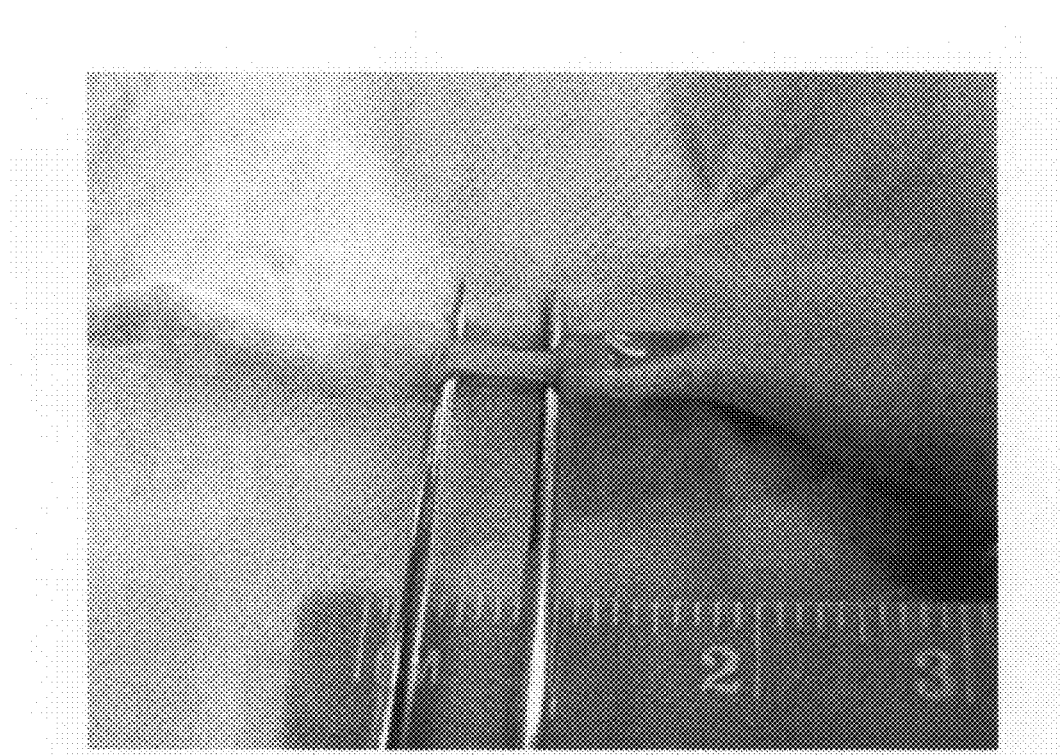
Figure 18C:
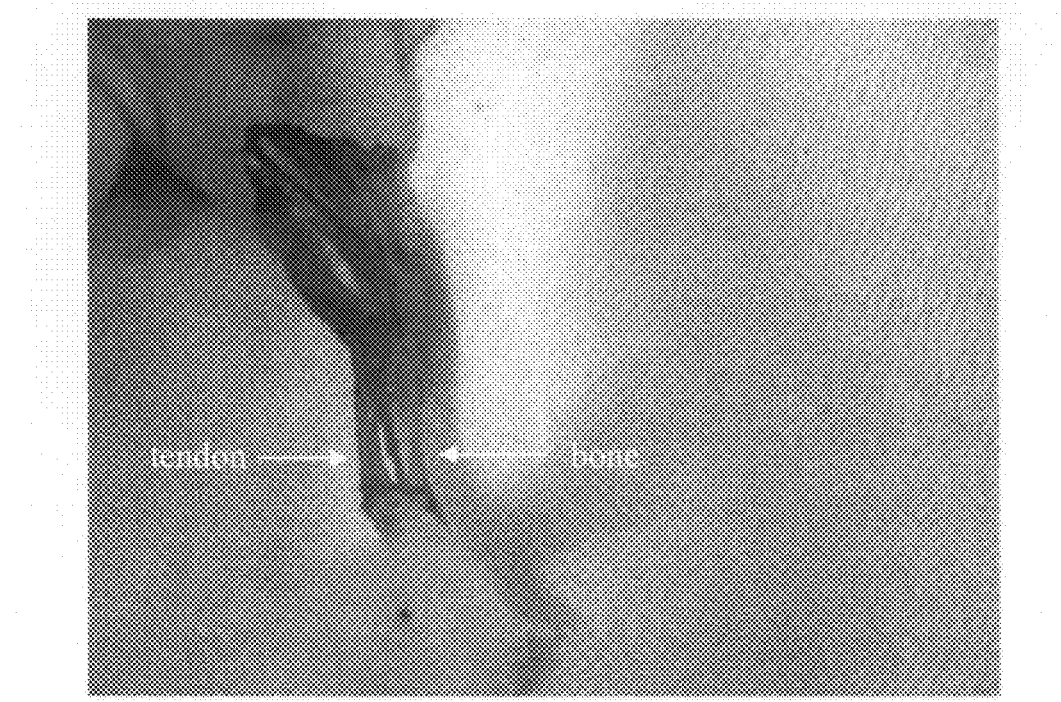

FIGS. 18a-c are macroscopic views of transplanted mice following 8 weeks of transplantation of the in vitro formed tendon graft of the present invention (which was formed from hESCs derived CTPs). FIG. 18a—The transplanted (left leg) and the native (right leg) tendons of a mouse are shown. Note the remodeling of the transplanted tendon (arrow on the left leg) to form cylinders with smooth edges and good integration at the sites of suturing. FIG. 18b—magnified image of the transplanted tendon (held with the forceps). FIG. 18c—a lateral view at the transplanted tendon (arrow) showing it connects the muscle to the ankle joint.

Figure 19A:
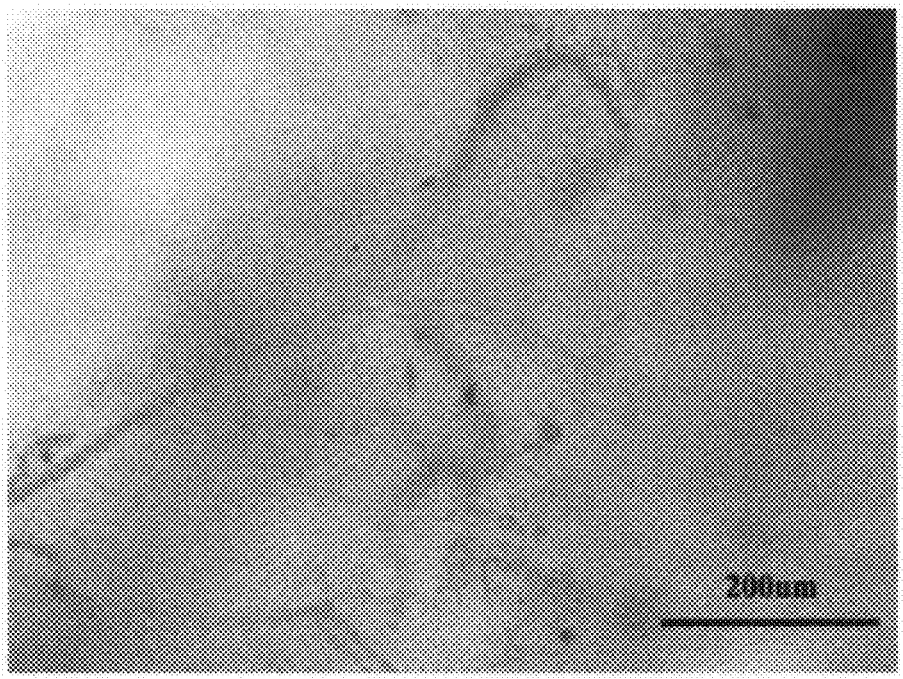
Figure 19B:
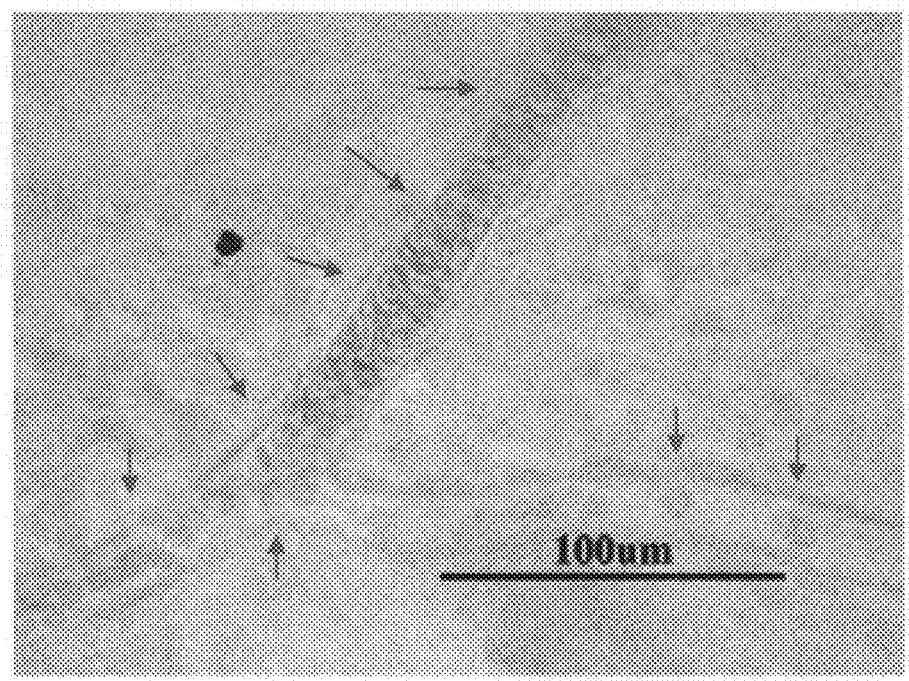

FIGS. 19a-b are microscopic images of the transplanted tendons showing circulating blood vessels invade the graft, delivering blood (arrows). Scale bars: FIG. 19a—200 μm, FIG. 19b—100 μm.

Figure 20A:
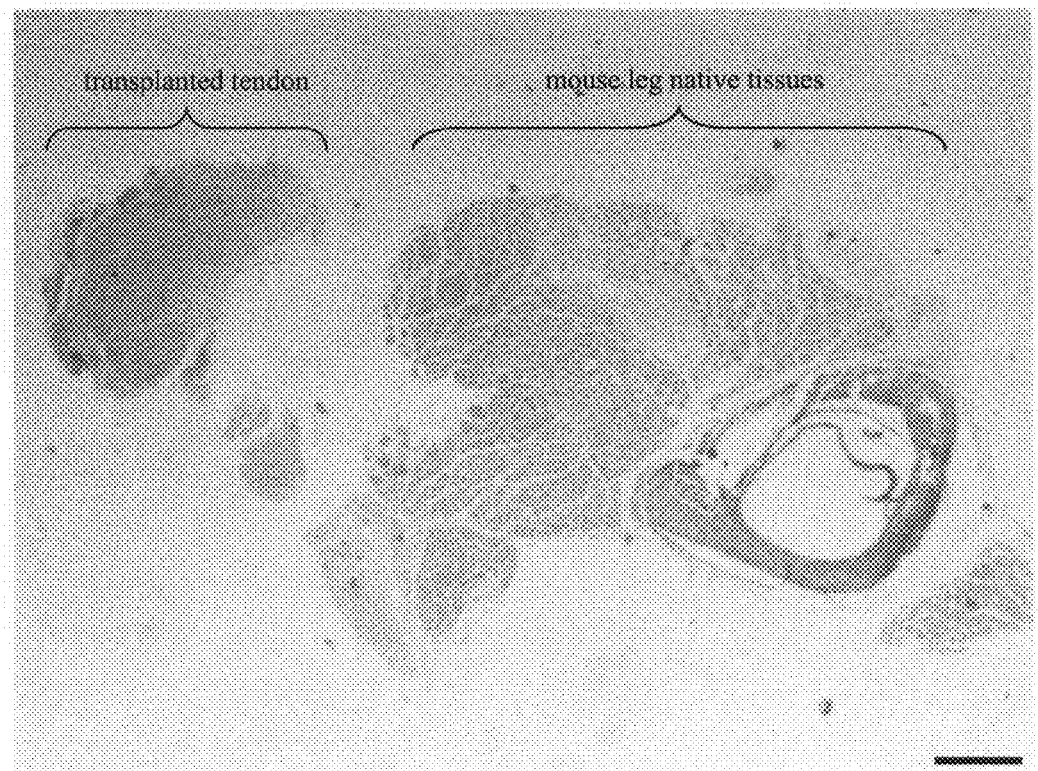
Figure 20B:
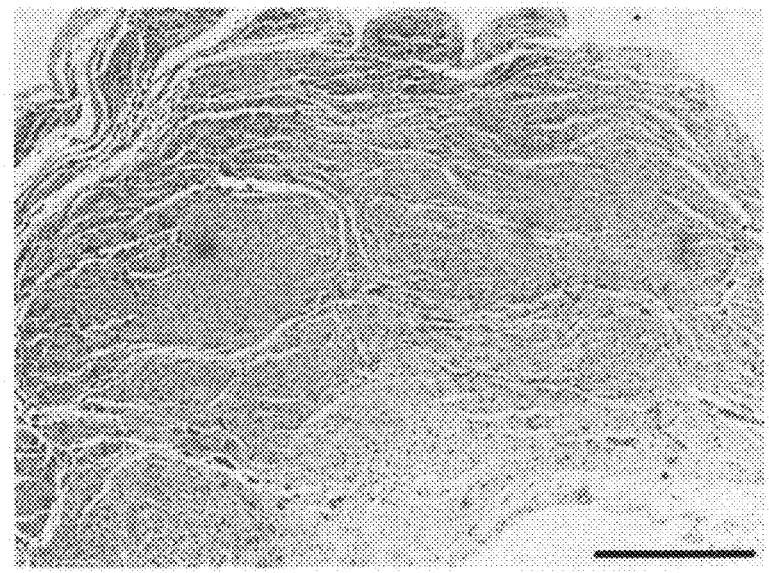
Figure 20C:
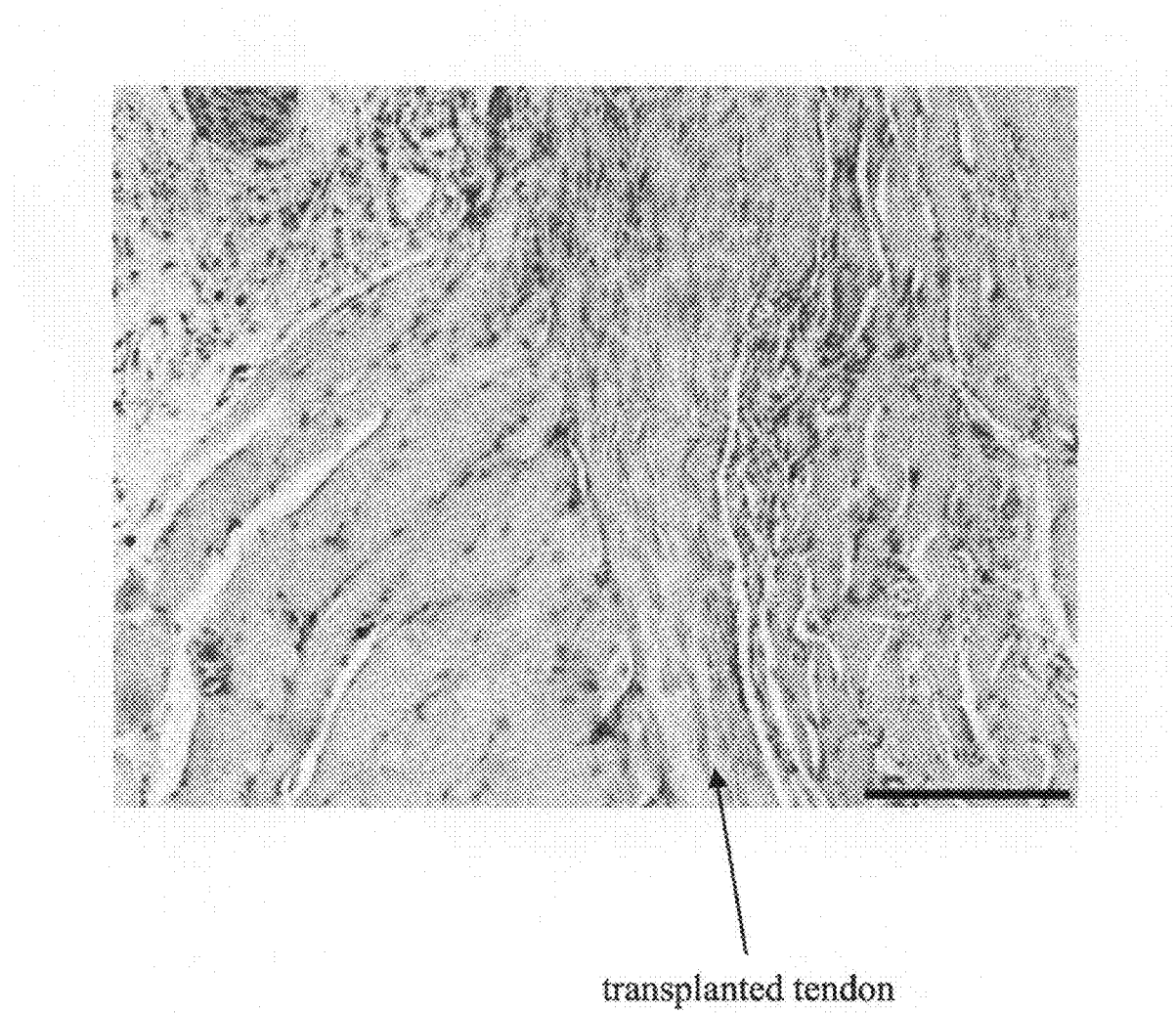

FIGS. 20a-c are histological sections of a transplanted tendon as shown in FIGS. 18a-c. FIG. 20a—a cross section of a transplanted mouse leg demonstrating the transplanted tendon and the mouse leg native tissues. FIG. 20b—a cross section of the transplanted tendon. FIG. 20c—a longitudinal section of the transplanted tendon. Note the fascicle-like organization and high matrix to cell ratio seen on cross section (FIG. 20b) and longitudinal section (FIG. 20c) demonstrating that grafts remodeled and integrated well. Scale bars: FIG. 20a—200 μm, FIGS. 20b and c—100 μm.

Figure 21A:
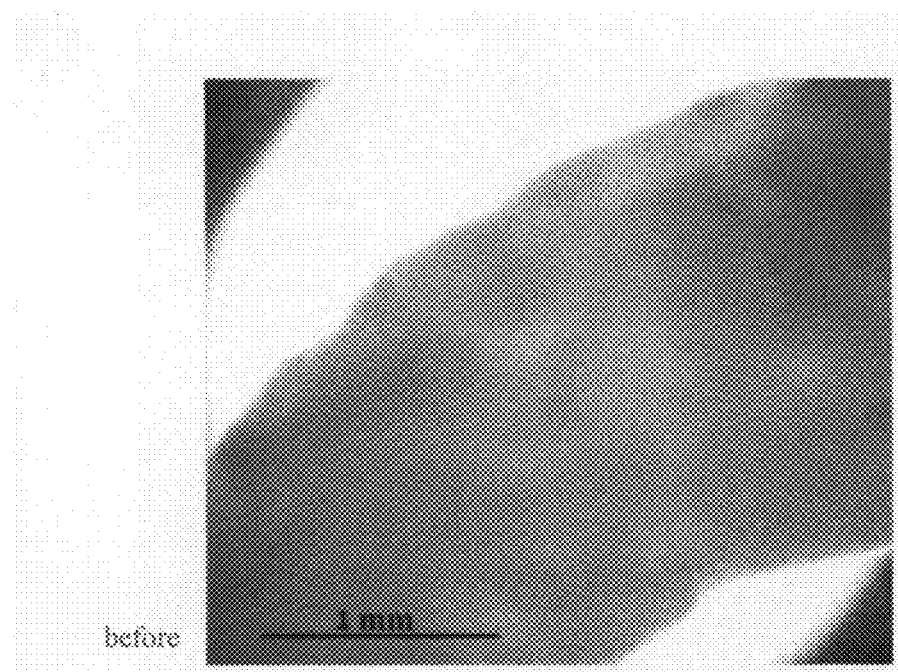
Figure 21B:
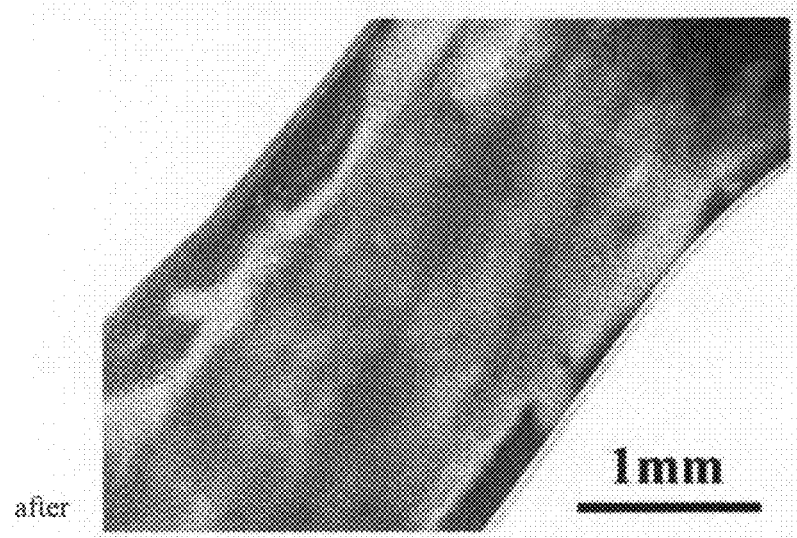
Figure 21C:
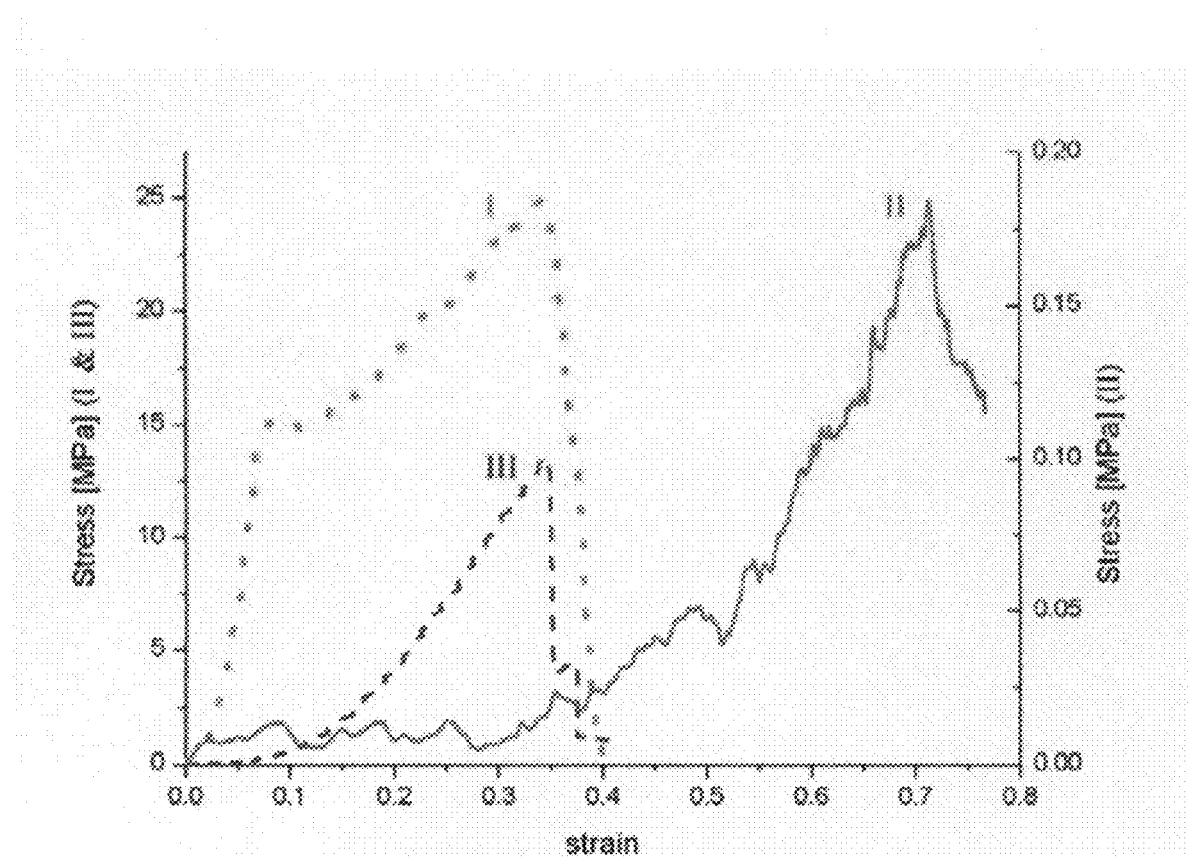

FIGS. 21a-c are photomicrographs (FIGS. 21a-b) and a graph (FIG. 21c) depicting the biomechanical remodeling of the transplanted in vitro formed tendon grafts. FIGS. 21a-b—microscopic appearance of graft before (FIG. 21a) and after (FIG. 21b) transplantation; FIG. 21c—a graph depicting the correlating tensile tests before transplantation (in red) and after transplantation (in blue). Rat tail tendon (green) was used as a control. Upon in-vivo conditioning, tendons remodel to have smoother edges and become stronger.

Figure 22A:
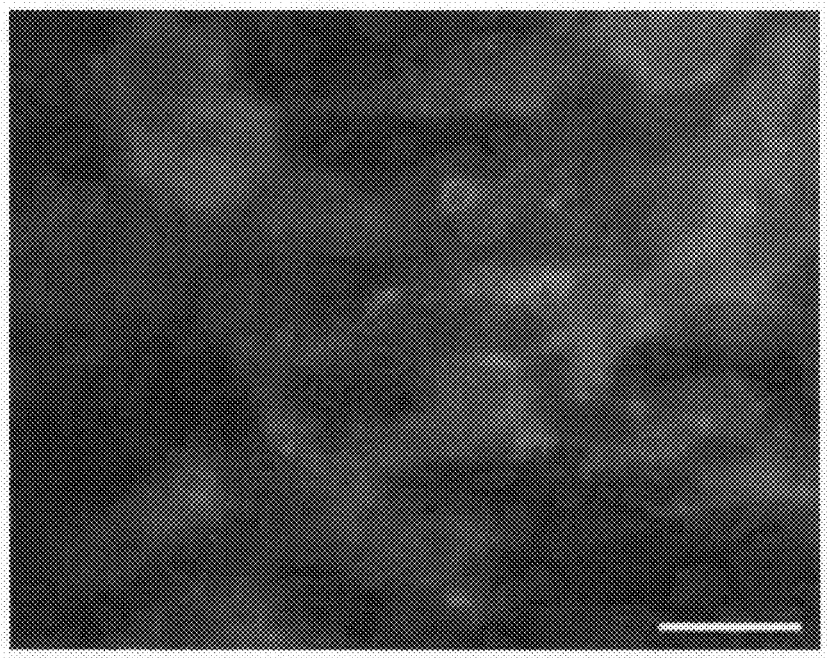
Figure 22B:
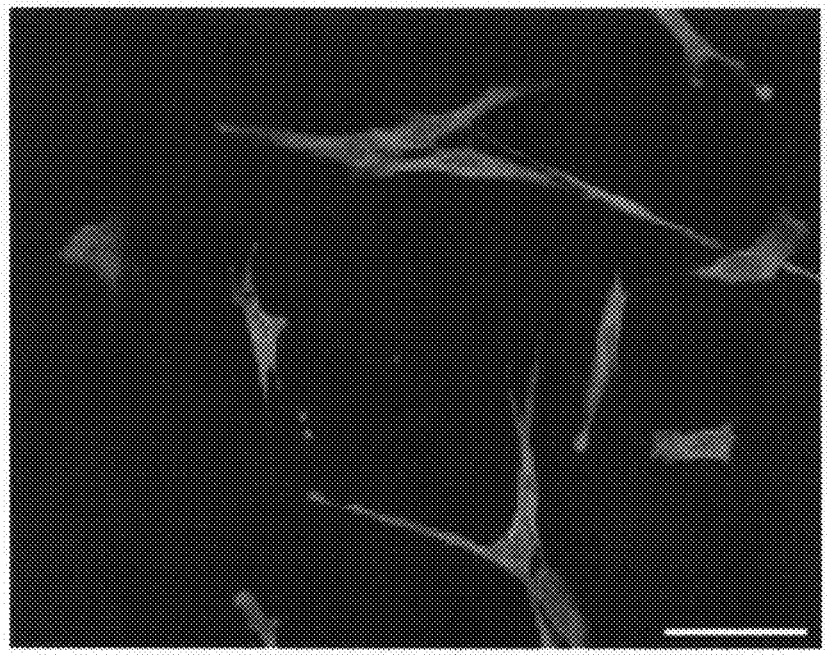

FIGS. 22a-b are photomicrographs of immunofluorescence analysis depicting that the hESCs derived CTPs of the present invention express alkaline phosphatase (ALP) (FIG. 22a) and osteocalcin (FIG. 22b). Nuclei were counterstained with DAPI (blue). Scale bars, 100 μm.

Figure 23:
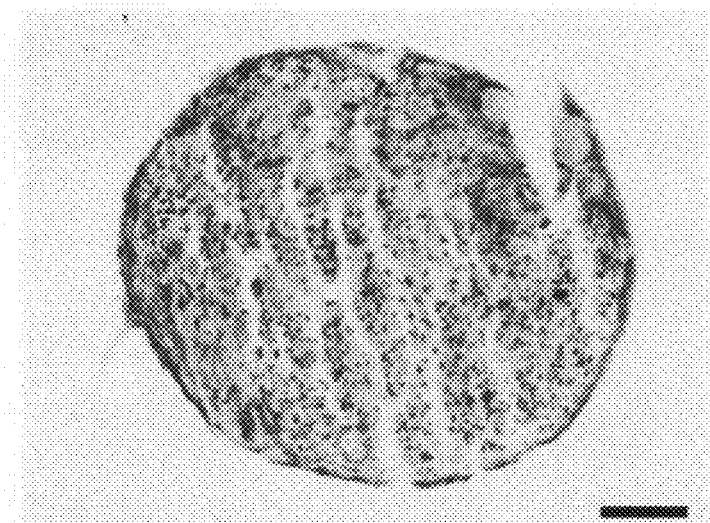

FIG. 23 is a photomicrograph of a one month old pellet section stained with Toluidine blue. Directed differentiation was induced through pellet cultures (passage 9) in the presence of low serum TGF-β3 supplemented medium. Note the presence of matrix proteoglycans (blue) in the pellet culture. Earlier pellet cultures were not positively stained (data not shown). Scale bar, 100 μm.

Figure 24A:
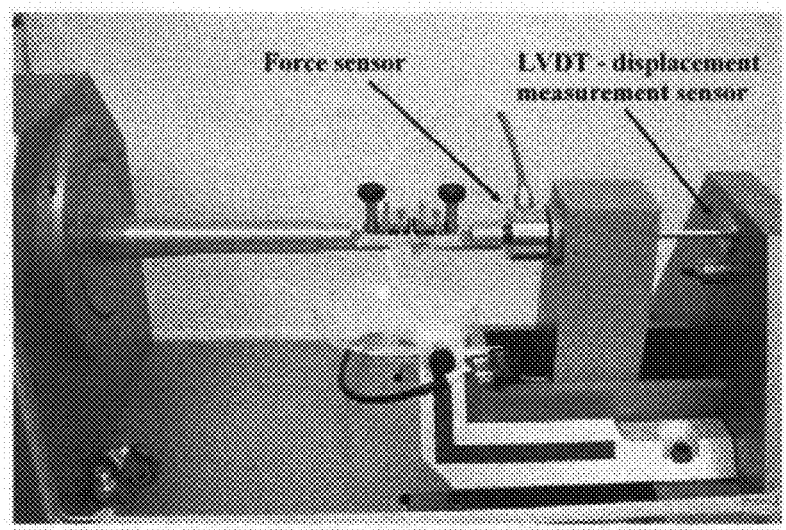
Figure 24B:
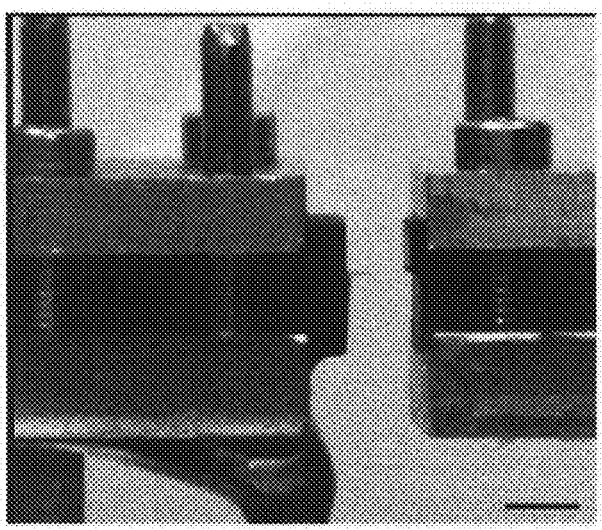

FIGS. 24a-b are photographs depicting the tensile test machine used for the biomechanical evaluation of engineered constructs. FIG. 24a—overview of the custom-made testing machine; FIG. 24b—sample clamped between its grips. Scale bar—3 mm.

Figure 25A:
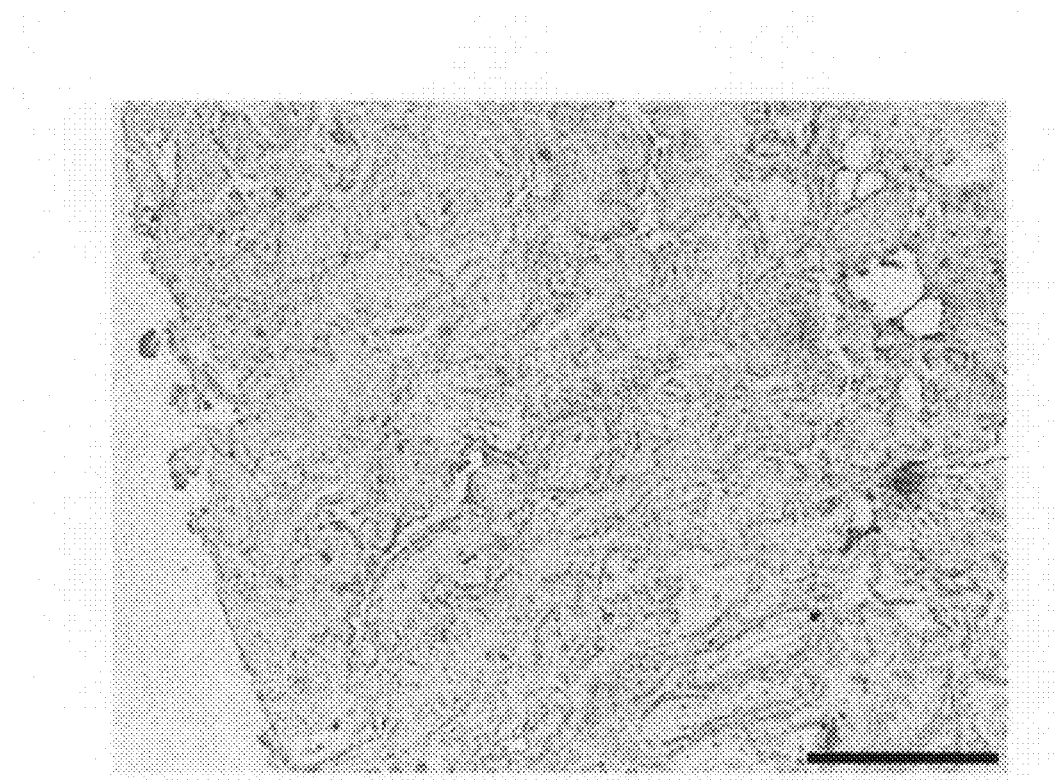
Figure 25B:
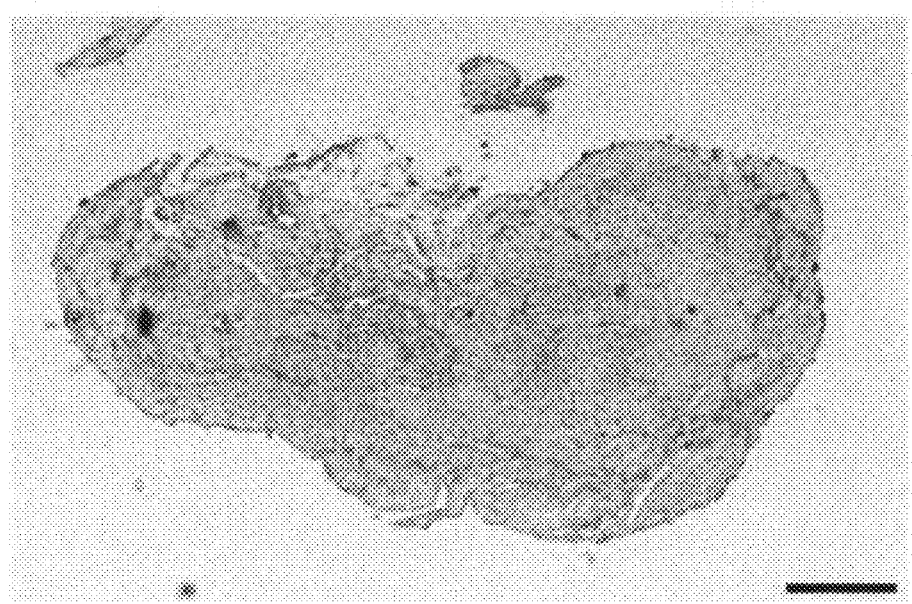

FIGS. 25a-b are photomicrographs of immunostaining analyses depicting the human identity of transplanted tissues. Sections of the ectopic transplantation (subcutaneous transplantation) of the hESCs derived CTPs of the present invention (FIG. 25a) and the transplanted tendon graft formed in vitro from the hESCs derived CTPS of the present invention (FIG. 25b) were subjected to immunostaining analysis using the anti-human mitochondria antibody (brown staining; BioGenex, San Ramon, Calif., USA, Cat. No MU213-UC). FIG. 25a—A section of the newly-formed ectopic tissue. Note the brown staining of anti-human mitochondria antibody depicting the human origin of the ectopic tissue; FIG. 25b—A cross section of the transplanted tendon graft. Note the brown staining of anti-human mitochondria antibody depicting that the transplanted tendon is of a human origin. Scale bars, 100 μm.

Figure 26:
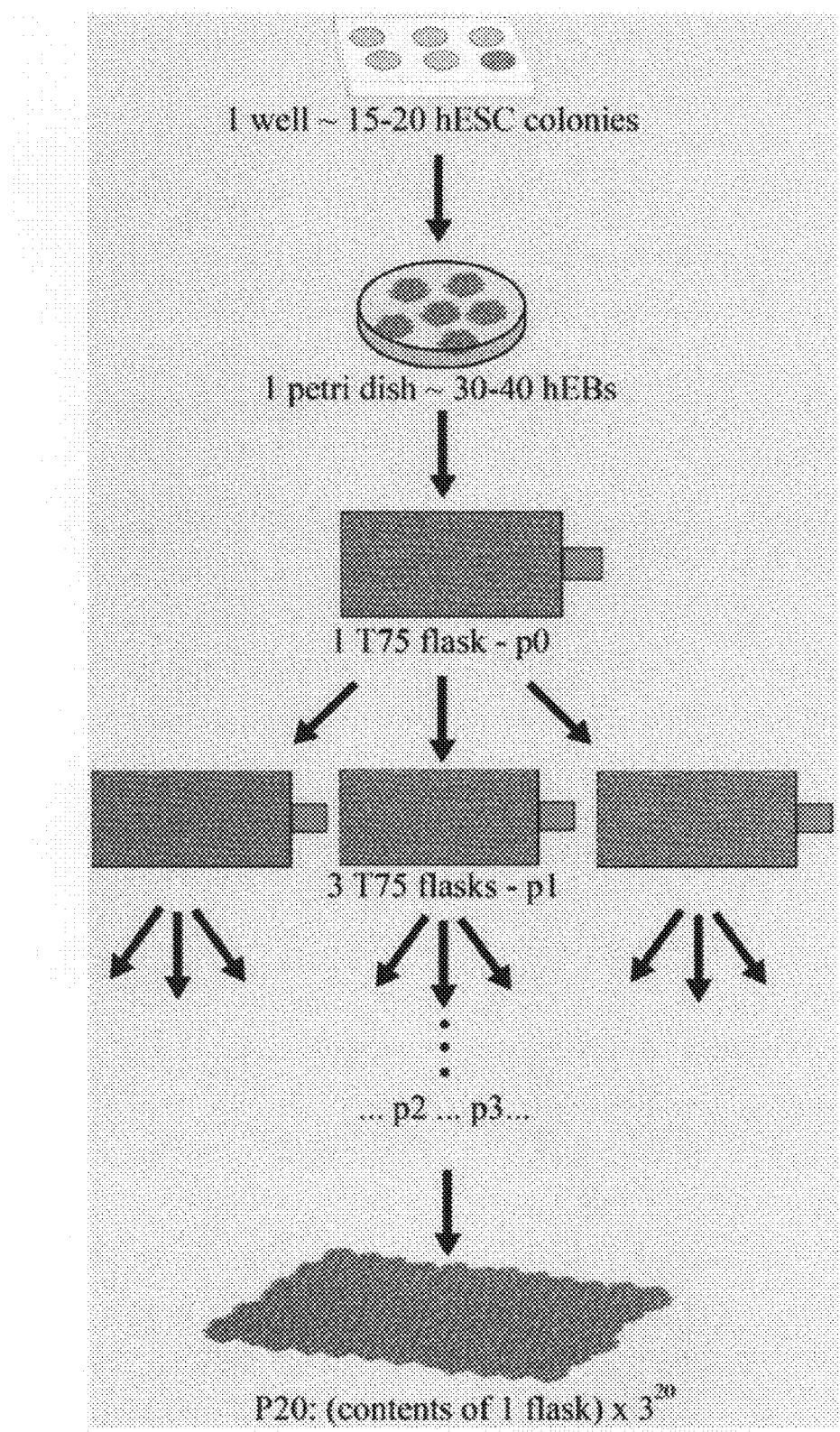

FIG. 26 is a schematic illustration depicting cell-based tissue engineering potential of the hESC-derived CTPs of the present invention. Note that one well of a 6-well culture plate containing approximately 15-20 undifferentiated hESC colonies, potentially gives rise to approximately $3^{20}$ subconfluent 75 cm$^2$ culture flasks after 20 passages.

FIGS. 27a-b are photomicrographs of sub-confluent cultures of hESC-derived CTP (passage 1; FIG. 27a) and human fetal-derived CTP (FIG. 27b), demonstrating great resemblance in morphology (scale bars, 100 μm).

DESCRIPTION OF THE PREFERRED EMBODIMENTS

The present invention is of methods of generating connective tissue progenitor cells (CTPs) from embryonic stem cells and/or embryoid bodies and of using such cells for cell based therapy and tissue engineering. Specifically, the present invention can be used to repair and regenerate damaged or diseased tissue by administering the CTPs of the present invention to a subject in need thereof or by implanting in the subject a tissue graft generated in vitro by the CTPs of the present invention.

The principles and operation of the method of generating connective tissue progenitor cells according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cell-based tissue engineering is an evolving interdisciplinary area that offers new opportunities for clinical applications, creating a tool for repairing and replacing damaged or lost tissues with biological substitutes. The current approaches of repairing damaged or disordered connective tissues, such as bone, cartilage and tendons include the use of autografts, allografts and artificial substitutes. However, while the use of cell grafts is limited by availability and morbidity, synthetic grafts are osteoconductively inferior to their biological counterparts, and could fail.

Human embryonic stem cells (hESCs) hold great promise as a source of cells for tissue engineering. Their ability of practically unlimited self-renewal can potentially provide the required amount of cells needed for ex vivo tissue construction. In addition, they are characterized by a developmental potential to differentiate into any cell type of the mammalian embryo, and recently have been efficiently derived by means of somatic cell nuclear transfer, creating patient-specific immune-matched cell lines.

Several approaches have been recently described for isolating mesenchymal stem cells (MSCs)-like cells from hESCs. For example, Olivier E N., et al., 2006 [Olivier, E. N., et al., 2006, Stem Cells 24, 1914-1922] teach culturing spontaneously differentiating cells of hESCs colonies until a thick multi-layer epithelium is formed (at least 4 weeks), following which the cells forming the thick epithelium are routinely passaged. However, the use of such a method is limited by the need to mechanically separate the spontaneously differentiating cells from hESCs, which may result in a crude, non-defined, population of cells.

Barberi, T., et al. (2005) co-cultured hESCs on mouse OP-9 stromal feeder layers and following 40 days of co-culture isolated CD73-positive cells (MSC-like cells) and replated them in the absence of the stromal cells. However, this method is limited by the extremely low yield of the MSC-like cells (only 5% of the cells were CD73-positive cells) and by the co-culturing of the hESCs on mouse feeder-layers, which complicates culturing procedures and limits the use for cell-based therapy.

Other approaches utilized embryoid bodies (EBs) in order to generate committed cells of the osteogenic lineage. Thus, intact or single cells of EBs were cultured in the presence of an osteogenic medium without cell passaging for more than 21 days resulting in cells which were terminally differentiated to the osteoblast lineage [Cao (Supra, 2005), Bielby (Supra, 2004) or Sottile (Supra, 2003)].

Thus, to date, there is no method of isolating ESC-derived connective tissue progenitor cells devoid of the above limitations.

While reducing the present invention to practice, the present inventors have uncovered an efficient method of generating connective tissue progenitor (CTP) cells from embryonic stem cells or embryoid bodies. As is shown in the Examples section which follows, the CTPs of the present invention are proliferative cells which can be expanded in culture for at least 25 passages while still differentiating to any one of a connective tissue type. In addition, as is further shown in the Examples section which follows, the CTPs of the present invention were capable of differentiating into the osteogenic lineage, the chondrogenic lineage, cartilage cells, tendon cells, ligament cells and ECM-forming cells. In addition, CTPs of the present invention were capable of forming a mature tissue such as a functional tendon without using any scaffold or carrier. Moreover, when transplanted into mice, the CTPs of the present invention were capable of forming a loose connective tissue, a bone tissue and a cartilage tissue in vivo.

Thus, according to one aspect of the present invention there is provided a method of generating connective tissue progenitor cells. The method is effected by culturing single embryonic stem cells (ESCs) in a culture medium which comprises cortisol and/or ascorbic acid so as to obtain connective tissue progenitor cells; thereby generating the connective tissue progenitor cells.

As used herein the phrase "connective tissue progenitor cells (CTPs)" refers to cells which are capable of differentiating to more than one cell lineage and/or cell type of a connective tissue. Examples of connective tissues include, but are not limited to dense connective tissue (e.g., ligament, tendon, periodontal ligament), areolar connective tissue (e.g., with proteinaceous fibers such as collagen and elastin), reticular connective tissue, adipose tissue, blood, bone, cartilage, skin, intervertebral disc, dental pulp, dentin, gingival, extracellular matrix (ECM)-forming cells, loose connective tissue and smooth muscle cells.

The phrase "embryonic stem cells" as used herein refers to embryonic cells which are capable of differentiating into cells of all three embryonic germ layers (i.e., endoderm, ectoderm and mesoderm), or remaining in an undifferentiated state. The phrase "embryonic stem cells" may comprise stem cells obtained from the embryonic tissue formed after gestation (e.g., blastocyst) before implantation (i.e., a pre-implantation blastocyst), extended blastocyst cells (EBCs) which are obtained from a post-implantation/pre-gastrulation stage blastocyst (see WO2006/040763), and embryonic germ (EG) cells which are obtained from the genital tissue of a fetus any time during gestation, preferably before 10 weeks of gestation. Preferred embryonic stem cells according to this aspect of the present invention are of a human or primate (e.g., monkey) origin.

As used herein the phrase "single embryonic stem cells (ESCs)" refers to discrete ESCs which are substantially devoid of large or small cells clumps, e.g., ESCs which do not contact other ESCs, or small aggregates of ESCs, and as such can be expanded while preventing their terminal differentiation to a particular cell lineage or cell type.

The embryonic stem cells of the present invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from a 5-7 day-old blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparing human ES cells see Thomson et al., (U.S. Pat. No. 5,843,780; Science 282: 1145, 1998; Curr. Top. Dev. Biol. 38: 133, 1998; Proc. Natl. Acad. Sci. USA 92: 7844, 1995); Bongso et al., (Hum Reprod 4: 706, 1989); and Gardner et al., (Fertil. Steril. 69: 84, 1998).

It will be appreciated that commercially available embryonic stem cells can be also used with this aspect of the present invention. Human ESCs can be purchased from the NIH human embryonic stem cells registry (http://escr.nih.gov). Non-limiting examples of commercially available embryonic stem cell lines are BG01, BG02, BG03, BG04, CY12, CY30, CY92, CY10, TE03 and TE32.

As mentioned, the method of generating connective tissue progenitor cells can also utilize ESCs which have undergone in vitro differentiation to form embryoid bodies (EBs).

As used herein the phrase "embryoid bodies (EBs)" refers to morphological structures comprised of a population of embryonic stem cells which have undergone differentiation (e.g., in vitro) following the removal of differentiation blocking factors. Preferably, the phrase "EBs" includes "simple EBs", i.e., EBs in which a layer of endodermal cells is formed on the outer layer of the small mass (e.g., EBs formed following 1-4 days of differentiation of human ESCs in culture), and "complex EBs", i.e., EBs which are characterized by extensive differentiation of ectodermal and mesodermal cells and derivative tissues (e.g., EBs formed following 3-20 days of differentiation of human ESCs in culture).

Preferred EBs according to this aspect of the present invention are of a human or primate (e.g., monkey) origin. Preferably, in order to generate connective tissue progenitor cells which are suitable for human therapeutic applications (e.g., cell based therapy), the EBs used by the method of this aspect of the present invention are of a human origin.

Preferably, the EBs used by the method of this aspect of the present invention are 1-day-old EBs, 2-day-old EBs or 3-day-old EBs, more preferably, 4-day-old EBs, more preferably, EBs derived from a later developmental stage such as at least 5-day-old EBs, preferably, between 5-25 day-old-EBs, more preferably, between 5-10 day-old EBs.

Thus, as mentioned the single ESCs or cell of EBs are cultured in a culture medium comprising cortisol and/or ascorbic acid.

Prior to culturing in the culture medium, colonies of the ESCs or the EBs are preferably dissociated to small cell clumps or even more preferably, to single cells (e.g., which are devoid of contact with other cells while in a liquid medium). Such colonies or clumps dissociation can be achieved by enzymatic digestion using, for example, type IV Collagenase (e.g., 0.1%, for 30-60 minutes at 37° C.) for ESC colonies or trypsin (e.g., 0.25% trypsin for 2-5 minutes at a temperature of 37° C.) for EBs, followed by an aggressive mechanical agitation of the dissociated cell clumps [e.g., by pipetting up and down thoroughly]. Once dissociated, the single cells resulting from the ESC colonies or the EBs can be isolated by filtration via a membrane which enables the passage of single cells while avoiding the passage of large cell clumps. For example, as described in the Examples section which follows, the present inventors have used a membrane with a cut-off of 40 μm [e.g., mesh cell strainer (Falcon)] in order to isolate single cells derived from ESC colonies or EBs. It will be appreciated that the incubation time and concentration of the digestion enzyme (e.g., collagenase or trypsin) used to dissociate the ESC colonies or the EBs depend on the size of the ESC colonies or the EBs, and measures are taken in order to dissociate the large cell aggregates to small cell clumps or preferably to single cells without hampering the cell structure and viability. Similarly, the strength (e.g., as controlled by the number of RPM) and period of the mechanical agitation can be also adjusted to achieve dissociation of large cell clumps while preserving cell morphology and viability. It will be appreciated that the morphology of the dissociated ESC colonies or EBs can be monitored using an inverted microscope and the viability of the cells can be measured by subjecting a sample of the cells to the Live/Dead viability assay (Molecular Probes, Molecular Probes, Inc., Eugene, Oreg., USA).

Culturing the single ESCs and/or the EBs according to this aspect of the present invention is effected by seeding the single ESCs and/or the cells of the EBs in a culture vessel (e.g., a tissue culture plate, flask, container or bottle) at a cell density which promotes cell survival and proliferation while maintaining the multipotent capacity of the CTPs. For example, a suitable cell density which can be used to generate the CTPs of the present invention may be $1 \times 10^5 - 1 \times 10^6$ cells per cm$^2$, more preferably, $5 \times 10^5 - 1 \times 10^6$ cells per cm$^2$ (e.g., $5 \times 10^5$ cells per cm$^2$). Culturing conditions usually include incubation of the cells at physiological temperatures in the range of 35-38° C. (preferably, 37° C.), under humidity and in the presence of 5% $CO_2$.

The culture medium used by the method of this aspect of the present invention may be any culture medium capable of supporting the growth of the CTPs of the present invention while maintaining their proliferative and multipotent capacities. Such a culture medium can be a water-based medium which includes a combination of substances such as salts, nutrients, minerals, vitamins, amino acids, nucleic acids, proteins such as cytokines, growth factors and hormones, all of which are needed for maintaining CTP proliferation and differentiation levels. For example, a culture medium according to this aspect of the present invention can be a synthetic tissue culture medium such as alpha-MEM (Biological Industries, Beit Haemek, Israel), Ko-DMEM (Gibco-Invitrogen Corporation products, Grand Island, N.Y., USA), DMEM/F12 (Biological Industries, Biet Haemek, Israel), supplemented with the necessary additives as is further described hereinunder. Preferably, all ingredients included in the culture medium of the present invention are substantially pure, with a tissue culture grade.

As used herein the term "cortisol" refers to a synthetic or naturally occurring cortison (a glucocorticoid steroid hormone) which binds the glucocorticoid receptor and is capable of expanding CTPs and maintaining their differentiation state. It will be appreciated that the method of this aspect of the present invention can use a variety of cortisol derivatives or analogues which are capable of the biological activity (e.g., expanding CTPs and maintaining their differentiation state). Non-limiting examples of cortisol derivatives or analogues which can be used according to this aspect of the present include hydrocortisone, cortisone acetate, prednisone, prednisolone, methylprednisolone, dexamethasone (about 40 times more potent), betamethasone, triamcinolone, beclometasone, fludrocortisone acetate and deoxycorticosterone acetate (DOCA). Preferably, the cortisol analogue used by the method of this aspect of the present invention is dexamethasone, which is known to have a potent activity (about 40 times more than hydrocortisone) mediated by the glucocorticoid receptor.

The dexamethasone which is included in the culture medium of this aspect of the present invention can be obtained from SIGMA (St Louis, Mo., USA) and is provided at a concentration selected from the range of $10^{-5}$-$10^{-8}$ M, e.g., at least $10^{-7}$ M. For example, as described under "General Materials and Experimental Methods" of the Examples section which follows, the present inventors have used $10^{-7}$ M dexamethasone within the culture medium to obtain a highly proliferative, multipotent CTPs.

As used herein "ascorbic acid" refers to the synthetic or naturally occurring ascorbic acid (an organic acid with anti-oxidant properties), also known as vitamin C, which is suitable for culturing cells (e.g., sterile preparation).

The ascorbic acid which is included in the culture medium of the method of this aspect of the present invention can be obtained from Sigma (St Louis, Mo., USA) and is provided at a concentration of at least 20 μg/ml, more preferably, at least 30 μg/ml, preferably, at a concentration which is selected from the range of 20-500 μg/ml, more preferably, at a concentration which is selected from the range of 20-200 μg/ml, more preferably, at a concentration which is selected from the range of 30-100 μg/ml, e.g., 50 μg/ml. For example, as described under "General Materials and Experimental Methods" of the Examples section which follows, the present inventors have used 50 μg/ml ascorbic acid within the culture medium to obtain a highly proliferative, multipotent CTPs.

As is shown in FIGS. 4a-e and is described in Example 3 of the Examples section which follows, the CTPs generated by the method of this aspect of the present invention are capable of forming mineralized matrix. Preferably, in order to increase the deposition of mineralized matrix (e.g., when differentiation into a bone tissue is desired), the culture medium further includes inorganic phosphate such as beta-glycerophosphate, which can be obtained from Sigma (St Louis, Mo., USA). The inorganic phosphate included in the culture medium is provided at a concentration in the range of 0.01-1000 mM, preferably, at a concentration of 1-50 mM, even more preferably, at a concentration of 10 mM.

Preferably, the culture medium used according to the method of this aspect of the present invention further comprises serum or serum replacement (e.g., a defined preparation made of mainly synthetic or recombinantly expressed proteins which replaces the serum in a culture medium). Such sera can be derived from a human source (human serum) or from an animal source (e.g., bovine serum, horse serum) and can be obtained from a variety of tissue culture suppliers such as Hyclone (Utah, USA), Invitrogen (Grand island, NY, USA) or Biological Industries (Bet Haemek, Israel). A preparation of serum replacement can be obtained from Gibco-Invitrogen Corporation (Grand Island, N.Y. USA).

The serum or serum replacement used by the method of this aspect of the present invention is provided at a concentration range of 1% to 40%, more preferably, 5% to 35%, more preferably, 10% to 30%, more preferably 10% to 20%, e.g., 15%.

Preferably, culturing according to this aspect of the present invention is effected under xeno-free culturing conditions, i.e., under conditions which are devoid of animal contaminants (e.g., animal pathogens such as retroviruses). Thus, the serum which is included in the culture medium of the present invention is preferably human serum or serum replacement, and culture medium additives (e.g., the growth factors, minerals, vitamins or hormones such as dexamethasone and ascorbic acid) are preferably synthetic or recombinantly expressed highly pure additives.

It will be appreciated that the CTPs of the present invention can grow in the above-described culture medium by either directly attaching to the wall of the culture vessel (e.g., the bottom of a culture flask) or by attaching to feeder cells which are attached to the wall of the culture vessel. Feeder cells are cells such as stromal cells, fibroblast cells (e.g., foreskin fibroblasts, human embryonic fibroblasts) or human fallopian epithelial cells, which secrete growth factors and/or nutrients and support the growth of the cells-of-interest (e.g., stem or progenitor cells) cultured therewith. However, it will be appreciated that culturing conditions which rely on feeder cells are much more complicated since they require the separation of the cells-of-interest from the feeder cells at each passaging step and thus may result in mixed populations of cells.

Preferably, culturing according to the method of this aspect of the present invention is effected under feeder-free culturing conditions. As used herein the phrase "feeder-free culturing conditions" refers to culturing conditions which are devoid of feeder cells. For example, as shown in the Examples section which follows, the CTPs of the present invention (which are cultured under feeder-free culturing conditions) are completely devoid of feeder cells and thus represent a pure population of CTPs.

Preferably, the method of this aspect of the present invention further comprises expanding the CTPs. As used herein the phrase "expanding" refers to increasing the number of the connective tissue progenitor cells over the culturing period without hampering their differentiation capacity.

Preferably, the method of this aspect of the present invention further comprises serial passaging of the cells in culture (i.e., the splitting of the cells so that the cells can grow beyond confluency). The term "confluency" as used herein refers to a density of adherent cells which when attached to a wall of a culture vessel cover 100% of its area. Preferably, in order to prevent the differentiation of the CTPs of the present invention to terminally differentiated cells (e.g., osteoblasts) or to cells with limited differentiation potential (e.g., precursors which are restricted to a specific cell lineage), the first passaging occurs when the cells in the culture reach subconfluency, i.e., when the cells cover about 70-90% of the culture vessel wall, more preferably, when the cells cover about 80-90% of the culture vessel wall. Preferably, when cultured according to the teachings of the present invention subconfluency of the cells in the culture occurs no more than 10 days of the initial seeding of the cells. Preferably, the cells are serially passaged after no more than 9 days in culture, more preferably, after no more than 8 days in culture, more preferably, after no more than 7 days in culture, more preferably after about 4-6 days in culture.

Passaging according to this aspect of the present invention can be performed by dissociating cells from the wall of the culture vessel using e.g., type IV collagenase (at a concentration of 0.1% for 20-60 minutes) followed by trypsinization (using 0.25% μg/ml trypsin for 2-5 minutes), counting the single cells and splitting the cells to 2-5, preferably to 4 tissue culture vessels (i.e., a splitting ratio of 1:4) in order to preserve the same cell density of their initial seeding (e.g., $5 \times 10^5$-$1 \times 10^6$ cells per cm$^2$). Preferably, the cell culture is subjected to culture passaging every 3-6 days, preferably, culture passaging occurs every 2-5 days, e.g., every 4 days.

Preferably, passaging according to the method of this aspect of the present invention is performed for at least 20 times, more preferably, at least 25 times, more preferably, at least 30 passages, while splitting the cells using a splitting ratio of 1:3, more preferably, a splitting ratio of 1:4. As is shown in FIG. 1a and is described in Example 1 of the Examples section which follows, the CTPs of the present invention were serially passaged every 4 days for at least 25 passages.

Preferably, passaging according to the method of this aspect of the present invention is effected under xeno-free and/or feeder-free conditions.

In addition, the method of this aspect of the present invention preferably comprises a step of isolating the CTPs (i.e., separating the CTPs from the culture medium). Isolating the cells can be effected at any time while in culture, e.g., prior to the first culture passaging, following the first culture passaging, or following any other culture passaging. Thus, the CTPs can be isolated by filtration (e.g., using a membrane which prevents the passage of CTPs and enables passage of the medium and/or by centrifugation of the cells (e.g., using the conical tube centrifugation at 1500 RPM).

Preferably, CTPs generated and isolated according to the method of this aspect of the present invention are highly proliferative cells. For example, hESCs-derived CTPs exhibited a tripling time (i.e., the hours between passages in which the cell number was triplicated) of 80-100 hours during passages 1-18 and of 120-140 hours during passages 19-25 (FIG. 1a, Example 1 of the Examples section which follows).

As is shown in FIGS. 3a-k and is described in Example 2 of the Examples section which follows, FACS analysis revealed that about 42% of the CTPs isolated according to the method of this aspect of the present invention express CD105 (a marker of endothelial cells, also known as Endoglin, GenBank Accession No. NP_000109.1) on their cell surface. This is in contrast to the ESC-derived MSC-like cells obtained by the methods of Barberi T., et al. (Supra, 2005) and Olivier E. N., et al. (Supra, 2005) which comprised of 81 and 100%, respectively, of CD105-expressing cells. Thus, these results demonstrate that the CTPs generated according to the teachings of the present invention represent a novel isolated cell preparation of connective tissue progenitors.

Thus, according to another aspect of the present invention there is provided an isolated cell preparation of connective tissue progenitor cells comprising a first population of cells expressing CD105 and a second population of cells not expressing CD05, wherein a ratio between the first population of cells and the second population of cells is between about 0.6 to about 1.5.

As used herein the phrases "expressing" or "not expressing" refer to cells having a positive (+) or negative (−) expression profile, respectively, of a certain marker (e.g., gene or gene product).

Preferably, the ratio between the cells expressing CD105 and the cells not expressing CD105 is between about 0.6 to about 1.3, more preferably, between about 0.6 to about 1, more preferably, between about 0.7 to about 0.9, more preferably, between about 0.7 to about 0.8 (e.g., 0.72).

As is further shown by the FACS analysis depicted in FIGS. 3a-k, the CD105-expressing cells also express CD166 (activated leukocyte cell adhesion molecule, also known as ALCAM, GenBank Accession No. NP_001618.2). On the other hand, the CD105-not expressing cells (having CD105 negative expression profile) include a majority of CD166-positive cells and a small fraction (5%) of CD166-negative cells. In addition, as is further shown in FIGS. 3a-k the CTPs of the present invention express CD44 (e.g., GenBank Accession No. NP_000601.3, NP_001001389.1, NP_001001390.1, NP_001001391.1, NP_001001392.2), CD29 (ITGB1 e.g., GenBank Accession No. NP_002202.2, NP_391987.1, NP_391989.1, NP_391988.1, NP_596867.1, NP_389647.1) and HLA-ABC and not expressing CD45 (PTPRC; e.g., GenBank Accession No. NP_002829.2, NP_563579.1, NP_563578.1, NP_563580.1) and HLA-DR, which resembles the expression pattern of adult MSCs.

As mentioned, the isolated cell preparation of connective tissue progenitor cells of this aspect of the present invention are not terminally differentiated cells, i.e., they are capable of differentiating to more than one cell lineage. For example, as is shown in FIGS. 2a-u, 22a-b and is described in Example 2 of the Examples section which follows, hESCs-derived CTPs from various passages (e.g., from passages 1-25) express markers of osteogenic lineage, the chondrogenic lineage, cartilage cells, tendon cells, ligament cells and ECM-forming cells. Moreover, as is shown in FIGS. 4a-e and is described in Example 3 of the Examples section which follows, when cultured in vitro in the presence of inorganic phosphate, hESCs-derived CTPs formed bone nodules (bone tissue) containing calcium-phosphate deposits, the major component of bone minerals. In addition, when induced to differentiate into the chondrogenic lineage (using the "intact layer" method), hESCs-derived CTPs formed a fibrous ECM (FIGS. 5c and 7a-f, Examples 4 and 5 of the Examples section which follows).

Thus, while further reducing the present invention to practice, the present inventors have uncovered that the CTPs of the present invention can be used to generate a connective tissue.

Preferably, the connective tissue which can be formed from the CTPs of the present invention is a bone tissue (e.g., osseous tissue), a connective tissue (e.g., loose connective tissue), an extracellular matrix (ECM), a tendon tissue, a ligament tissue and a cartilage tissue.

For example, to form a bone tissue, the isolated cell preparation of the CTPs of the present invention are cultured in a medium containing dexamethasone, ascorbic acid and inorganic phosphate (e.g., α-MEM supplemented with 15% serum, $10^{-7}$ M dexamethasone, 50 μg/ml ascorbic acid and 10 mM β-glycerophosphate) and let to become over-confluent (i.e., they occupy more than 100% of the area of the culture vessel wall and thus form multilayers) for a period of at least 10 days before mineralization appears. The culture medium is occasionally replaced every 4-8 days without culture passaging. The presence of bone tissue can be determined by RNA-based methods (e.g., RT-PCR, in situ RNA hybridization and cDNA microarray) or protein-based methods (e.g., immunological staining) for bone specific markers such as core binding factor alpha 1 (CBFA1), SOX9, type I collagen (Col-I), osteonectin, osteopontin, parathyroid hormone receptor 1 (PTHR1) and alkaline phosphatase. In addition, the ultra-structural and chemical data of bone tissue can be determined using, for example, energy dispersive spectroscopy (EDS), scanning electron microscopy (SEM) and/or confocal Raman spectroscopy (CRS) analyses essentially as described elsewhere [Ubelaker D H, et al., J Forensic Sci. 2002 September; 47(5):940-3; van Apeldoorn A A, et al., J R Soc Interface. 2005 Mar. 22; 2(2):39-45].

For the formation of connective tissue, the isolated cell preparation of the CTPs of the present invention are preferably seeded on a suitable 3D environment (e.g., a scaffold such as an electrospun, PCL/PLA nanofiber scaffold) that would support their growth and organization into a complex connective tissue which produces ECM. Briefly, $5 \times 10^5$ CTPs resuspended in 10 µl of CTP medium (α-MEM supplemented with 15% serum, $10^{-7}$ M dexamethasone, 50 µg/ml ascorbic acid) are seeded on a scaffold and grown in the presence of the CTP medium for about one month. The presence of connective tissue and ECM can be determined by RNA or protein-based methods for markers such as type III (Col-III) and type XII (Col-XII) collagens, decorin, biglycan, elastin, fibronectin, and tenascin-C, as well as using scanning electron microscopy (SEM) analysis.

For the formation of extracellular matrix (ECM), the isolated cell preparation of CTPs are plated at high densities in tissue culture plates in the presence of a culture medium comprising ascorbic acid and preferably also dexamethasone. After about 4 weeks in culture (other periods of time are also possible) sheet-like tissue is formed. The sheet-like tissue can be further subject to freeze-drying and/or cell removal as described in Example 10 of the Examples section which follows.

For the formation of ligament-forming cells, the isolated cell preparation of the CTPs of the present invention are cultured for at least one week in the presence of medium containing dexamethasone and ascorbic acid (e.g., α-MEM supplemented with 15% serum, $10^{-7}$ M dexamethasone, 50 µg/ml ascorbic acid). The presence of ligament-forming cells can be detected by RNA or protein-based methods for markers such as scleraxis and type I Collagen.

For the formation of a cartilage tissue, two main methods can be employed: the "intact layer" method (removal of sub-confluent CTP cultures without pre-collagenase treatment and culturing the intact layer in a CTP medium, essentially as described in the Examples section) and the "pellet culture" method (spherical pellets which are cultured in medium supplemented with serum, dexamethasone, ascorbate-2-phosphate and TGF-β3; essentially as described in the Example section). The presence of cartilage tissue can be detected by RNA or protein-based methods for markers such as chondroitin sulfate proteoglycan 4 (CS4), type X collagen, and cartilage oligomeric matrix protein (COMP).

As described in the Examples section which follows, the present inventors have devised a long-term, high-density culture technique for the formation of a tendon and ligament tissues. Thus, the CTPs of the present invention were cultured in vitro at a cell density of $5-10 \times 10^6$ cells/cm$^2$ in the presence of a culture medium containing alpha-MEM supplemented with 15% FBS, 50 µg/ml ascorbic acid and $10^{-7}$ M dexamethasone. Cultures were kept for long periods of up to 4 months in culture, with no further splitting. As is shown in FIGS. 8a-b, 9a-d, 10a-c, 11a-d and is described in Example 6 of the Examples section which follows, tendon tissues formed in vitro included organized, parallel-aligned cells that express type I collagen and exhibit high matrix-to-cell ratio. Moreover, such tendon tissues exhibited mechanical properties which are similar to the native tendon tissues (FIG. 12, Table 3 and Example 6).

Thus, according to yet another aspect of the present invention there is provided a method of generating a tendon or a ligament tissue in vitro.

The method is effected by culturing the CTPs of the present invention in a culture medium which comprises ascorbic acid and/or dexamethasone under culture conditions devoid of a carrier, thereby generating the tendon or the ligament tissue.

The term "carrier" refers to any scaffold, bead, polymer or matrix which supports the attachment of cells thereto. The phrase "devoid of a carrier" as used herein refers to any culture conditions which enable the attachment of the CTPs directly to the culture vessel wall and not to a carrier (e.g., a scaffold). This is in sharp contrast to all known methods of generating tendon tissues in vitro, which are based on seeding cells-of-interest (e.g., non-genetically modified cells) onto a scaffold or a polymer suitable for tissue formation.

Preferably, the culture medium used for generating the tendon or the ligament tissue comprises ascorbic acid (e.g., between 1-500 µg ml, preferably, about 50 µg/ml) and/or dexamethasone (e.g., between $10^{-5}$-$10^{-8}$ M, preferably, about $10^{-7}$ M).

Preferably, culturing according to the method of this aspect of the present invention is effected without cell passaging for culturing periods which vary between a few weeks to several months (e.g., between 4 weeks to 6 months). Preferably, the culture medium is occasionally replaced, e.g., every 2-7 days (e.g., every 4 days). It will be appreciated that the process of tendon or ligament tissue formation begins as a single cell attaching to the culture plate side wall, forming fibrous matrix with a tendon-like shape.

The presence of a functional tendon or ligament tissue can be determined using histological staining, immunological assays (e.g., using an anti-type I collagen antibody), electron microscopy (e.g., SEM and TEM analyses) and mechanical evaluation using the stress strain test, essentially as described in the Examples section which follows.

It will be appreciated that for engineering of a particular tissue-of-interest (e.g., a tendon or a ligament), the culturing period of the cells may vary (e.g., become shorter) such that following the formation of a sheet-like tissue (e.g., following 4-5 weeks), the sheet-like tissue is removed from the culture vessel (using e.g., a cell scraper) and further rolled or folded to form the engineered tissue-of-interest (e.g., tendon, ligament). It will be appreciated that due to the culturing conditions employed according to this aspect of the present invention, which result in a tissue with high matrix to cells ratio, removal of the sheet-like tissue can be easily performed while preserving the intact tissue structure.

For example, as is illustrated in FIGS. 16a-e and is described in Example 9 of the Examples section which follows, following 4-5 weeks in the high density culture the formed sheet-like tissue was removed and rolled to form a rounded cylinder. The resulting tendon tissues were cylinder-shaped constructs, with typical ultrastructure characteristics and biomechanical properties of early tendons.

It will be appreciate that tissues which are formed in vitro from the isolated CTPs of the present invention (engineered tissues) can be further implanted in a subject in need thereof (e.g., a subject in need of a CTP-derived tissue formation, regeneration and/or repair) using techniques known in the art (e.g., using a surgical tool such as a scalpel, spoon, spatula, suture device, or other surgical device) to thereby regenerate, replace and/or repair the tissue-of-interest.

For example, as is shown in FIGS. 16a-e, 17a-d, 18a-c, 19a-b, 20a-c, 21a-c, 24a-b and 25b and is described in Example 9 of the Examples section which follows, the present inventors were capable of repairing a critical Achilles-tendon injury in mice. Thus, the implanted tendon grafts were remodeled and exhibited excellent biomechanical properties. Moreover, the implanted tendon grafts were functional in vivo as evidenced by the increased ankle extension following transplantation of a tendon graft instead of the injured Achilles tendon.

While further reducing the present invention to practice, the present inventors have uncovered that the connective tissue progenitor cells obtained according to the method of this aspect of the present invention can be used for in vivo cell-based therapy.

As described in Example 7 of the Examples section which follows, when the ESCs-derived CTPs of the present invention were implanted underneath the kidney capsule of SCID-beige mice a localized sub-capsular formation of loose connective tissue was observed. In addition, as described in Example 8 of the Examples section which follows, when the ESCs-derived CTPs were subcutaneously transplanted into cd1 nude mice, ectopic new bone and cartilage tissues were formed. The ectopic tissues were well vascularized and biocompatible (FIG. 13c) and included radio-opaque bone tissue (FIGS. 13a-b). Further histological analyses of the ectopic tissues confirmed the formation of new bone (FIGS. 14a-c, 15a-b) and hypertrophic cartilage (FIGS. 14d-e) tissues.

Thus, according to yet another aspect of the present invention there is provided a method of in vivo forming or generating a connective tissue. The method is effected implanting in a subject in need therefore the connective tissue progenitor cells of the present invention; thereby in vivo forming the connective tissue.

The phrase "in vivo" refers to forming a tissue within a living organism such as a plant or an animal, preferably in mammals, preferably, in human subjects.

The phrase "a subject in need thereof" as used herein refers to a mammal, preferably a human being at any age who is in need of a connective tissue such as for tissue construction, repair, regeneration or replacement. For example, such a subject can suffer from a diseased, degenerated, injured or broken tissue or may be missing a particular tissue.

Preferably, the connective tissue which can be formed in vivo according to the method of this aspect of the present invention include bone tissue, cartilage tissue and loose connective tissue.

Implanting the CTPs in the subject can be performed using methods known in the art such as by administering or injecting the CTPs with a syringe needle, catheter or cannula. The cells are preferably administered near or at the site-of-interest (e.g., bone, cartilage, connective tissue) within the subject (e.g., at the site of the damaged or injured tissue) and thus can be used to repair bone fracture, diseased or damaged cartilage, bone or connective tissue. It will be appreciated that in some cases alternative sites may be used. In addition, it will be appreciated that the cells can be administered as an isolated cell preparation (cell therapy) or can be first seeded on a scaffold and then administered to the subject (engineered tissue therapy).

The present invention further contemplates monitoring the formation, regeneration or repair of the connective tissue following implantation. For example, the formation of new bone tissue can be monitored by X-ray and/or CT analysis; the formation of a new tendon tissue can be monitored by MRI; the formation of a new connective tissue can be monitored by MRI. Alternatively, the formation of new tissue can be evaluated by physiological assays such as extension of a tendon, strength of a bone and the like.

Preferably, in order to prevent the induction of immune response within the recipient subject, the CTPs of the present invention may be encapsulated in immunoisolating, semipermeable membranes.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002; 13: 783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

The isolated cell preparation of CTPs of the present invention may also form part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the isolated cell preparation of connective tissue progenitor cells of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Thus, the teachings of the present invention can be used for various therapeutic applications such as tendon and ligament repair, bone regeneration, cartilage regeneration, tissue augmentation, tissue reconstruction (mediated or assisted by the CTPs of the present invention) such as deep wound healing, burn wound dressing and skin regeneration, skin fillers, orthodontic procedures, sling procedures and fascia reconstruction.

The present invention further contemplates an article-of-manufacture which comprises packaging material and a composition comprising the isolated cell preparation of CTPs of the present invention along with instructions for use in cell based therapy, tissue repair, reconstruction, regeneration and/or replacement.

The present invention further contemplates an article-of-manufacture which comprising packaging material and a tissue graft generated in vitro from the CTPs of the present invention along with instructions for using the tissue graft for tissue repair, regeneration and/or replacement.

The present invention further contemplates the use of the CTPs of the present invention for the preparation of intact ECM (non-conditioned or conditioned) for specialized tissue regeneration/regeneration as well as purified ECM components for tissue regeneration, anti-aging medicine related applications.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Cell Culture—Undifferentiated hESCs (I3, I6 and H9.2 cell lines, passages 30-50) were grown on mitotically inactivated mouse embryonic fibroblast (MEF) feeders, in 80% knockout Dulbecco's modified eagle's medium (DMEM, Invitrogen), supplemented with 20% knockout serum replacement, 1 mM L-glutamine, 1% non essential amino acids, 0.1 mM 2-mercaptoethanol and 4 ng/ml basic fibroblast growth factor (bFGF) (all from Invitrogen). Four different independent sets of cultures were performed, twice for each hESC line. For controls, primary human fetal stem cells were isolated from nine-week gestational age old fetus following voluntary interruption of pregnancy, essentially as described before (Montjovent, M. O. et al, 2004).

EB formation—To induce embryoid body (EB) formation, hESC colonies were subjected to type IV collagenase treatment, removed from the MEF feeders and allowed to aggregate in suspension, in a medium containing 80% knockout DMEM, 20% fetal bovine serum (Hyclone), 1 mM glutamine and 1% non essential amino acids (both from Invitrogen).

Connective tissue progenitors (CTPs) derivation and propagation from EBs—Four to 20 days-old EBs (e.g., 10-day-old) were enzymatically digested with trypsin (0.25% please indicate trypsin concentration for 2-5 minutes at 37° C.) followed by aggressive mechanical agitation, and passed through a 40 μm mesh cell strainer (Falcon) to obtain a single cell suspension. Cells were then counted and seeded on tissue culture-treated flasks at a density of $5\times10^5$ cells per $cm^2$. Twelve hours later, the medium was changed to a CTP medium, containing alpha-MEM (Biological Industries, Kibbutz Beit Haemek, Israel) supplemented with 15% FBS (selected lots, Hyclone), 50 μg/ml ascorbic acid (Sigma, St Louis, Mo., USA) and $10^{-7}$ M dexamethasone (Sigma, St Louis, Mo., USA). Upon reaching sub-confluence (about 5-10 days), cultures were incubated with type IV collagenase followed by trypsinization, and passaged every 3-4 days.

Assessment of clonality was preformed though a separate expansion of singe cells taken during routine passaging and plating them in single tissue culture wells (24 cells into 24 wells) and the ability of the single cells to form a cell colony was evaluated every day during a week. The growth kinetics and cellular phenotype (assessed by RT-PCR) were evaluated. For controls, fetal isolated cells were grown with CTP medium and passaged in a similar way.

Connective tissue progenitors (CTPs) derivation and propagation from hESCs—hESCs colonies were enzymatically digested with type IV Collagenase (0.1 %, for 30-60 minutes at 37 C) followed by aggressive mechanical agitation, and passed through a 40 μm mesh cell strainer (Falcon) to obtain a single cell suspension. Cells were then counted and seeded on tissue culture-treated flasks at a density of $5 \times 10^5$ cells per cm². Twelve hours later, the medium was changed to a CTP medium, containing alpha-MEM (Biological Industries, Kibbutz Beit Haemek, Israel) supplemented with 15% FBS (selected lots, Hyclone), 50 μg/ml ascorbic acid and $10^{-7}$ M dexamethasone. Upon reaching sub-confluence (about 5-10 days), cultures were incubated with type IV collagenase followed by trypsinization, and passaged every 3-4 days. Assessment of clonality was preformed though a separate expansion of singe cells taken during routine passaging as described hereinabove. For controls, fetal isolated cells were grown with CTP medium and passaged in a similar way.

Osteogenic differentiation and matrix formation—For induction of mineralization, CTPs were grown with CTP medium supplemented with 10 mM beta-glycerophosphate (inorganic phosphate), and let to become over-confluent for period of at least 10 days before mineralization appears.

Chondrogenic Differentiation

Method 1: the "intact layer" method, formerly called "spontaneous"—Sub-confluent CTP cultures (from any passage, e.g., 1-13) were removed from the culture plates (without pre-collagenase treatment) as an intact layer, were placed in suspension and were fed with the CTP medium described hereinabove. This method generates typical cartilage morphology.

Method 2: the pellet culture system, formally called "directed"—Sub-confluent CTP cultures (from any passage) were re-suspended at a density of $2 \times 10^5$ cells/ml (the density can vary), dispensed into 15-ml conical tubes and centrifuged for 5 minutes at 1,200 rpm to form spherical pellets. The pellets were further cultured in medium containing 1% serum in addition to high-glucose Dulbecco's modified Eagle's medium supplemented with $10^{-7}$ M dexamethasone, 50 μg/ml ascorbate-2-phosphate, 40 μg/ml L-proline, 100 μg/ml sodium pyruvate, 50 mg/ml ITS+Premix (Collaborative Biomedical: 6.25 μg/ml insulin, 6.25 μg/ml transferrin, 6.25 ng/ml selenious acid, 1.25 mg/ml bovine serum albumin, and 5.35 mg/ml linoleic acid) and 10 ng/ml TGF-β3. This method induced up-regulation of specific cartilage matrix genes such as Col-X, COMP and CS4 (FIGS. 6a-d).

RT-PCR analysis—Total RNA was isolated using the TRIzol Reagent (Invitrogen, Carlsbad, Calif. USA) according to the manufacturer's instructions. cDNA was reverse transcribed from 1 μg total RNA with M-MLV Reverse Transcriptase (Promega, Madison, Wis. USA). PCR conditions were optimized for each set of primers and the number of PCR cycles was confirmed to be in the linear range of amplification. The amplified products were separated on 2% agarose gel stained with ethidium bromide and identified by size. The identity of each product was confirmed by restriction enzyme digestion. Samples not treated with reverse transcriptase and no-template samples were used as controls. Table 1, hereinbelow, summarizes the primer sequences (along with their SEQ ID NOs), annealing temperatures, cycle numbers used for RT-PCR, the restriction enzyme used to verify the identity of RT-PCR products (along with the expected size of the digested product).

TABLE 1

RT-PCR primers and conditions

| Gene (GenBank Accession No.) | Forward (F) and Reverse (R) (SEQ ID NO:) 5'→3' | Cyc. | Ann. | Restr. Enzyme | RT-PCR product size |
|---|---|---|---|---|---|
| CBFA1 (NM_004348) | CBFA1 F: CCGCACGACAACCGCACCAT (SEQ ID NO: 1) CBFA1 R: CGCTCCGGCCCACAAATCTC (SEQ ID NO: 2) | 40 | 62° C. 30 sec | SacI 215 bp | 283 bp |
| SOX9 NM 000346 | Sox9 F: ATCTGAAGAAGGAGAGCGAG (SEQ ID NO: 3) Sox9 R: TCAGAAGTCTCCAGAGCTTG (SEQ ID NO: 4) | 35 | 58° C. 30 sec | EcoRII | 264 bp |
| COLI NM 000089.3 | hCOLI F: GCACACAATGGATTGCAAGG (SEQ ID NO: 5) hCOLI R: TAACCACTGCTCCACTCTGG (SEQ ID NO: 6) | 35 | 64° C. 30 sec | NcoI 39 bp BclI 45 bp | 476 bp |
| ONEC NM 003118 | Onec F: GCAGCAATGACAACAAGACC (SEQ ID NO: 7) Onec R: CTTCTCATTCTCATGGATCTTC (SEQ ID NO: 8) | 35 | 58° C. 30 sec | SphI 166 bp | 277 bp |

TABLE 1-continued

RT-PCR primers and conditions

| Gene (GenBank Accession No.) | Forward (F) and Reverse (R) (SEQ ID NO:) 5'→3' | Cyc. | Ann. | Restr. Enzyme | RT-PCR product size |
|---|---|---|---|---|---|
| OPN NM_000582.2| | hOPN F: CTAGGCATCACCTGTGCCATACC (SEQ ID NO: 9) hOPN R: CAGTGACCAGTTCATCAGATTCATC (SEQ ID NO: 10) | 30 | 55° C. 56 sec | EcoRII | 330 bp 226 bp |
| ALP NM 000478 | ALP F: TGGAGCTTCAGAAGCTCAAC (SEQ ID NO: 11) ALP R: ATCTCGTTGTCTGAGTAGTACCAGTCC (SEQ ID NO: 12) | 35 | 62° C. 30 sec | BstXI | 435 bp 120 bp |
| Hpth/r1 NM 000316 | hPTH/R F: CACAGCCTCATCTTCATGG (SEQ ID NO: 13) hPTH/R1 R: GCATCTCATAGTGCATCTGG (SEQ ID NO: 14) | 35 | 60° C. 45 sec | SacI | 417 bp 148 bp |
| COL9 α2 (17/11) NM_001852.3| | Col9/2 F: TGGTTTAACTGGAGCCAAGG (SEQ ID NO: 15) Col9/2 R: GCCCACCATGAATTTATATC (SEQ ID NO: 16) | 35 | 60° C. 30 sec | SphI | 520 bp 330 bp |
| COL10 NM 000493 | COL10 F: CCCTTTTTGCTGCTAGTATCC (SEQ ID NO: 17) COL10 R: CTGTTGTCCAGGTTTTCCTGGCAC (SEQ ID NO: 18) | 40 | 60° C. 30 sec | XhoI | 468 bp 194 bp |
| COMP (NM_000095) | COMP F: CAGGACGACTTTGATGCAGA (SEQ ID NO: 19) COMP R: AAGCTGGAGCTGTCCTGGTA (SEQ ID NO: 20) | 35 | 57.5° C. 30 sec | BstXI | 314 bp 141 bp |
| AGGRECAN NM 001135 | AGN F: ATCCGAGACACCAACGAGAC (SEQ ID NO: 21) AGN R: GGCTTCACCCTCACTGATGT (SEQ ID NO: 22) | 35 | 60° C. 30 sec | SphI | 477 bp 290 bp |
| CS4 NM 001897 | CS-4S F: CCCCCATCCTCACTACAAAC (SEQ ID NO: 23) CS-4S R: ATCCAGGGTTCCTCTGTGTG (SEQ ID NO: 24) | 40 | 60° C. 30 sec | PstI | 242 bp 34-38 bp |
| SCLER BK000280.1| | Scler F: TGCAAGCTTCCCTTTTCAGT (SEQ ID NO: 25) Scler R: CTGCACAGCCGAAATTGTAA (SEQ ID NO: 26) | 40 | 60° C. 30 sec | HgaI | 455 bp 292 bp |
| COL3 NM_000090.2| | Col3 F: CCTCCAACTGCTCCTACTCG (SEQ ID NO: 27) Col3 R: CGGGTCTACCTGATTCTCCA (SEQ ID NO: 28) | 35 | 60° C. 30 sec | BglI | 439 bp 266 bp |
| collagen, type XII NM 004370 | Col-XII F: GTGCCTGGACTGATTTGGTT (SEQ ID NO: 29) Col-XII R: | 35 | 60° C. 30 sec | ScaI StyI | 464 bp 185 bp 414 bp |

TABLE 1-continued

RT-PCR primers and conditions

| Gene (GenBank Accession No.) | Forward (F) and Reverse (R) (SEQ ID NO:) 5'→3' | Cyc. | Ann. | Restr. Enzyme | RT-PCR product size |
|---|---|---|---|---|---|
| | TGTGGAGGCAATTTGTTTGA (SEQ ID NO: 30) | | | | |
| DECOR NM_001920.3| | Décor F: TGAAGAACCTTCACGCATTG (SEQ ID NO: 31) Décor R: GAGCCATTGTCAACAGCAGA (SEQ ID NO: 32) | 35 | 60° C. 30 sec | SacI 255 bp | 481 bp |
| BIGLY NM_001711.3| | Bigly F: TGCAGAACAACGACATCTCC (SEQ ID NO: 33) Bigly R: CCAGGTTCAAAGCCACTGTT (SEQ ID NO: 34) | 35 | 60° C. 30 sec | BstXI 192 bp | 319 bp |
| ELAST NM_000501.1| | Elast F: GCTATGGACTGCCCTACACC (SEQ ID NO: 35) Elast R: AGCTCCTGGGACACCAACTA (SEQ ID NO: 36) | 40 | 60° C. 30 sec | BglI 288 + 329 bp | 371 bp |
| FIBRO NM 212482 | Fibro F: GGAGTCAGCTGCCAAGAGAC (SEQ ID NO: 37) Fibro R: ACACACGTGCACCTCATCAT (SEQ ID NO: 38) | 35 | 60° C. 30 sec | XhoI 215 bp | 482 bp |
| TEN C NM 002160 | Ten F: CGTGGAGTACCTTGTCAGCA (SEQ ID NO: 39) Ten R: AGGTAACCGGTGACTGATGC (SEQ ID NO: 40) | 35 | 60° C. 30 sec | XhoI 252 bp | 438 bp |

Table 1: Primers used to amplify RT-PCR products of the noted genes (are referred to using GenBank Accession Nos.) are provided along with the PCR annealing (Ann.) conditions, number of PCR cycles (Cyc.), the size of PCR products and the restriction enzyme (Restr. Enzyme) and digestion product used to verify the identity of the RT-PCR product.

Microarray analysis—For cDNA microarray analysis, isolated total RNA from undifferentiated hESCs (H9.2), fetal CTPs (passage 1) and hESC-derived CTPs grown in the presence of the CTP medium (passages 1 and 9) were reverse transcribed with M-MLV Reverse Transcriptase (Promega, Madison, Wis. USA) using Biotin-16-dUTP (Roche, Mannheim, Germany). The array membranes (GEArray Q Series Human Osteogenesis Gene Array HS-026, SuperArray Bioscience Corp., Frederic, Md. USA) were pre-hybridized for 2 hours with heat-denatured salmon sperm DNA (Invitrogen) at a final concentration of 100 μg/ml according to the manufacturer's instructions. The membranes were hybridized overnight with Biotin-16-dUTP-labeled cDNA probes, and then washed twice for 15 minutes each in a solution of 2×SSC, 1% SDS followed by two washes of 15 minutes each in a solution of 0.1×SSC, 0.5% SDS. All steps were performed at 60° C. with continuous agitation. Chemiluminescent detection was performed using the Chemiluminescent Detection Kit (SuperArray Bioscience Corp., Frederic, Md. USA) according to the manufacturer's instructions. The membranes were blocked for 40 minutes with a GEAblocking solution Q. Binding of alkaline phosphatase-conjugated streptavidin was performed by incubating the membranes for 10 minutes in a binding buffer. The membranes were then washed four times, for 5 minutes each, with 1× Buffer F and rinsed twice with Buffer G, followed by incubation of 2-5 minutes with CDP-star chemiluminescent substrate. All steps were performed at room temperature with continuous agitation. The signal was detected using X-ray film.

Karyotype analysis—For karyotype analyses, standard G banding was performed on undifferentiated hESCs and CTPs (passage 8-10) essentially as described elsewhere (Amit, M. et al, 2000).

Electron Microscopy—For transmission electron microscopy (TEM) cells were fixed in 3% glutaraldehyde in 0.1 M sodium cacodylate buffer pH=7.4, post-fixed with 1% $OsO_4$ and in 2% uranyl acetate, gradually dehydrated in ethanol series and embedded in Epon 812. Ultrathin sections (70 to 90 nm) cut on an ultramicrotome (Leica UCT) were mounted on grids, stained with lead-citrate, and then examined with a Tecnai 12 transmission electron microscope under 120 kV. Pictures were digitized with CCD Megaview III and analyzed with analySIS software (Soft Imaging System).

Scanning electron microscopy (SEM)—For SEM, cells and cell-seeded scaffolds were fixed in 3% glutaraldehyde in 0.1 M sodium cacodylate buffer pH=7.4, followed by gradual dehydration in ethanol series and drying using hexamethyldisilazane (HMDS) (Sigma). Samples were sputter coated with carbon and viewed under LEO field-emission scanning electron microscope for imaging and energy dispersive spectroscopy (EDS) analysis.

Cytochemistry and electron microscopy—For histological analyses, cells were fixed in 10% natural buffered formalin, gradually dehydrated in ethanol and embedded in paraffin. Sections were stained with Hematoxylin and Eosin (H&E) for general histomorphology. Picro-sirius red (Gurr-BDH, England) was used for the detection of matrix collagens, and Toluidine blue (Serva, Germany) was used to detect matrix proteoglycans in chondrogenic cultures (Hyllested, J. L, et al 2005). Alizarin Red (Sigma) was used to detect calcium phosphate deposits on culture plates as evidence for bone mineralization. For immunofluorescence studies, cells were fixed in 4% paraformaldehyde in phosphate-buffered saline (PBS), and stained with the following primary antibodies, diluted in primary antibody diluent (Dako): anti-human type I collagen (Chemicon, Intnl, Inc. Temecula, Calif., USA, cat. No. MAB3391), anti-human alkaline phosphatase (R&D, Systems Inc, Minneapolis, Minn., USA, Cat. No. MAB1448), anti-human type II collagen (Chemicon, Cat. No. MAB8887) and anti human mitochondria (BioGenex, San Ramon, Calif., USA, Cat. No MU213-UC). DAPI was used for nuclear counterstaining. Appropriate secondary antibodies were used for visualization.

FACS analysis—Cells were removed from the culture dish with type IV collagenase (Worthington) (0.1%, 30-60 minutes at 37° C.) followed by Trypsin/EDTA (Sigma) for 5 minutes at 37° C. and re-suspended in a FACS buffer [Sigma, PBS supplemented with 2% fetal bovine serum (Gibco) and containing 0.05% NaN3]. Fc blocking was performed by addition of 4% Human serum (Sigma). Cells were probed for 30 minutes at room temperature with the specific monoclonal antibodies (Pharmingen; eBioscience; DAKO) or an appropriate isotype control antibodies (Pharmingen; eBioscience; DAKO) in FACS buffer. Cell were washed twice in FACS buffer, and analyzed using a FACSAria flow cytometer (Becton Dickinson). Acquisition was set for 10,000 events per sample. Dead cells were excluded from analysis by staining with 7AAD (eBioscience). Data were analyzed with Diva software (Becton Dickinson). Experiments were performed in duplicates.

Scaffold fabrication and cell seeding—Electrospun nanofiber scaffolds were made of a 1:1 blend of polycaprolactone (PCL) and poly (lactic acids) (PLA) by a process previously described (Ma, Z. et al 2005). The average thickness of the prepared scaffold was 500 μm, fiber diameter ranged between 200-450 nm, with porosity of 85%. For preparation for cell seeding, scaffold mat was cut into 0.5×0.5 cm$^2$ squares, gas-sterilized with ethylene oxide, immersed in 5 M sodium hydroxide and washed in PBS to increase surface hydrophilicity. For seeding the cells on scaffolds, subconfluent CTP cultures (passage 10-12) were collagenase-treated, trypsinized and counted. 5×10$^5$ cells were resuspended in 10 μl of CTP medium, seeded onto each scaffold and allowed to attach for 30 minutes before fresh medium was added. Cultures were maintained for one month before harvesting for analysis. Plain cultures on plastic plates were used as control.

In-vitro engineering of functional tendons—Tendons were spontaneously formed upon applying the new long-term high-density culture technique: subconfluent CTP cultures (passages 2-21) were regularly split and counted before seeding at a high density of 5-10×10$^6$ cells/cm$^2$ on tissue culture plates in the presence of CTP medium. Cultures were kept for long periods of up to 4 months in culture, with no further splitting.

Mechanical testing of in vitro engineered (formed) tendon grafts—Engineered constructs were removed from their culture plates immediately before testing. The construct diameter was measured at several positions along the length, using an optical microscope (Olympus BX 60×500 magnification). An average diameter was calculated, using measured values. Tensile testing was performed with a Micro Fiber Tensile Machine, outfitted with a 35 N load cell and a special stainless steel grips. The grips clamped the specimens by jaws machined from Delrin (acetal). The control of machine was performed by developed software on Matlab6 and data acquisition performed with National Instruments hardware on a PentiumII PC. The load cell was zeroed after the attachment of each sample. Samples were moistened by regularly applying drops of PBS. The gauge length was taken to be the length of the construct between the grips, which was measured from the calibrated images of a fast MotionScope CCD camera. Tests were conducted at a constant displacement rate of 0.08 mm/sec.

In-vivo studies—For subcutaneous transplantation (ectopic transplantation), cd1 nude mice were anesthetized and approximately 5 mm long incision was made in 2 or 3 locations on the back of the animal. The method for critical Achilles tendon injury model preparation is described in the description of FIGS. 16a-e. All animal experimental protocols were approved by the Animal Use and Care Committee of the Technion Faculty of Medicine.

In vivo transplantation of CTPs underneath kidney capsules—Subconfluent CTP cultures (passages 5 and 11) were scraped off the culture plates, washed with PBS and implanted underneath the kidney capsule of 5-week-old CB-17 SCID-beige mice (n=6). Six and twelve weeks after transplantation, kidneys were retrieved, fixed in 10% buffered formalin, embedded in paraffin, and sectioned for histological examination.

Example 1

Isolation of Connective Tissue Progenitor Cells from Human Embryonic Stem Cells

A cell source for tissue engineering should be highly proliferative while phenotypically stable in vitro, providing a sufficient amount of cells. Thus, undifferentiated hESCs, which can self-renew indefinitely while maintaining their pluripotency, present an ideal cell source for tissue engineering. However, stem cells lose their proliferation potential along the differentiation process, and indeed most published EB-based differentiation systems are limited in the amount of target cells obtained. As estimated elsewhere (Muschler, G. F. et al, 2002), approximately 7×10$^7$ osteoblasts are needed to form one cubic centimeter of a new bone. While reducing the present invention to practice, the present inventors have uncovered, through laborious experimentations, culturing conditions suitable for the isolation, propagation and differentiation of connective tissue progenitor cells, as follows.

Experimental Results

Isolation of connective tissue progenitor cells (CTPS) from hESCs derived embryoid bodies (EBs)—Ten-day-old EBs were dissociated with a combination of enzymatic digestion and aggressive mechanical agitation. The derived cells were cultured in the presence of a CTP medium containing ascorbic acid and dexamethasone, factors known to promote osteoblastic differentiation (Maniatopoulos, C., et al, 1988; Coelho, M. J. et al, 2000). The cells were cultured without splitting (passaging) in the presence of the CTP medium until reaching sub-confluency (between about 5-10 days) and were then subjected to serial passaging using type IV collagenase (0.1%, 30-60 minutes at 37° C.) followed by trypsinization (0.25%, 2-5 minutes at 37° C.). The growth kinetic pattern of the cells, which were continuously expanding without obvious senescence up to 25 passages, suggested the derivation of a putative cell line. At passage 20 the growth rate of the cells was slowed down (FIG. 1a) and the cells tended to form mineralized cultures at a higher frequency (data not shown). Cultures recovered well after freeze/thaw cycles, and showed the same proliferation and differentiation potential as prior to the freeze/thaw cycles. Light microscopy examination revealed a great resemblance in morphology between low passage hESC-derived CTPs and human fetal-derived CTP (FIGS. 27a-b). In addition, hESCs derived CTPs from early passages exhibit a morphology resembling that of mesenchymal stem cells (MSCs, FIG. 1b) and CTPs from later passages exhibit a morphology resembling that of fibroblasts (FIG. 1c).

CTPs exhibit clonogenic potential and normal karyotype—The clonality potential of the CTP cells was assessed by seeding single cells each in different culture wells. Colonies were formed in high efficiency (22 out of 24 experiments) and were identical in their growth kinetics, morphology and phenotype, as assessed by RT-PCR. Additionally, G banding analysis of CTP nuclei obtained from passages 7-8, 14 and 20 confirmed that the CTPs are karyotypically normal (data not shown).

CTPs are suitable for cell-based tissue engineering—As is shown in FIG. 26, assuming symmetric cell division, one well of a 6-well culture plate containing approximately 15-20 undifferentiated hESC colonies, potentially gives rise to approximately $3^{20}$ subconfluent 75 cm$^2$ culture flasks after 20 passages. Thus, one hESC-derived CTP from the first passage could potentially give rise to approximately 50 cubic centimeters of mineralized bone after 20 passages. Thus, the unique derivation method of the present invention generates a sufficient amount of cells for cell-based tissue engineering application.

Isolation of connective tissue progenitor cells (CTPs) from undifferentiated hESCs colonies—hESCs colonies were enzymatically digested with type IV Collagenase (0.1%, for 30-60 minutes at 37° C.) followed by aggressive mechanical agitation and dissociated cell clumps were further passed through a 40 μm mesh cell strainer (Falcon) to obtain a single cell suspension. The derived cells were cultured in the presence of a CTP medium containing ascorbic acid and dexamethasone. The cells were cultured without culture splitting (passaging) in the presence of the CTP medium until reaching sub-confluency (between about 5-10 days) and were then subjected to serial passaging using type IV collagenase (0.1%, 30-60 minutes at 37° C.) followed by trypsinization (0.25%, 2-5 minutes at 37° C.). The growth kinetic pattern of the cells, which were continuously expanding without obvious senescence up to 25 passages, suggested the derivation of a putative cell line. At passage 20 the growth rate of the cells was slowed down (data not shown) and the cells tended to form mineralized cultures at a higher frequency (data not shown). Cultures recovered well after freeze/thaw cycles, and showed the same proliferation and differentiation potential as prior to the freeze/thaw cycles.

Altogether, the present inventors have demonstrated that the CTP cells isolated from hESCs-derived EBs or the undifferentiated hESCs by culturing and passaging in the CTP medium exhibit high proliferative capacity (for at least 20 passages), in vitro stability (with normal karyotype) and clonogenic potential. In addition, the present inventors have uncovered that the CTPs of the present invention are suitable for cell-based tissue engineering.

Example 2

CTPs Express Markers of Mesenchymal and Osteoblast-Like Cells

To test the potential of the hESCs derived CTPs of the present invention to differentiate into the osteogenic lineage, the expression profile of the CTP cells of the present invention was assessed by RT-PCR, cDNA microarray and FACS analyses, as follows.

Experimental Results

CTPs express osteogenic markers—Gene expression of CTP cells grown in the presence of the CTP medium from passages 1 and 10, was assessed by RT-PCR analysis. As is shown in FIGS. 2a-u, CTPs stably express core binding factor alpha 1 (CBFA1), and SOX9, both are early transcription factors known to play a major role in osteoblast and chondrocyte differentiation. Type I collagen, the most abundant extracellular protein which is synthesized by osteoblasts, osteonectin and osteopontin, two major non-collagenous bone matrix proteins, parathyroid hormone receptor 1 (PTHR1), which regulates mineral homeostasis and bone formation, and bone-specific alkaline phosphatase, which binds phosphor to calcium and forms bone hydroxyapatite, were all detected at low and higher passages, indicating osteogenic potential.

Immunofluorescence analysis of the hESCs derived CTPs demonstrated that the CTPs of the present invention express alkaline phosphatase (ALP, FIG. 22a) and osteocalcin (FIG. 22b), markers of the osteogenic lineage.

Expression profiles of CTP-derived osteogenic-like cells—The gene expression profile of the cells was detected using cDNA microarray analysis using a set of approximately 100 osteogenesis-related genes. The common transcripts were compared between hESC-derived CTPs (passage 1 and 9) to human fetal CTPs (passage 1). Two independent experiments were performed. The complete list of positive transcripts is shown in Table 2, hereinbelow. Forty transcripts were found to be shared among hESC-derived CTPs and human fetal CTPs, including growth factors and associate molecules, cell adhesion molecules, and matrix associated proteins. A significant overlap of 36 transcripts shared by the three populations (i.e., undifferentiated hESCs, hESC-derived CTPs and human fetal CTPs) was observed. This set of shared transcripts represent genes that though known to play a significant role in osteogenesis, are already switched-on at the hESC stage. In addition, CBFA1, type I collagen, ALP, osteopontin and PTH-R1, which were tested by RT-PCR (FIGS. 2a, c, f, e, g), were found to be positive at the hESC stage as well (Table 2). This can be attributed to the assumption that uncontrolled background differentiation of presumably undifferentiated hESCs always occur, thus total RNA extracted from hESC cultures represents also cells at different stages of differentiation. In addition, gene expression profiling of hESC lines has shown a significant number of markers of differentiation to be positive (34-36). Speculatively, this is to say that differentiation, rather than being a process where stem cells acquire markers of differentiated cells, could be a process where stem cells express all or most markers at low levels, and reduce the expression of these genes gradually as they differentiate while upregulating the expression of a limited set of genes (37).

TABLE 2

Expression profile of undifferentiated hESCs, hESCs-derived CTPs (p9) and fetal CTPs

| Symbol | Gene Name | Undiff-hESCs | CTP, p9 | Fetal | Description |
|---|---|---|---|---|---|
| ALPL | AP-TNAP/HOPS | p | p | n | Alkaline phosphatase, liver/bone/kidney |
| ANXA5 | ANX5/ENX2 | p | p | p | Annexin A5 |
| ARSE | CDPX/CDPX1 | n | n | n | Arylsulfatase E (chondrodysplasia punctata 1) |
| BGLAP | BGP | n | n | n | Bone gamma-carboxyglutamate (gla) protein (osteocalcin) |
| BGN | DSPG1/PG-S1 | p | p | p | Biglycan |
| BMP1 | PCOLC/TLD | n | p | n | Bone morphogenetic protein 1 |
| BMP2 | BMP2A | p | p | n | Bone morphogenetic protein 2 |
| BMP3 | BMP3 | p | p | n | Bone morphogenetic protein 3 (osteogenic) |
| BMP4 | BMP2B/BMP2B1 | n | n | n | Bone morphogenetic protein 4 |
| BMP5 | MGC34244 | p | p | p | Bone morphogenetic protein 5 |
| BMP6 | VGR/VGR1 | n | n | n | Bone morphogenetic protein 6 |
| BMP7 | OP-1 | p | p | p | Bone morphogenetic protein 7 (osteogenic protein 1) |
| BMP8B | BMP8/OP2 | p | p | p | Bone morphogenetic protein 8b (osteogenic protein 2) |
| BMPR1A | ACVRLK3/ALK3 | p | p | p | Bone morphogenetic protein receptor, type IA |
| CASR | FHH/FIH | n | n | n | Calcium-sensing receptor (hypocalciuric hypercalcemia 1, severe neonatal hyperparathyroidism) |
| CD36 | FAT/GP3B | n | n | n | CD36 antigen (collagen type I receptor, thrombospondin receptor) |
| SCARB1 | CD36L1/CLA-1 | p | p | p | Scavenger receptor class B, member 1 |
| CSIG | L12/PBK1 | n | n | n | Ribosomal L1 domain containing 1 |
| COL10A1 | COL10A1 | p | p | n | Collagen, type X, alpha 1(Schmid metaphyseal chondrodysplasia) |
| COL11A1 | CO11A1/COLL6 | n | p | p | Collagen, type XI, alpha 1 |
| COL12A1 | COL12A1L/TYPE XII | n | p | p | Collagen, type XII, alpha 1 |
| COL14A1 | UND | p | p | n | Collagen, type XIV, alpha 1 (undulin) |
| COL15A1 | COL15A1 | n | p | p | Collagen, type XV, alpha 1 |
| COL16A1 | 447AA/FP1572 | p | p | p | Collagen, type XVI, alpha 1 |
| COL17A1 | BP180/BPAG2 | n | p | n | Collagen, type XVII, alpha 1 |
| COL18A1 | KNO | p | p | p | Collagen, type XVIII, alpha 1 |
| COL19A1 | COL9A1L/D6S228E | n | n | n | Collagen, type XIX, alpha 1 |
| COL1A1 | AA 694-711/OI4 | n | n | n | Collagen, type I, alpha 1 |
| COL2A1 | COL11A3/SEDC | p | p | p | Collagen, type II, alpha 1 (primary osteoarthritis, spondyloepiphyseal dysplasia, congenital) |
| COL3A1 | EDS4A | p | p | p | Collagen, type III, alpha 1 (Ehlers-Danlos syndrome type IV, autosomal dominant) |

TABLE 2-continued

Expression profile of undifferentiated hESCs, hESCs-derived CTPs (p9) and fetal CTPs

| Symbol | Gene Name | Undiff-hESCs | CTP, p9 | Fetal | Description |
|---|---|---|---|---|---|
| COL4A3 | TUMSTATIN | n | n | n | Collagen, type IV, alpha 3 (Goodpasture antigen) |
| COL4A4 | CA44 | p | p | p | Collagen, type IV, alpha 4 |
| COL4A5 | ASLN/ATS | n | n | n | Collagen, type IV, alpha 5 (Alport syndrome) |
| COL5A1 | COL5A1 | p | p | p | Collagen, type V, alpha 1 |
| COL7A1 | EBD1/EBDCT | n | p | n | Collagen, type VII, alpha 1 (epidermolysis bullosa, dystrophic, dominant and recessive) |
| COL9A2 | EDM2/MED | p | p | p | Collagen, type IX, alpha 2 |
| CSF2 | GMCSF | p | n | n | Colony stimulating factor 2 (granulocyte-macrophage) |
| CSF3 | G-CSF/GCSF | n | n | n | Colony stimulating factor 3 (granulocyte) |
| CTSK | CTS02/CTSO | n | n | p | Cathepsin K (pycnodysostosis) |
| DCN | DSPG2/PG40 | p | p | p | Decorin |
| EGF | URG | n | n | n | Epidermal growth factor (beta-urogastrone) |
| EGFR | ERBB/ERBB1 | p | p | n | Epidermal growth factor receptor (erythroblastic leukemia viral (v-erb-b) oncogene homolog, avian) |
| FGF1 | AFGF/ECGF | n | p | n | Fibroblast growth factor 1 (acidic) |
| FGF2 | BFGF/FGFB | p | p | n | Fibroblast growth factor 2 (basic) |
| FGF3 | HBGF-3/INT2 | n | n | n | Fibroblast growth factor 3 (murine mammary tumor virus integration site (v-int-2) oncogene homolog) |
| FGFR1 | BFGFR/C-FGR | p | p | p | Fibroblast growth factor receptor 1 (fms-related tyrosine kinase 2, Pfeiffer syndrome) |
| FGFR2 | BEK/BFR-1 | p | n | n | Fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| FGFR3 | ACH/CEK2 | p | n | n | Fibroblast growth factor receptor 3 (achondroplasia, thanatophoric dwarfism) |
| FLT1 | FLT/VEGFR1 | p | n | n | Fms-related tyrosine kinase 1 (vascular endothelial growth factor/vascular permeability factor receptor) |
| FN1 | CIG/FINC | p | p | p | Fibronectin 1 |
| GDF10 | BMP-3B/BMP3B | p | p | n | Growth differentiation factor 10 |
| ICAM1 | BB2/CD54 | n | p | n | Intercellular adhesion molecule 1 (CD54), human rhinovirus receptor |

TABLE 2-continued

Expression profile of undifferentiated hESCs, hESCs-derived CTPs (p9) and fetal CTPs

| Symbol | Gene Name | Undiff-hESCs | CTP, p9 | Fetal | Description |
|---|---|---|---|---|---|
| IGF1 | IGFI | n | p | p | Insulin-like growth factor 1 (somatomedin C) |
| IGF1R | JTK13 | p | p | n | Insulin-like growth factor 1 receptor |
| IGF2 | IGF-II | n | n | n | Insulin-like growth factor 2 (somatomedin A) |
| ITGA1 | CD49a | p | p | p | Integrin, alpha 1 |
| ITGA2 | BR/CD49B | n | n | n | Integrin, alpha 2 (CD49B, alpha 2 subunit of VLA-2 receptor) |
| ITGA3 | CD49C/GAP-B3 | p | p | n | Integrin, alpha 3 (antigen CD49C, alpha 3 subunit of VLA-3 receptor) |
| ITGAM | CD11B/CR3A | n | n | n | Integrin, alpha M (complement component receptor 3, alpha; also known as CD11b (p170), macrophage antigen alpha polypeptide) |
| ITGAV | CD51/MSK8 | p | p | p | Integrin, alpha V (vitronectin receptor, alpha polypeptide, antigen CD51) |
| ITGB1 | CD29/FNRB | p | p | p | Integrin, beta 1 (fibronectin receptor, beta polypeptide, antigen CD29 includes MDF2, MSK12) |
| SMAD1 | BSP1/JV4-1 | p | p | p | SMAD, mothers against DPP homolog 1 (*Drosophila*) |
| SMAD2 | MADH2/HSMAD2 | p | p | p | SMAD, mothers against DPP homolog 2 (*Drosophila*) |
| SMAD3 | HSPC193/HST17436 | p | p | n | SMAD, mothers against DPP homolog 3 (*Drosophila*) |
| SMAD4 | DPC4/JIP | p | p | p | SMAD, mothers against DPP homolog 4 (*Drosophila*) |
| SMAD5 | DWFC/JV5-1 | p | p | p | SMAD, mothers against DPP homolog 5 (*Drosophila*) |
| SMAD6 | HST17432/MAD | p | p | n | SMAD, mothers against DPP homolog 6 (*Drosophila*) |
| SMAD7 | MAD/MADH7 | p | p | n | SMAD, mothers against DPP homolog 7 (*Drosophila*) |
| SMAD9 | MAD/MADH6 | p | p | p | SMAD, mothers against DPP homolog 9 (*Drosophila*) |
| MMP10 | SL-2/STMY2 | n | n | n | Matrix metalloproteinase 10 (stromelysin 2) |
| MMP13 | CLG3 | p | p | p | Matrix metalloproteinase 13 (collagenase 3) |
| MMP2 | CLG4/CLG4A | p | p | p | Matrix metalloproteinase 2 (gelatinase A, 72 kDa gelatinase, 72 kDa type IV collagenase) |
| MMP8 | CLG1/HNC | n | n | p | Matrix metalloproteinase 8 (neutrophil collagenase) |

TABLE 2-continued

Expression profile of undifferentiated hESCs, hESCs-derived CTPs (p9) and fetal CTPs

| Symbol | Gene Name | Undiff-hESCs | CTP, p9 | Fetal | Description |
|---|---|---|---|---|---|
| MMP9 | GELB/CLG4B | n | n | p | Matrix metalloproteinase 9 (gelatinase B, 92 kDa gelatinase, 92 kDa type IV collagenase) |
| MSX1 | HOX7/HYD1 | p | n | n | Msh homeo box homolog 1 (*Drosophila*) |
| MSX2 | CRS2/FPP | n | n | n | Msh homeo box homolog 2 (*Drosophila*) |
| NFKB1 | EBP-1/KBF1 | n | p | p | Nuclear factor of kappa light polypeptide gene enhancer in B-cells 1 (p105) |
| PDGFA | PDGF-A/PDGF1 | p | p | n | Platelet-derived growth factor alpha polypeptide |
| RUNX2 | CCD/AML3 | p | p | p | Runt-related transcription factor 2 |
| SERPINH1 | ASTP3/CBP1 | p | p | p | Serine (or cysteine) proteinase inhibitor, clade H (heat shock protein 47), member 1, (collagen binding protein 1) |
| SERPINH1 | ASTP3/CBP1 | p | p | p | Serine (or cysteine) proteinase inhibitor, clade H (heat shock protein 47), member 1, (collagen binding protein 1) |
| SOX9 | CMD1/CMPD1 | n | n | n | SRY (sex determining region Y)-box 9 (campomelic dysplasia, autosomal sex-reversal) |
| SPARC | ON | p | p | p | Secreted protein, acidic, cysteine-rich (osteonectin) |
| SPP1 | BNSP/BSPI | p | n | n | Secreted phosphoprotein 1 (osteopontin, bone sialoprotein I, early T-lymphocyte activation 1) |
| TGFB1 | BETA 1/CED | n | p | n | Transforming growth factor, beta 1 (Camurati-Engelmann disease) |
| TGFB2 | TGF b2 | n | p | n | Transforming growth factor, beta 2 |
| TGFB3 | TGF b3 | p | p | p | Transforming growth factor, beta 3 |
| TGFBR1 | ACVRLK4/ALK-5 | p | p | p | Transforming growth factor, beta receptor I (activin A receptor type II-like kinase, 53 kDa) |
| TGFBR2 | HNPCC6/MFS2 | n | p | n | Transforming growth factor, beta receptor II (70/80 kDa) |
| TNF | DIF/TNF-ALPHA | p | p | p | Tumor necrosis factor (TNF superfamily, member 2) |
| TWIST1 | ACS3/BPES2 | p | p | n | Twist homolog 1 (acrocephalosyndactyly 3; Saethre-Chotzen syndrome) (*Drosophila*) |
| VCAM1 | INCAM-100 | n | n | n | Vascular cell adhesion molecule 1 |
| VDR | NR1I1 | n | n | n | Vitamin D (1,25-dihydroxyvitamin D3) receptor |

TABLE 2-continued

Expression profile of undifferentiated hESCs, hESCs-derived CTPs (p9) and fetal CTPs

| Symbol | Gene Name | Undiff-hESCs | CTP, p9 | Fetal | Description |
|---|---|---|---|---|---|
| VEGF | VEGFA | p | p | p | Vascular endothelial growth factor |
| VEGFB | VEGFL/VRF | n | n | n | Vascular endothelial growth factor B |
| VEGFC | FLT4-L/VRP | p | p | p | Vascular endothelial growth factor C |
| PUC18 | pUC18 | n | n | n | PUC18 Plasmid DNA |
| PUC18 | pUC18 | n | n | n | PUC18 Plasmid DNA |
| PUC18 | pUC18 | n | n | n | PUC18 Plasmid DNA |
|  |  | n | n | n |  |
|  |  | n | n | n |  |
|  |  | n | n | n |  |
| GAPDH | G3PD/GAPD | p | p | p | Glyceraldehyde-3-phosphate dehydrogenase |
| GAPDH | G3PD/GAPD | p | p | p | Glyceraldehyde-3-phosphate dehydrogenase |
| PPIA | CYPA/CYPH | p | p | p | Peptidylprolyl isomerase A (cyclophilin A) |
| PPIA | CYPA/CYPH | p | p | p | Peptidylprolyl isomerase A (cyclophilin A) |
| PPIA | CYPA/CYPH | p | p | p | Peptidylprolyl isomerase A (cyclophilin A) |
| PPIA | CYPA/CYPH | p | p | p | Peptidylprolyl isomerase A (cyclophilin A) |
| RPL13A | RPL13A | p | p | p | Ribosomal protein L13a |
| RPL13A | RPL13A | p | p | p | Ribosomal protein L13a |
| ACTB | b-Actin | p | p | p | Actin, beta |
| ACTB | b-Actin | p | p | p | Actin, beta |

Table 2: The cDNA array membrane (GEArray Q Series Human Osteogenesis Gene Array HS-026; SuperArray Bioscience Corp., Frederic, MD USA) was hybridized with biotin-labeled cDNA prepared from undifferentiated hESCs (H9.2; undiff-hESCs), human fetal CTPs (fetal, passage 1) and hESC-derived CTPs at passage 1 (p1) or passage 9 (p9) which were grown in the presence of the CTP medium. The presence (positive, "p") or absence (negative, "n") of each of the genes in the array is indicated.

CTPs exhibit unique populations of CD105 positive and negative cells—FACS analyses performed on hESCs derived CTPs from passages 6-16 using antibodies specific to the CD105, CD166, CD44, CD29, CD45, HLA-ABC and HLA-DR surface markers demonstrated relatively high level of population purity with surface markers characteristic of MSCs (FIGS. 3a-k). Thus, the CTPs of the present invention were positive for CD105, CD166, CD44 and CD29, while negative for CD45, a hematopoietic marker. Additionally, all hESCs derived CTP cells were also positive for HLA-ABC (FIG. 3f) and negative for HLA-DR (FIG. 3h, the major histocompatibility complex antigens), an expression pattern characteristic to MSCs. Level of cell purity was confirmed to be high, with two main sub-populations: CD105 positive (42%) and CD105 negative (58%) cells (FIG. 3a). As is further shown in FIGS. 3h-k, the CD105 positive cells were also positive for CD166, CD29 and CD44 and negative for CD45. On the other hand, the CD105 negative cells were positive for CD29 and CD44, and negative for CD166.

Altogether, the FACS results demonstrate that hESCs-derived CTPs express markers of mesenchymal stem cells (MSCs). The cDNA microarray and the RT-PCR analyses demonstrate the presence of specific markers of connective tissue derivatives including osteogenic lineage, chondrogenic lineage, tendons and ligaments. In addition, immunostaining analyses demonstrated that the CTP cells isolated according to the teachings of the present invention express markers of the osteogenic lineage and thus can differentiate to form osteoblasts and bone tissue.

Example 3

CTPs are Capable of Producing Bone Matrix

To test to capacity of the CTPs of the present invention to differentiate into the osteogenic lineage and form mineralized matrix, inorganic phosphate was added to the CTP medium and the CTP cell cultures were assessed for the presence of mineralized matrix, as follows.

CTP cells produce mineralized matrix—To test the capacity of the CTP cells of the present invention to form mineralized matrix, inorganic phosphate (beta-glycerophosphate) was added to the CTP medium. Briefly, CTPs from any passage of passages 1-25 were grown in a CTP medium supplemented with 10 mM beta-glycerophosphate and the potential of matrix formation was assessed. As is shown in FIG. 4a, enhanced mineralization which was visible macroscopically, occurred either after 20 passages, or was induced earlier at different passages if cells were grown until over-confluent. Mineralization was confirmed by Alizarin Red staining (FIG. 4b), and scanning electron microscopy (FIG. 4c) coupled with EDS spectra analysis (FIG. 4d). Moreover, immunostaining analysis demonstrated the presence of self-produced matrix which is positive for type I collagen (FIG. 4c). Thus, these results demonstrate that the CTPs of the present invention are capable of forming bone nodules containing calcium-phosphate deposits, the major component of bone minerals.

Altogether, these results demonstrate that hESCs-derived CTPs are capable of differentiating into cells of the osteogenic lineage while producing mineralized matrix.

Example 4

Human ESC-Derived CTP Cells are Capable of Differentiating into the Chondrogenic Lineage To induce to chondrogenic differentiation, the two differentiation methods described under "General Materials and Experimental Methods" were employed.

Experimental Results

Induction of CTPs to chondrogenic differentiation using the "intact layer" method—To induce chondrogenic differentiation, subconfluent cultures (passages 5-13) were trypsinized and placed as an intact layer in suspension, in the presence of the CTP medium. After 10 days the tissue was harvested for analysis. H&E staining showed considerable apoptosis occurring in the center of the tissue sample, probably due to lack of nutrients and oxygen delivery in static culture conditions (FIG. 5a). At numerous locations at the viable periphery of the sample round chondrocyte-like cells were detected embedded in lacunae, resembling early cartilage (FIG. 5a). Picro-sirius red staining demonstrated extensive collagenous matrix surrounding the cells (FIG. 5b). Immunohistochemistry using an antibody directed against the S-100 protein, calcium-binding protein found in cartilage (38) detected small clusters of positively stained cells within the viable chondrocyte-like area (FIG. 5d).

Induction of CTPs to chondrogenic differentiation using the pellet culture method—The induction of chondrogenic differentiation was further assessed using the pellet culture system of chondrogenic differentiation as published elsewhere (24). Cells (passages 1-9) were grown as pellet cultures in the presence of low serum TGF-β3 supplemented medium as described in method 2 of chondrogenic differentiation in the General Materials and Experimental Methods, hereinabove. A section of one-month-old pellet culture was stained with Toluidine blue, showing the matrix proteoglycans (FIG. 23). Earlier pellet cultures were not positively stained (data not shown). RT-PCR analyses showed up regulation of type X collagen, chondroitin sulfate proteoglycan 4 (SC-4) and cartilage oligomeric matrix protein (COMP) (FIGS. 6a-d). Type X collagen is a non-fibril-forming collagen restricted to the hypertrophic, calcifying zone of growth plate cartilage (39). Chondroitin sulfate proteoglycan 4, is known to be found on immature cells such as in the developing cartilage (40), and cartilage oligomeric matrix protein (COMP) is a key non-collagenous matrix protein (41).

Altogether, these results demonstrate that hESCs-derived CTPs are capable of differentiating into the chondrogenic lineage while expressing cartilage markers.

Example 5

Enhanced Matrix Production by CTPs Seeded on Nanofiber Scaffolds

To provide cells with a suitable 3D environment that would support their growth and organization into a complex tissue, the electrospun, PCL/PLA nanofiber scaffolds (FIG. 7a) were utilized, as follows.

Experimental Results

Seeding of CTPs on electrospun PCL/PLA scaffolds resulted in connective tissue formation—$5 \times 10^5$ CTPs (passage 10-12) resuspended in 10 µl of CTP medium were seeded on scaffolds and grown in the presence of the CTP medium for one month before harvesting for analysis. Histological analysis showed an high matrix to cell ratio (ECM-rich) connective tissue formation, with mesenchymal-like cells aligned in parallel, surrounded with extensive fibrous collagen matrix, with a thin remnant of the scaffold at the basal side of the construct, suggesting it has degraded over time (FIG. 7e). Scanning electron microscopy illustrates the beginning of matrix production and a progressive tissue-like patches formation until a firm 3D sheet-like tissue is generated (FIGS. 7b-d). The presence of mineral deposits [hydroxyapatite (calcium-phosphate)] was confirmed by EDS analysis (data not shown). Cells grown in the same conditions but on plastic tissue culture plates did not show any form of 3D tissue-like formation (data not shown).

Altogether, these results demonstrate the ability of the hESCs derived CTPs of the present invention to form mineralized matrix and tissue-like patches when grown on nano-scaffolds.

Example 6

CTPs are Capable of Forming Tendon Grafts In Vitro

To test the ability of the hESCs derived CTPs of the present invention to form a more compact and organized tissue, the long-term high-density culture technique was optimized, as follows.

CTP cells are capable of forming a tendon-like tissue—The long-term high-density culture technique induces the self-assembly of 3D, cylinder-shaped constructs, which morphologically resemble early developed tendons. This process begins as a single cell attaching to the culture plate sidewall, forming fibrous matrix with a tendon-like shape. As is shown in FIGS. 8a-b, hESCs derived CTPs which were cultured in the presence of CTP medium were capable of forming a tendon-like construct following 8 weeks in culture (FIG. 8a) and a clear tendon tissue which grew up to 5 centimeters following 4 months in culture (FIG. 8b) or 6-8 cm following 4-5 months (data not shown). Further immunostaining analyses demonstrated the progressive assembly of long, cylinder-shaped constructs which express type I collagen (FIG. 9a). At a later developmental stage (following 2-3 weeks in culture), wider structures were observed (FIG. 9b), until the formation of well defined, tendon-like constructs (FIG. 9c). Histological examination shows organized, parallel-aligned cells, with high matrix-to-cell ratio (FIG. 9d). Additional SEM analyses of the tendon graft demonstrated well-defined fibrous structure and parallel orientation of elongated, fibroblast-like looking, cells (FIGS. 10a-c). Thus, these cells formed a well organized, highly cellular collagen-associated mineralized tissue, as evident by histology and electron microscopy (FIGS. 10a-c and 11a-d). Altogether, these experiments demonstrate the engineering of functional tendons from the hESCs derived CTPs of the present invention.

Evaluation of the mechanical properties of the engineered constructs derived from the CTP cells—Three-month old constructs (CTP-derived, passages 10-12) were removed from the culture plate and were put into a custom built testing machine (FIGS. 24a-b). As is shown in FIG. 12, the strain-stress response of the constructs resembles a non-linear behavior. At a strain of 0.05, the stress-strain response starts to increase linearly until failure occurs in the middle of the construct. The tangent modulus measured at a strain of 0.15 is 660 MPa and the ultimate tensile strength (UTS) at a strain of 0.25 is 110 MPa. The average UTS of 4 samples was 105±10 MPa and the average modulus was 660±50 MPa.

TABLE 3

Mechanical evaluations of the in vitro formed tendon grafts of the present invention

| Test No. | Young modulus E[MPa] | maximal stress [MPa] | maximal strain [%] |
|---|---|---|---|
| 1 | 574.9 | 79.6 | 30.2 |
| 2 | 423.0 | 63.3 | 33.2 |
| 3 | 671.8 | 79.9 | 31.4 |
| 4 | 676.8 | 95.9 | 35.1 |
| Average | 586.6 | 79.7 | 32.4 |
| STD | 118.7 | 13.3 | 2.1 |

Table 3: Stress-stress tests of in vitro engineered tendon grafts. The initial length and diameter of the tendons were 2.4 mm and 0.2 mm respectively. The tendon constructs were stressed until failure at a strain rate of 0.02 sec$^{-1}$. Shown are the Young modulus values (MPa), the maximal stress (MPa) and the maximal strain (%). The average tangent modulus is 586.6 ± 118.7 MPa, and ultimate tensile strength (UTS) of 79.7 ± 13.3 MPa.

Altogether, these results demonstrate the formation of a tendon-like structure with excellent mechanical properties resembling that of mature rather than immature tendons.

Example 7

CTP Cells Form Connective Tissue in Vivo

To assess the commitment of the hESCs-derived CTP cells to the connective tissue lineage on one hand, and to examine their tumorigenic properties on the other hand, CTPs were transplanted into 6 SCID-beige mice, as follows.

CTP cells are non-tumorigenic in vivo—CTPs (passages 5 and 11) were implanted underneath the kidney capsule of 5-week-old SCID-beige mice. Using this animal model, the present inventors have previously shown that undifferentiated hESCs are capable of forming teratomas (data not shown). Six and twelve weeks post transplantation, kidneys were harvested for analysis. Both macroscopic examination and histological analysis did not detect any form of teratoma formation (data not shown). Instead, a localized sub-capsular formation of loose connective tissue was observed, with no evidence of other tissue type (data not shown). Using this model, it is possible to explore the in-vivo developmental potential of hESC-derived CTPs.

Altogether, these results demonstrate that hESCs-derived CTPs are non-tumorigenic and are committed to the connective cell lineage in vivo.

Example 8

CTP Cells Form Bone and Cartilage Tissues in Vivo

To assess the potential of the hESCs derived CTPs of the present invention to form cartilage and bone tissue in vivo, CTPs were subcutaneously transplanted into cd1 nude mice and the formation of ectopic new bone and cartilage was assessed, as follows.

CTP derived ectopic transplants are biocompatible, well-vascularized masses with radio-opaque bone tissue—For subcutaneous transplantation of hESCs derived CTPs, the mice were anesthetized and approximately 5 mm long incisions were made in 2 or 3 locations on the back of the animal. CTP cells from a single T75 flask were injected in each incision. Ectopic transplants visible following 8 weeks of transplantation (FIG. 13a) included bone tissue, as confirmed by the radio-opaque transplants seen by X-ray analysis (FIG. 13b). Close examination of the ectopic transplants following the removal of the back skin revealed the presence of non-cancerous, well-vascularized masses (FIG. 13c), demonstrating that the ectopic transplant is biocompatible, well integrated within the recipient mouse and not rejected by its immune system.

CTP derived ectopic transplants include bone and cartilage tissues—Histological analyses of the ectopic transplants revealed the formation of new bone (FIGS. 14a-c) and hypertrophic cartilage (FIGS. 14d-e) tissues with early stage of mineralized bone matrix formation (FIG. 14a), and a later stage showing osteon-like structures and new bone formation (FIGS. 14b and c).

CTP derived ectopic transplants include mineralized bone tissue—As is further shown in FIGS. 15a-b, analysis of frozen sections of non-demineralized tissue demonstrated the formation of mineral deposits within the ectopic transplants of the hESCs derived CTPs.

CTP derived ectopic transplants are of a human origin—To verify that the ectopic transplants are derived from the hESCs derived CTPs of the present invention histological sections of the ectopic transplants were subjected to immunostaining analysis using the anti-human mitochondria antibody. As is shown in FIG. 25a, the newly-formed ectopic tissue is positively stained with the anti-human mitochondria antibody, demonstrating the human origin of the ectopic tissue.

Altogether, these results demonstrate the ability of the hESCs derived CTPs of the present invention to form bone and cartilage tissue in vivo.

Example 9

The in Vivo Repair of Critical Achilles-Tendon Injury Using a Tendon Graft Formed from HESCs Derived CTPs To test the functionality of the in vitro engineered tendon graft from the hESCs derived CTPs of the present invention (as described in Example 6, hereinabove), the present inventors have induced a critical Achilles-tendon injury in mice and implanted the tendon graft of the present invention, as follow.

FIGS. 16a-e schematically depict the strategy of repairing a critical Achilles-tendon injury using the in vitro generated tendon graft of the present invention. High-density CTP cultures were grown with no further splitting for 4-5 weeks to form a sheet-like tissues in culture plates (FIG. 16a). Next tissues were gently removed from plates using a cell scraper and rolled to form rounded cylinders (FIG. 16b). Non-absorbable sutures were inserted at the ends of a construct through all layers (FIG. 16c). Constructs were immediately used for transplantation or kept inside custom-made templates made from flexible silicon tubes embedded in agar plates. Full thickness, 3-4 mm long segment of the Achilles tendon in nude mice was cut to form a critical gap (FIG. 16d). Next constructs were sutured to the proximal and distal edges of the injured Achilles tendon (FIG. 16e).

Experimental Results

In vivo repair of a critical Achilles-tendon injury using the in vitro formed tendon graft of the present invention—Following the induction of a critical Achilles-tendon injury the treated mice are unable to extent their ankle, resulting in a maximal extension of less than 90 degrees (FIG. 17a). To repair the injury, hESCs derived CTPs are subjected to a high-density culture to form tendon grafts (FIG. 17b) which are then implanted in the injured mice (FIG. 17c). One month after transplantation the implanted mice are capable of extending their leg with a maximal extension greater than 90 degrees (FIG. 17d).

The transplanted tendon grafts are remodeled and exhibit excellent biomechanical properties—Following 6-8 weeks of transplantation, the transplanted tendon grafts exhibit good integration at the sites of suturing (FIGS. 18a-c), with circulating blood vessels invading the graft (FIGS. 19a-b). Further histological evaluation of the transplanted grafts demonstrated that the grafts remodeled and integrated well (FIGS. 20a-c) with smoother edges (FIGS. 21a-b). Further biomechanical testing using the tensile test machine (FIGS. 24a-b) demonstrated that the stress/strain behavior of the tendon graft after transplantation resembles that of a native rat tail tendon (FIG. 21c, compare the pattern of the blue graph with that of the green graph).

The transplanted tendon grafts are of a human origin—To confirm the human origin of the transplanted tendon grafts, a cross section of the transplanted tendon was subjected to immunostaining analysis using the anti-human mitochondria antibody. As is shown in FIG. 25b, the transplanted tendon is positively stained with the anti-human mitochondria antibody, demonstrating its human origin.

Example 10

Formation of ECM and Acellularized Matrix Using the Connective Tissue Progenitor Cells Experimental Results Formation of ECM in vitro—For the formation of extracellular matrix (ECM), the CTPs were plated at high densities ($5-10 \times 10^5$ cells/cm$^2$) in tissue culture plates in the presence of a culture medium comprising ascorbic acid and dexamethasone. After about 4 weeks in culture (other periods of time are also possible) sheet-like tissue was formed. The sheet-like tissue was subjected to freeze-drying and/or cell removal. Freeze-drying was done using standard lyophilization device. The resultant tissue was completely devoid of viable cells as detected using e.g., standard viability assays, thus reducing the risk of cell-based tumor formation and immune rejection.

Dry ECM tissues are biocompatible—Dry tissues were stored at room temperature in dry conditions. The dry tissue formed was found to be biocompatibile as evidenced by seeding the dry tissues with different cell types (Human embryonic kidney 293 cells) and observing the formation of secondary new tissue, as a model for allogenic cell seeding (data not shown).

The dried tissues were characterized by histology, immunostaining, electron microscopy and the results demonstrated that the ECM was kept intact, in a native form, supporting biological cellular activities (data not shown).

Acellularization of ECM—Cell removal was done chemically with detergents such as SDS (0.1%, incubation time 20-60 minutes), combined with protease inhibitors, essentially as described in Cartmell J S. and Dunn M G., 2000, J. Biomed Mater. Res. 49(1): 134-40. Histology and electron microscopy assays show that the resultant tissue is completely acellular, while the ECM is preserved.

Acellularized ECM tissue is biocompatible—The biocompatibility of the acellular tissues was demonstrated by seeding different cell types onto the tissue, with the formation of secondary new tissue, as a model for allogenic cell seeding (data not shown).

Altogether, the freeze-dried and/or de-cellularized CTP-derived tissues are easy to handle and shape, suture retentive, can rapidly re-hydrate (indicates high hydrophilicity) and can be combined with standard hydrogels to make an injectable form.

It will be appreciated that the intact ECM can be conditioned by specific cell types, such as skin, skeletal muscle, cardiac muscle, fat, cartilage, bone, etc., to create tissue specific, specialized intact ECM tissues. This can be done by co-culturing CTPs with the second cell type before the formation of the primary tissue, or by seeding the second cell type onto the already processed CTP-derived tissue, allowing the cells to interact with the intact-ECM tissue, before secondary round of freeze-drying and/or cell removal will occur. Alternatively, the second cell type taken from the patient can be left to grow on the tissue prior to transplantation back into the patient.

Purified ECM components—Total protein component or selected proteins is purified from CTPs or CTP-derived tissues according to standard protein purification methods. The resultant protein is assessed by gel electrophoresis, western blotting and proteomics analysis. Such proteins are processed in order to achieve clinical-grade injectable formulas and other forms suitable for biomaterial applications.

Analysis and Discussion hESCs as a model for connective tissue development—hESCs are pluripotent cells derived from the inner cell mass of the blastocyst, and are known to possess virtually unlimited proliferation ability and differentiation potential. It has been proposed that ESC differentiation through the formation of EBs mimics the early developmental stages during embryogenesis and can serve as an alternative model to investigate human embryonic development, considering the limitations of studying human embryos (42).

Connective tissue elements are derived from stem cells of mesodermal origin. Bone tissue is formed mainly through two distinct processes: endochondral bone formation and intramembranous ossification. Endochondral ossification applies to the formation of long and short bones during embryonic development. This begins when mesenchymal stem cell differentiation leads to cartilaginous tissue development, and is followed by both appositional growth and endochondral maturation of chondrocytes to form a growth plate. Cartilage matrix is then calcified and absorbed by osteoclasts, followed with vascular invasion and replacement with osteoblasts and bone tissue. Intramembranous ossification applies to the formation of flat bones, directly from mesenchymal cells without an intermediary cartilaginous differentiation (29, 43).

In this study the present inventors have demonstrated the efficient derivation of a connective tissue progenitor cell line from hESCs. Grown in the presence of medium containing factors known to promote osteoblast phenotype, the generated cells show both osteogenic and chondrogenic potential, and are able to assemble into tendon-resembling constructs. Purification and expansion of the desire cell type from the mixed population of growing EBs is a great challenge in hESC research. Various methods have been utilized so far, including fluorescence- and magnetic-activated cell sorting and separation (FACS, MACS), and genetic manipulations, with either inserting genes of interest or silencing them. In contrast to these strategies and without the use of such manipulations, the present inventors have generated a stable and committed cell line derived from EBs, thus introducing an easy, efficient and potentially innocent method for cell isolation and expansion.

The cells are named "connective tissue progenitors" (CTPs) since they are non-tumorigenic and committed to connective tissue derivative differentiation. Initially presumed to be osteoprogenitors, they showed a greater differentiation and developmental potential.

The plasticity or multipotency of osteoblasts has been shown in the adult. Human trabecular bone-derived cells have multi-lineage in-vitro developmental potential, and can be induced to differentiate into osteoblasts, chondrocytes and adipocytes (8, 44), similar to bone marrow-derived mesenchymal stem cells (9). The presently derived CTPs, which phenotypically resemble osteoblasts, are able to form a well-mineralized matrix and can be further induced to form several other types of connective tissue derivatives. In addition, as is demonstrated in Example 1, hereinabove, unlike osteoblasts of which $7 \times 10^7$ cells are needed to form one cubic centimeter of a new bone, one hESC-derived CTP from the first passage could potentially give rise to approximately 50 cubic centimeters of mineralized bone after 20 passages.

The extracellular matrix (ECM) and ECM-mimicking scaffolds—In contrast to parenchymal organs, which are mainly cellular and function via their cells, most of the volume of connective tissues consists of their functional element—the extracellular matrix (ECM) (45). Connective tissue ECMs cope with tensile and compressive mechanical stresses. Tension is transmitted and resisted by nano-scaled fibrous proteins (collagen, elastin), while compression is opposed by water-soluble proteoglycans, such as chondroitin sulphate (46). The proteoglycan part form a highly hydrated, gel-like "ground substance" in which the fibrous proteins are embedded (47). Scaffolds used in tissue engineering are designed to provide cells with a 3D environment, promoting their attachment, proliferation and differentiation while meeting their nutritional and biological needs. They can be made of either natural or synthetic biodegradable polymers, in various shapes and forms, such as fibers, foams, hydrogels and capsules (1). Ideally, scaffolds should mimic the chemical and physical structure of the native extracellular matrix, providing cells with the most "homey" environment. Thus, considerable effort is being made to create an ECM-mimicking tissue-engineered scaffold. It has been supposed that nano-scaled fabricated surface topography of a synthetic scaffold would better mimic the native matrix. Electrospinning is the most common and practical way to fabricate polymeric nanofiber matrix (26). Recently an electospun PCL scaffold was shown to support mesenchymal stem cell growth and differentiation into osteoblasts (48). The present inventors have hypothesized that electrospun nanofiber biodegradable polymer scaffolds would support hESC-derived cells' organization into complex 3D tissues. The present inventors have shown that PLC/PLA nanofiber scaffolds promote the growth of CTPs, providing them with an excellent platform for mineralized extracellular matrix production and complex tissue formation. In addition, the present study demonstrate the successful formation of a sheet-like tissue, which could potentially be further developed toward cell-based tissue engineered implantable constructs for clinical applications.

Engineering tendons—Tendons are a dense form of connective tissue that is responsible for the transmission of force from muscle to bone. Studies of the chick embryo have shown the embryonic tendon to be mainly cellular with type I collagen to be the principle ECM fibrilar component, while the matrix/cell ratio increases significantly during development (49). Collagen fibrils in tendon are packets of helically wound protofibrils, aligned in parallel and define the mechanical properties of the tendon. While no early marker of developing tendons had been described yet, it has been shown that axial tendon progenitors are generated by interaction between the muscle and cartilage progenitors, placing the developing tendon in a spatial position that allows the final and coordinated development of the functional musculoskeletal system (50). In the absence of cartilage differentiation, chondroprogenitors can switch fate to tendon (51). Tissue engineering of tendons and ligaments offers a great promise to the field of reconstructive medicine. A number of cell types have been utilized for this purpose, with bone marrow-derived mesenchymal stem cells being the better choice so far (52-54). There is also a growing knowledge about the importance of mechanical stimuli during tissue development and remodeling, shown to improve the functional characteristics of engineered tissues (55-56). Various biological and synthetic substitutes have been utilized for the repair or replacement of damaged tendons and ligaments. Different tendons and ligaments differ chemically in the amount of collagen, glycosaminoglycans and type I to type III collagen ratio (52). The present inventors have postulated that hESC derived connective tissue progenitors could be used to generate tendon-like tissues. Applying a long-term high-density culture technique, the present inventors have successfully generated self-assembling, cylinder-shaped constructs, which morphologically resemble early tendons. Mechanical testing of the constructs demonstrated an average tangent modulus of 660±50 MPa. This is in the same order of magnitude as that of a modulus of an adult rat tail tendon, reported to be 632 MPa (57). Additionally, the average ultimate tensile strength (UTS) of the presently engineered constructs is 105±10 MPa, which is in the same order of magnitude of failure test results reported for human Achilles tendons, showing pick stresses ranging 50-90 MPa (58). In a recent study, fibroblasts isolated from rat Achilles tendon were induced to assemble into constructs resembling immature tendons, with a tangent modulus of 17 MPa and UTS of 2 MPa (54). The results of the present study are both an order of magnitude greater than the values reported for the rat engineered constructs, suggesting that CTP-derived tendons mechanically resemble mature rather than immature tendons. These constructs could serve as a great starting point for further study, applying tissue engineering concepts toward the development of a biological engineered tendon substitutes.

In summary, in this study the present inventors have demonstrated the successful derivation of connective tissue progenitors (CTPs) from human embryonic stem cells (hESCs). Providing with virtually unlimited number of cells as building blocks for cell-based tissue engineering, CTPs are shown to be easily isolated and expanded, with both osteogenic and chondrogenic differentiation potential. The present inventors have combined nanofiber scaffolding to create 3D sheet-like tissues, and applied the long-term high-density culture method to assemble 3D constructs resembling early tendons, both ultra structurally and biophysically. These encouraging results may serve to support further efforts towards characterizing these hESC-derived CTPs, exploring their developmental potential, controlling their fate, developing platforms for engineering tissues as well as providing a great tool for studying human development.

In view of the limited availability of tissues for transplantation, this work not only holds great promise for a potentially unlimited source of cells for tissue engineering, but also suggests a great tool for investigating human embryonic development.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Additional References are Cited in Text

1. Vacanti, J. P. & Langer, R. (1999) Lancet 354, SI32-SI 34.
2. Sharma, B. & Elisseeff, J. H. (2004) Ann Biomed Eng. 32, 148-159.
3. Muschler, G. F., Nakamoto, C. & Griffith, L. G. (2004) J Bone Joint Surg Am. 86, 1541-1558.
4. Lavik, E. & Langer, R. (2004) Appl Microbiol Biotechnol 65, 1-8.
5. Betz, R. R. (2002) Orthopedics. 25, s561-s570.
6. Meyer, U., Joos, U. & Wiesmann, H. P. (2004) Int J Oral Maxillofac Surg 33, 325-332.
7. Muschler, G. F. & Midura, R. J. (2002) Clin Orthop Relat Res 66-80.
8. Sottile, V., Halleux, C., Bassilana, F., Keller, H. & Seuwen, K. (2002) Bone 30, 699-704.
9. Pittenger, M. F., Mackay, A. M., Beck, S. C., Jaiswal, R. K., Douglas, R., Mosca, J. D., Moorman, M. A., Simonetti, D. W., Craig, S, & Marshak, D. R. (1999) Science 284, 143-147.
10. Mastrogiacomo, M., Derubeis, A. R. & Cancedda R. (2005) J Cell Physiol 204, 594-603.
11. Zuk, P. A., Zhu, M., Mizuno, H., Huang, J., Futrell. J. W., Katz, A. J., Benhaim, P., Lorenz, H. P. & Hedrick, M. H. (2001) Tissue Eng 7, 211-228.
12. Thomson, J. A., Itskovitz-Eldor, J., Shapiro, S. S., Waknitz, M. A., Swiergiel, J. J., Marshall, V. S. & Jones, J. M. (1998) Science 282, 1145-1147.
13. Itskovitz-Eldor, J., Schuldiner, M., Karsenti, D., Eden, A., Yanuka, O., Amit, M., Soreq, H. & Benvenisty, N. (2000) Mol Med 6, 88-95.
14. Schuldiner, M., Yanuka. O., Itskovitz-Eldor. J., Melton, D. A. & Benvenisty, N. (2000) Proc Natl Acad Sci USA 97, 11307-11312.
15. Hwang, W. S., Roh, S. I., Lee, B. C., Kang, S. K., Kwon, D. K., Kim, S., Kim, S. J., Park, S. W., Kwon, H. S., Lee, C. K. et al. (2005) Science 308, 1777-1783.
16. Levenberg, S., Huang, N. F., Lavik, E., Rogers, A. B., Itskovitz-Eldor, J. & Langer, R. (2003) Proc Natl Acad Sci USA. 100, 12741-12746.
17. Gerecht-Nir, S., Cohen, S., Ziskind, A. & Itskovitz-Eldor, J (2004) Biotechnol Bioeng. 88, 313-320.
18. Cao, T., Heng, B. C., Ye, C. P., Liu, H., Toh, W. S., Robson, P., Li, P., Hong, Y. H. & Stanton, L. W. (2005) Tissue Cell 37, 325-334.
19. Bielby, R. C., Boccaccini, A. R., Polak, J. M. & Buttery L. D. (2004) Tissue Eng 10, 1518-1525.
20. Sottile, V., Thomson, A. & McWhir, J. (2003) Cloning Stem Cells 5, 149-155.
21. Barberi, T., Willis, L. M., Socci, N. D. & Studer, L. (2005) PLoS Med 2, e161
22. Amit, M., Carpenter, M. K., Inokuma, M. S., Chiu, C. P., Harris, C. P., Waknitz, M. A., Itskovitz-Eldor, J. & Thomson, J. A. (2000) Dev Biol 227, 271-278.
23. Montjovent, M. O., Burri, N., Mark, S., Federici, E., Scaletta, C., Zambelli, P. Y., Hohlfeld, P., Leyvraz, P. F., Applegate, L. L. & Pioletti, D. P. (2004) Bone 35, 1323-1333.
24. Kim, M. S., Hwang, N. S., Lee, J., Kim, T. K., Leong, K., Shamblott, M. J., Gearhart, J. & Elisseeff, J. (2005) Stem Cells 23, 113-123.
25. Hyllested, J. L., Veje, K. & Ostergaard, K. (2002) Osteoarthritis Cartilage 10, 333-343.
26. Ma, Z., Kotaki, M., Inai, R. & Ramakrishna S. (2005) Tissue Eng 11, 101-109.
27. Maniatopoulos, C., Sodek, J. & Melcher, A. H. (1988) Cell Tissue Res 254, 317-330.
28. Coelho, M. J. & Fernandes, M. H. (2000) Biomaterials 21, 1095-1102.
29. Smith, N., Dong, Y., Lian, J. B., Pratap, J., Kingsley, P. D., van Wijnen, A. J., Stein, J. L., Schwarz, E. M., O'Keefe, R. J., Stein, G. S. et al (2005) Cell Physiol 203, 133-143.
30. Rossert, J., Terraz, C. & Dupont, S. (2000) Nephrol Dial Transplant 15, Suppl. 66-88.
31. Bellows, C. G., Aubin, J. E. & Heersche, J. N. (1991) Bone Miner 14, 27-40.
32. Sodek, J., Ganss, B. & McKee, M. D. (2000) Crit Rev Oral Biol Med 11,279-303
33. Mannstadt, M., Juppner, H. & Gardella, T. J. (1999) Am J Physiol 277, F665-F675.
34. Sperger, J. M., Chen, X., Draper, J. S., Antosiewicz, J. E., Chon, C. H., Jones, S. B., Brooks, J. D., Andrews, P. W., Brown, P. O. & Thomson, J. A. (2003) Proc Natl Acad Sci USA 100, 13350-13355.
35. Golan-Mashiach, M., Dazard, J. E., Gerecht-Nir, S., Amariglio, N., Fisher, T., Jacob-Hirsch, J., Bielorai, B., Osenberg, S., Barad, O., Getz, G. et al (2005) FASEB J 19, 147-149.
36. Bhattacharya, B., Miura, T., Brandenberger, R., Mejido, J., Luo, Y., Yang, A. X., Joshi, B. H., Ginis, I., Thies, R. S., Amit, M. et al (2004) Blood 103, 2956-2964.
37. Zipori, d. (2004) Nat Rev Genet. 5, 873-878.
38. Karabela-Bouropoulou, V., Markaki, S. & Milas, C. (1988) Pathol Res Pract 183, 761-766.
39. Reichenberger, E., Aigner, T., von der Mark, K., Stoss, H. & Bertling, W. (1991) Dev Biol 148, 562-572.
40. Levine, J. M. & Nishiyama, A. (1996) Perspect Dev Neurobiol, 3, 245-259.
41. Hedbom, E., Antonsson, P., Hjerpe, A., Aeschlimann, D., Paulsson, M., Rosa-Pimentel, E., Sommarin, Y., Wendel, M., Oldberg, A. & Heinegard, D. (1992) J Biol Chem 267, 6132-6136.
42. Dvash, T. & Benvenisty, N. (2004) Best Pract Res Clin Obstet Gynaecol 18, 929-940.
43. Mistry, A. S. & Mikos, A. G. (2005) Adv Biochem Eng Biotechnol 94, 1-22.
44. Noth, U., Osyczka, A. M., Tuli, R., Hickok, N. J., Danielson, K. G. & Tuan, R. S. (2002) J Orthop Res 20, 1060-1069.
45. Aigner, T. & Stove, J. (2003) Adv Drug Deliv Rev 55, 1569-1593.
46. Scott, J. E. (2003) J Physiol 553, 335-343.
47. Cell Junctions, Cell Adhesion, and the Extracellular Matrix (1994) in Molecular Biology of the Cell, eds. Alberts, B., Johnson, A., Lewis, J., Raff, M., Roberts, K. & Walter, P. (Garland Publishing), pp. 971-995.

48. Yoshimoto, H., Shin, Y. M., Terai, H. & Vacanti, J. P. (2003) Biomaterials 24, 2077-2282.
49. Canty, E. G. & Kadler, K. E. (2002) Comp Biochem Physiol A Mol Integr Physiol 133, 979-985.
50. Brent, A. E., Schweitzer, R. & Tabin, C. J. (2003) Cell 113, 235-248.
51. Brent, A. E., Braun, T. & Tabin, C. J. (2005) Development 132, 515-528.
52. Vunjak-Novakovic, G., Altman, G., Horan, R. & Kaplan, D. L. (2004) Annu Rev Biomed Eng 6, 131-156.
53. Van Eijk, F., Saris, D. B., Riesle, J., Willems, W. J., Van Blitterswijk, C. A., Verbout, A. J. & Dhert, W. J. (2004) Tissue Eng 10, 893-903.
54. Calve, S., Dennis, R. G., Kosnik, P. E. 2nd, Baar, K., Grosh, K. & Arruda, E. M. (2004) Tissue Eng 10, 755-761.
55. Grenier, G., Remy-Zolghadri, M., Larouche, D., Gauvin, R., Baker, K., Bergeron, F., Dupuis, D., Langelier, E., Rancourt, D., Auger, F. A. et al (2005) Tissue Eng 11, 90-100.
56. Lee, C. H., Shin, H. J., Cho, I. H., Kang, Y. M., Kim, I. A., Park, K. D. & Shin, J. W. (2005) Biomaterials 26, 1261-1270.
57. Cartmell, J. S. & Dunn, M. G. (2000) J Biomed Mater Res 49, 134-140.
58. Wren, T. A., Lindsey, D. P., Beaupre, G. S. & Carter, D. R. (2003) Ann Biomed Eng 31, 710-717.

---

What is claimed is:

1. A method of generating connective tissue progenitor cells which are capable of differentiating into more than one cell lineage of the connective tissue, the method comprising culturing embryoid bodies (EBs) or single embryonic stem cells (ESCs) in a culture medium which comprises dexamethasone and ascorbic acid, wherein said culturing comprises passaging the connective tissue progenitor cells, whereas a first passage of the passaging is effected no more than 10 days following initial culturing of the cells of the embryoid bodies or of said single ESCs in said culture medium, thereby generating the connective tissue progenitor cells.

2. The method of claim 1, wherein said single ESCs are obtained by enzymatically and/or mechanically dissociating said embryonic stem cells.

3. The method of claim 1, wherein said culturing is effected under feeder-free culturing conditions.

4. The method of claim 1, wherein said culture medium further comprises inorganic phosphate.

5. The method of claim 1, wherein said culture medium further comprises serum or serum replacement.

6. The method of claim 1, wherein said passaging is effected for at least 20 times.

7. The method of claim 1, wherein said culturing is effected under xeno-free conditions.

8. The method of claim 1, wherein said cell lineage of the connective tissue is selected from the group consisting of a chondrogenic lineage, an osteogenic lineage, an adipocytic lineage and a tendon and ligament lineage.

* * * * *

UNITED STATES PATENT AND TRADEMARK OFFICE
CERTIFICATE OF CORRECTION

PATENT NO.        : 8,343,762 B2
APPLICATION NO.   : 12/087610
DATED             : January 1, 2013
INVENTOR(S)       : Joseph Itskovitz-Eldor et al.

Page 1 of 1

It is certified that error appears in the above-identified patent and that said Letters Patent is hereby corrected as shown below:

On the Title page,

Item [60] Related U.S. Application Data, line 4, "Nov. 1, 2006"

should be changed to --Jan. 11, 2006--

Signed and Sealed this
Twenty-eighth Day of May, 2013

Teresa Stanek Rea
*Acting Director of the United States Patent and Trademark Office*

SEQUENCE LISTING

<160> NUMBER OF SEQ ID NOS: 40

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
ccgcacgaca accgcaccat                                               20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
cgctccggcc cacaaatctc                                               20

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
atctgaagaa ggagagcgag                                               20

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
tcagaagtct ccagagcttg                                               20

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
gcacacaatg gattgcaagg                                               20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
taaccactgc tccactctgg                                         20

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
gcagcaatga caacaagacc                                         20

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
cttctcattc tcatggatct tc                                      22

<210> SEQ ID NO 9
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 9
ctaggcatca cctgtgccat acc                                     23

<210> SEQ ID NO 10
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 10
cagtgaccag ttcatcagat tcatc                                   25

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
tggagcttca gaagctcaac                                         20

<210> SEQ ID NO 12
<211> LENGTH: 27
<212> TYPE: DNA
<213> ORGANISM: Artificial sequence
<220> FEATURE:
<223> OTHER INFORMATION: Single strand DNA oligonucleotide

```
<400> SEQUENCE: 12
atctcgttgt ctgagtagta ccagtcc                                       27

<210> SEQ ID NO 13
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 13
cacagcctca tcttcatgg                                                19

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
gcatctcata gtgcatctgg                                               20

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
tggtttaact ggagccaagg                                               20

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
gcccaccatg aatttatatc                                               20

<210> SEQ ID NO 17
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 17 cccttttgc tgctagtatc c                                              21

<210> SEQ ID NO 18
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 18
ctgttgtcca ggtttcctg gcac                                           24

<210> SEQ ID NO 19
<211> LENGTH: 20
```

```
<212> TYPE: DNA
<213> ORGANISM: Artificial sequence
<220> FEATURE:
<223> OTHER INFORMATION: Single strand DNA oligonucleotide

<400> SEQUENCE: 19
caggacgact ttgatgcaga                                                   20

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
aagctggagc tgtcctggta                                                   20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
atccgagaca ccaacgagac                                                   20

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
ggcttcaccc tcactgatgt                                                   20

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
cccccatcct cactacaaac                                                   20

<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24
atccagggtt cctctgtgtg                                                   20

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
tgcaagcttc cctttcagt                                                    20
```

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
ctgcacagcc gaaattgtaa                                        20

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
cctccaactg ctcctactcg                                        20

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
cgggtctacc tgattctcca                                        20

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
gtgcctggac tgatttggtt                                        20

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
tgtggaggca atttgtttga                                        20

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
tgaagaacct tcacgcattg                                        20

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
gagccattgt caacagcaga						20

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
tgcagaacaa cgacatctcc						20

<210> SEQ ID NO 34
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 34
ccaggttcaa agccactgtt						20

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 35
gctatggact gccctacacc						20

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36
agctcctggg acaccaacta						20

<210> SEQ ID NO 37
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 37
ggagtcagct gccaagagac						20

<210> SEQ ID NO 38
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 38
acacacgtgc acctcatcat						20

<210> SEQ ID NO 39
<211> LENGTH: 20

```
<212> TYPE: DNA
<213> ORGANISM: Artificial sequence
<220> FEATURE:
<223> OTHER INFORMATION: Single strand DNA oligonucleotide

<400> SEQUENCE: 39
cgtggagtac cttgtcagca                                           20

<210> SEQ ID NO 40
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 40
aggtaaccgg tgactgatgc                                           20
```